(12) United States Patent
Decker et al.

(10) Patent No.: US 9,333,248 B2
(45) Date of Patent: *May 10, 2016

(54) METHODS AND COMPOSITION RELATED TO TH-1 DENDRITIC CELLS

(71) Applicant: THE BOARD OF REGENTS, THE UNIVERSITY OF TEXAS SYSTEM, Austin, TX (US)

(72) Inventors: William K. Decker, Houston, TX (US); Elizabeth J. Shpall, Houston, TX (US); Krishna V. Komanduri, Village of Palmetto Bay, FL (US); Dongxia Xing, The Woodlands, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/248,908

(22) Filed: Apr. 9, 2014

(65) Prior Publication Data
US 2014/0286975 A1 Sep. 25, 2014

Related U.S. Application Data

(63) Continuation of application No. 13/132,517, filed as application No. PCT/US2009/066807 on Dec. 4, 2009, now Pat. No. 8,728,806.

(60) Provisional application No. 61/120,437, filed on Dec. 6, 2008.

(51) Int. Cl.
| | | |
|---|---|---|
| *A61K 39/00* | (2006.01) | |
| *A61K 35/00* | (2006.01) | |
| *C12N 15/85* | (2006.01) | |
| *C12N 5/0784* | (2010.01) | |
| *C12N 5/0783* | (2010.01) | |

(52) U.S. Cl.
CPC .......... *A61K 39/0011* (2013.01); *C12N 5/0636* (2013.01); *C12N 5/0639* (2013.01); *A61K 2039/5154* (2013.01); *A61K 2039/57* (2013.01); *C12N 2500/46* (2013.01); *C12N 2501/02* (2013.01); *C12N 2501/22* (2013.01); *C12N 2501/23* (2013.01); *C12N 2501/25* (2013.01)

(58) Field of Classification Search
CPC .................. A61K 2039/5154; A61K 2039/57; A61K 39/0011; C12N 2500/46; C12N 2501/02; C12N 2501/22; C12N 2501/23; C12N 2501/25; C12N 5/0639
USPC .......... 424/185.1; 435/375, 377, 455
See application file for complete search history.

(56) References Cited

U.S. PATENT DOCUMENTS

| | | | |
|---|---|---|---|
| 6,194,204 B1 | 2/2001 | Crawford et al. | 435/372 |
| 6,228,640 B1 | 5/2001 | Cezayirli et al. | 435/325 |
| 7,105,154 B2 | 9/2006 | Sokawa et al. | 424/85.4 |
| 7,659,119 B2 | 2/2010 | Steinman et al. | 435/377 |
| 8,728,806 B2 * | 5/2014 | Decker et al. | 435/325 |
| 2001/0023072 A1 | 9/2001 | Crawford et al. | 435/368 |
| 2003/0096314 A1 | 5/2003 | Steinman et al. | 435/7.2 |
| 2006/0057130 A1 | 3/2006 | Nair et al. | 424/93.21 |
| 2006/0073123 A1 * | 4/2006 | Mi et al. | 424/93.21 |
| 2007/0248578 A1 | 10/2007 | Tcherepanova | 424/93.21 |
| 2008/0171023 A1 | 7/2008 | Salgaller et al. | 424/93.7 |
| 2008/0254537 A1 | 10/2008 | Boynton et al. | 435/373 |

FOREIGN PATENT DOCUMENTS

| | | |
|---|---|---|
| WO | WO 2007/067782 | 6/2007 |
| WO | WO 2007067782 A2 * | 6/2007 |
| WO | WO 2008/055354 | 5/2008 |

OTHER PUBLICATIONS

Antonia, et al., "Combination of p53 cancer vaccine with chemotherapy in patients with extensive stage small cell lung cancer," *Clin. Cancer Res.*, 12:878-87, 2006.
Arnez, et al., "Glycyl-tRNA synthetase uses a negatively charged pit for specific recognition and activation of glycine," *J. Mol. Biol.*, 286:1449-59, 1999.
Banchereau and Palucka, "Dendritic cells as therapeutic vaccines against cancer," *Nat. Rev. Immunol.*, 5:296-306, 2005.
Banchereau, et al., "Dendritic cells: controllers of the immune system and a new promise for immunotherapy," *Ann. N.Y. Acad. Sci.*, 987:180-7, 2003.
Banchereau, et al., "Immune and clinical responses in patients with metastatic melanoma to CD34(+) progenitor-derived dendritic cell vaccine," *Cancer Res.*, 61:6451-8, 2001.
Behrens, et al., "Helper T cells, dendritic cells and CTL immunity," *Immunol. Cell. Biol.*, 82:84-90, 2004.
Chang, et al., "A phase I trial of tumor lysate-pulsed dendritic cells in the treatment of advanced cancer," *Clin. Cancer Res.*, 8:1021-32, 2002.
Decker and Shpall, "Progress in dendritic cell immunotherapy: elucidating the enigma of Th-1 polarization," *Hum. Vaccin.*, 4:162-4, 2008.
Decker, et al., "Deficient T(H)-1 responses from TNF-alpha-matured and alpha-CD40-matured dendritic cells," *J. Immunother.*, 31:157-65, 2008.
Decker, et al., "Dendritic cell immunotherapy for the treatment of neoplastic disease," *Biol. Blood Marrow Transplant.*, 12:113-25, 2006.
Decker, et al., "Double loading of dendritic cell MHC class I and MHC class II with an AML antigen repertoire enhances correlates of T-cell immunity in vitro via amplification of T-cell help," *Vaccine*, 24:3203-16, 2006.
Geiger, et al., "Vaccination of pediatric solid tumor patients with tumor lysate-pulsed dendritic cells can expand specific T cells and mediate tumor regression," *Cancer Res.*, 61:8513-9, 2001.

(Continued)

*Primary Examiner* — Janet Epps-Smith
(74) *Attorney, Agent, or Firm* — Parker Highlander PLLC

(57) ABSTRACT

Certain embodiments of the invention are directed to methods for inducing an immunologic response to a tumor in a patient using mature dendritic cells transfected with a nucleic acid composition encoding one or more tumor antigens and loaded with a corresponding tumor antigen composition.

29 Claims, 16 Drawing Sheets

(56) References Cited

OTHER PUBLICATIONS

GenBank Accession No. NM_001040280, "*Homo sapiens* CD83 molecule (CD83), transcript variant 2, mRNA," 1992.

GenBank Accession No. NP_001035370, "CD83 antigen isoform b [*Homo sapiens*]," 1992.

Gilboa and Vieweg, "Cancer immunotherapy with mRNA-transfected dendritic cells," *Immunol. Rev.*, 199:251-63, 2004.

Haluska, et al., "Immunologic gene therapy of melanoma: phase I study of therapy with autologous dendritic cells transduced with recombinant adenoviruses encoding melanoma antigens," *Proc. Am. Soc. Clin. Oncol.*, 19:453a, Abstract 1777, 2000.

Hartgers, et al., "Towards a molecular understanding of dendritic cell immunobiology," *Immunol. Today*, 21:542-5, 2000.

Heiser, et al., "Autologous dendritic cells transfected with prostate-specific antigen RNA stimulate CTL responses against metastatic prostate tumors," *J. Clin. Invest.*, 109:409-17, 2002.

Hertz and Yanover, "PepDist: a new framework for protein-peptide binding prediction based on learning peptide distance functions," *BMC Bioinformatics*, 7:S3, 2006.

Ioannou, et al., "Myositis overlap syndromes.," *Curr. Opin. Rheumatol.*, 11:468-74, 1999.

Kobelt, et al., "The interaction between dendritic cells and herpes simplex virus-1," *Curr. Top Microbiol. Immunol.*, 276:145-61, 2003.

Kokhaei, et al., "Apoptotic tumor cells are superior to tumor cell lysate, and tumor cell RNA in induction of autologous T cell response in B-CLL," *Leukemia*, 18:1810-5, 2004.

Kyte and Gaudernack, "Immuno-gene therapy of cancer with tumour-mRNA transfected dendritic cells," *Cancer Immunol. Immunother.*, 55:1432-42, 2006.

Lechmann, et al., "CD83 on dendritic cells: more than just a marker for maturation," *Trends Immunol.*, 23:273-5, 2002.

Lim and Bailey-Wood, "Idiotypic protein-pulsed dendritic cell vaccination in multiple myeloma," *Int. J. Cancer*, 83:215-22, 1999.

Morse, et al., "Migration of human dendritic cells after injection in patients with metastatic malignancies," *Cancer Res.*, 59:56-8, 1999.

Nair, et al., "Induction of tumor-specific cytotoxic T lymphocytes in cancer patients by autologous tumor RNA-transfected dendritic cells," *Ann. Surg.*, 235:540-9, 2002.

Nestle, et al., "Vaccination of melanoma patients with peptide- or tumor lysate-pulsed dendritic cells," *Nat. Med.*, 4:328-32, 1998.

Oaks and Hallett, "Cutting edge: a soluble form of CTLA-4 in patients with autoimmune thyroid disease," *J. Immunol.*, 164:5015-8, 2000.

Ochsenbein, et al., "Roles of tumour localization, second signals and cross priming in cytotoxic T-cell induction," *Nature*, 411:1058-64, 2001.

Office Action issued in U.S. Appl. No. 13/132,517, mailed Apr. 24, 2013.

Office Action issued in U.S. Appl. No. 13/132,517, mailed Feb. 1, 2013.

Office Action issued in U.S. Appl. No. 13/132,517, mailed Oct. 10, 2013.

PCT International Preliminary Report on Patentability issued in International Application No. PCT/US2009/066807, mailed Jun. 16, 2011.

PCT International Search Report and Written Opinion, issued in International Application No. PCT/US2009/066807, Oct. 6, 2010.

Rocha and Tanchot, "Towards a cellular definition of CD8+ T-cell memory: the role of CD4+ T-cell help in CD8+ T-cell responses," *Curr. Opin. Immunol.*, 16:2590-63, 2004.

Safdar, et al., "De novo T-lymphocyte responses against baculovirus-derived recombinant influenzavirus hemagglutinin generated by a naive umbilical cord blood model of dendritic cell vaccination," *Vaccine*, 27:1479-84, 2009.

Scholler, et al., "Cutting edge: CD83 regulates the development of cellular immunity," *J. Immunol.*, 168:2599-602, 2002.

Steinman, et al., "Tolerogenic dendritic cells," *Annu. Rev. Immunol.*, 21:685-711, 2003.

Tham, et al., "Activation-induced nonresponsiveness: a Th-dependent regulatory checkpoint in the CTL response," *J. Immunol.*, 168:1190-7, 2002.

Timmerman, et al., "Idiotype-pulsed dendritic cell vaccination for B-cell lymphoma: clinical and immune responses in 35 patients," *Blood*, 99:1517-26, 2002.

Titzer, et al., "Vaccination of multiple myeloma patients with idiotype-pulsed dendritic cells: immunological and clinical aspects," *Br. J. Haematol.*, 108:805-16, 2000.

Tjoa, et al., "Evaluation of phase I/II clinical trials in prostate cancer with dendritic cells and PSMA peptides," *Prostate*, 36:39-44, 1998.

Toungouz, et al., "Transient expansion of peptide-specific lymphocytes producing IFN-gamma after vaccination with dendritic cells pulsed with MAGE peptides in patients with mage-AI/A3-positive tumors," *J. Leukoc. Biol.*, 69:937-43, 2001.

Tozer, et al., "Vaccination with autologous CD34+ derived dendritic cells transduced with an adenovirus expressing human gp100 in patients with metastatic melanoma," *Proc. Am. Soc. Clin. Oncol.*, 21:352a, Abstract 1407, 2002.

Vegh and Mazurnder, "Generation of tumor cell lysate-loaded dendritic cells preprogrammed for IL-12 production and augmented T cell response," *Cancer Immunol. Immunother.*, 52:67-79, 2003.

Wolkers, et al., "Antigen bias in T cell cross-priming," *Science*, 304:1314-7, 2004.

Zhou and Tedder, "A distinct pattern of cytokine gene expression by human CD83+ blood dendritic cells," *Blood*, 86:3295-301, 1995.

Zhou and Tedder, "Human blood dendritic cells selectively express CD83, a member of the immunoglobulin superfamily," *J. Immunol.*, 154:3821-35, 1995.

Zinkernagel, "On cross-priming of MHC class I-specific CTL: rule or exception?" *Eur. J. Immunol.*, 32:2385-92, 2002.

Zinser, et al., "Prevention and treatment of experimental autoimmune encephalomyelitis by soluble CD83," *J. Exp. Med.*, 200:345-51, 2004.

\* cited by examiner

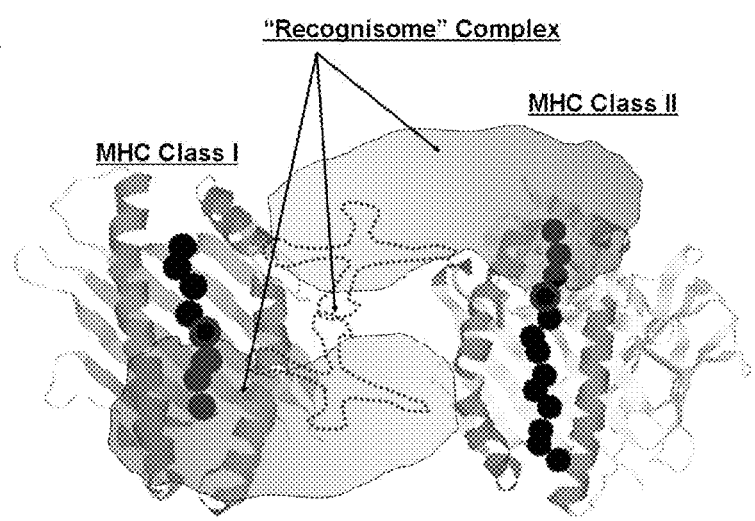
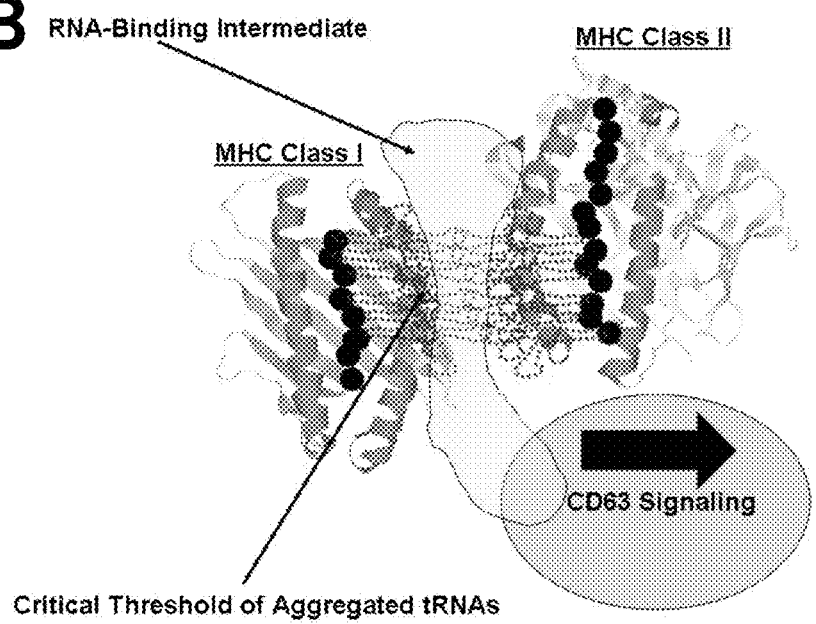
FIG. 1

A (SEQ ID NO: 3)

```
 80 MPECELLISKEEWSYIVETPHPENGTCVPGVYADYEELREQLSSVQSFERRFETFKESSWPHHTVTGVRASCSHNQKSSF
                (B8-166)                    (A3-172)
160 VRELIWLTGKNGLYPNLSKSTVMRKEREVLVLWQVHHPEDIGECRALVITENAYPSVVSEHVSRRFTPELLAERPKVKDQE
         (DR3-162)                                      (DR3-197)
240 GRIWYTWILLEPGDTIIFEANGNLIAPWYAFALSRGPQSGIITSNAPNDECDAKCQTPQGAINSSLPFQWVHPVTIGECP
320 KVVRSAKLRMVTGLRNIPSIQSEGLFQAIAGFIECWWTCMVQGWYGTHHQKEQESGVAADQRSTOMAINGTINKVWSVIE
                                                                      (A1-453)
400 RNSTQFTAVGKEFNKLERMENLNRKVDGEFLDIWTYNAEILFPNETLDFGSWVNLYPKVESQLZNMAKEIGNGC
                                       (A2-443)              (DR3-440)
```

B Disruption by Ethanolamine          No Disruption

```
B8-166   WLTGKNGL             A2-443       VLLENERTL
(SEQ ID NO: 4) |||X||X|    (SEQ ID NO: 6)  |||||||||
DR3-162  RNLLWLTGKNGLYPN      DR3-440      ELLVLLENERTLDFH
(SEQ ID NO: 5)                (SEQ ID NO: 7)
```

FIG. 13

SEQUENCE LISTING

<160> NUMBER OF SEQ ID NOS: 7

<210> SEQ ID NO 1

```
<211> LENGTH: 18
<212> TYPE: DNA
<213> ORGANISM: Artificial Sequence
<220> FEATURE:
<223> OTHER INFORMATION: Synthetic primer

<400> SEQUENCE: 1
tggcccagcc tgctgtgg                                              18

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tctgggttcc gttgcctatg                                            20

<210> SEQ ID NO 3
<211> LENGTH: 401
<212> TYPE: PRT
<213> ORGANISM: Artificial Sequence
<220> FEATURE:
<223> OTHER INFORMATION: Synthetic peptide

<400> SEQUENCE: 3
```

Asn Pro Glu Cys Glu Leu Leu Ile Ser Lys Glu Ser Trp Ser Tyr Ile
 1               5                  10                  15

Val Glu Thr Pro Asn Pro Glu Asn Gly Thr Cys Tyr Pro Gly Tyr Phe
            20                  25                  30

Ala Asp Tyr Glu Glu Leu Arg Glu Gln Leu Ser Ser Val Ser Ser Phe
        35                  40                  45

Glu Arg Phe Glu Ile Phe Pro Lys Glu Ser Ser Trp Pro Asn His Thr
    50                  55                  60

Val Thr Gly Val Ser Ala Ser Cys Ser His Asn Gly Lys Ser Ser Phe
65                  70                  75                  80

Tyr Arg Asn Leu Leu Trp Leu Thr Gly Lys Asn Gly Leu Tyr Pro Asn
                85                  90                  95

Leu Ser Lys Ser Tyr Val Asn Asn Lys Glu Lys Glu Val Leu Val Leu
            100                 105                 110

Trp Gly Val His His Pro Pro Asn Ile Gly Asp Gln Arg Ala Leu Tyr
        115                 120                 125

His Thr Glu Asn Ala Tyr Val Ser Val Ser Ser His Tyr Ser Arg
    130                 135                 140

Arg Phe Thr Pro Glu Ile Ala Lys Arg Pro Lys Val Arg Asp Gln Glu
145                 150                 155                 160

Gly Arg Ile Asn Tyr Tyr Trp Thr Leu Leu Glu Pro Gly Asp Thr Ile
                165                 170                 175

Ile Phe Lys Ala Asn Gly Asn Leu Ile Ala Pro Trp Tyr Ala Phe Ala
            180                 185                 190

Leu Ser Arg Gly Phe Gly Ser Gly Ile Ile Thr Ser Asn Ala Pro Met
        195                 200                 205

Asp Glu Cys Asp Ala Lys Cys Gln Thr Pro Gln Gly Ala Ile Asn Ser
    210                 215                 220

Ser Leu Pro Phe Gln Asn Val His Pro Val Thr Ile Gly Glu Cys Pro
225                 230                 235                 240

Lys Tyr Val Arg Ser Ala Lys Leu Arg Met Val Thr Gly Leu Arg Asn
                245                 250                 255

```
Ile Pro Ser Ile Gln Ser Arg Gly Leu Phe Gly Ala Ile Ala Gly Phe
            260                 265                 270

Ile Glu Gly Gln Trp Thr Gly Met Val Asp Gly Trp Tyr Gly Tyr His
        275                 280                 285

His Gln Asn Glu Gln Gly Ser Gly Tyr Ala Ala Asp Gln Lys Ser Thr
    290                 295                 300

Gln Asn Ala Ile Asn Gly Ile Thr Asn Lys Val Asn Ser Val Ile Glu
305                 310                 315                 320

Lys Met Asn Thr Gln Phe Thr Ala Val Gly Lys Glu Phe Asn Lys Leu
                325                 330                 335

Glu Arg Arg Met Glu Asn Thr Leu Asn Lys Lys Val Asp Asp Gly Phe
            340                 345                 350

Leu Asp Ile Trp Thr Tyr Asn Ala Glu Leu Ile Val Leu Ile Glu Asn
        355                 360                 365

Glu Arg Thr Leu Asp Phe His Asp Ser Asn Val Glu Asn Leu Tyr Glu
    370                 375                 380

Lys Val Arg Ser Gln Leu Lys Asn Asn Ala Lys Glu Ile Gly Asn Gly
385                 390                 395                 400

Cys
```

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

```
Trp Leu Thr Gly Lys Asn Gly Leu
1               5
```

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

```
Arg Asn Leu Leu Trp Leu Thr Gly Lys Asn Gly Leu Tyr Pro Asn
1               5                   10                  15
```

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

```
Val Leu Leu Glu Asn Glu Arg Thr Leu
1               5
```

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

```
Glu Leu Leu Val Leu Leu Glu Asn Glu Arg Thr Leu Asp Phe His
1               5                   10                  15
```

METHODS AND COMPOSITION RELATED TO TH-1 DENDRITIC CELLS

CROSS-REFERENCE TO RELATED APPLICATIONS

This application is a continuation of co-pending U.S. patent application Ser. No. 13/132,517, filed Aug. 29, 2011, which is a national phase application under 35 U.S.C. §371 of International Application No. PCT/US2009/066807, filed Dec. 4, 2009, which claims priority to U.S. Patent Application Ser. No. 61/120,437, filed on Dec. 6, 2008. The entire text of each of the above-referenced disclosures is specifically incorporated herein by reference without disclaimer.

This invention was made with government support under grant 5R01 CA061508-13 awarded by the National Institutes of Health. The government has certain rights in the invention.

The sequence listing that is contained in the file named "UTSCP1019USC1_ST25.txt", which is 2 KB (as measured in Microsoft Windows®) and was created on Mar. 27, 2014, is filed herewith by electronic submission and is incorporated by reference herein.

BACKGROUND OF THE INVENTION

I. Field of the Invention

Embodiments of this invention are directed generally to biology, medicine, and immunotherapy. In certain aspects, the present invention relates to the generation of double-loaded (RNA loaded and antigen loaded) antigen presenting cells (APCs) and their use in immunotherapy.

II. Background

Dendritic cells are the master regulators of the adaptive immune response (Banchereau and Palucka, 2005; Banchereau et al., 2003; Hartgers et al., 2000; Steinman et al. 2003), and the development of a dendritic cell vaccine that can consistently eliminate minimal residual neoplastic disease remains an important goal in the field of tumor immunology. In the design of dendritic cell vaccines for active cancer immunotherapy, a variety of tumor-specific agents have been used as antigen sources including tumor lysates (Chang et al. 2002; Geiger et al., 2001; Nestle et al., 1998), preparations of tumor mRNA (Heiser et al., 2002; Nair et al., 2002; Morse et al., 1999; Gilboa and Vieweg 2004), tumor specific peptides (Banchereau et al., 2001; Toungouz et al., 2001; Tjoa et al., 1998), idiotype protein (for myeloma or lymphoma) (Timmerman et al., 2002; Titzer et al., 2000; Lim et al., 1999) and gene transfer vectors expressing tumor-specific antigens (Tozer et al., 2002; Haluska et al., 2000). Of these agents, both tumor lysates and mRNA preparations are attractive antigenic sources as each possesses a full complement of patient-specific tumor antigens; however, each of these agents is also associated with its own particular biological shortcoming. The use of mRNA as an antigen source alone does not provide exogenous material for CD4+ T-cell priming, the consequence of which could be tumor-specific T-cell lethargy rather than robust CTL priming (Tham et al., 2002; Behrens et al., 2004; Rocha and Tanchot, 2004). Correspondingly, the use of lysate as an antigen source alone does not load the classical MHC class I compartment and might not efficiently provide antigenic material for CD8+ T-cell priming. When lysate is used as an antigen source, the phenomenon of dendritic cell cross-presentation is cited as the principal mechanism by which exogenous antigens are presented by MHC class I. While cross-presentation clearly plays a bona fide role in the generation of tumor-specific CTL, recent reports now demonstrate that cross-presentation may be somewhat biased in vivo and, perhaps, a suboptimal substitute for genuine, endogenous class I presentation (Wolkers et al. 2004; Zinkernagel 2002; Ochsenbein et al., 2001).

There remains a need for additional dendritic cell vaccine methodology and compositions.

SUMMARY OF THE INVENTION

Therapeutic vaccination with dendritic cells presenting tumor-specific antigens is recognized as an important investigational therapy for the treatment of neoplastic disease. Dendritic cell cross-presentation is credited with the ability of tumor lysate-loaded dendritic cells to prime both CD4 and CD8-specific T-lymphocyte responses, enabling the generation of cancer specific CTL activity without the loading of the classical MHC class I compartment. Recently, however, several reports have raised doubts as to the efficiency of cross presentation as a mechanism—for—CTL priming in vivo. To examine this issue, human dendritic cells were doubly loaded with both AML-specific tumor lysate and AML-specific tumor mRNA. The results show that these doubly loaded dendritic cells can mediate superior primary, recall, and effector lytic responses in vitro in comparison to those of dendritic cells loaded with either tumor lysate or tumor mRNA alone. Enhanced recall responses appeared to be influenced by CD40/CD40L signaling, underscoring the importance of T-cell help in the generation and perpetuation of the adaptive immune response.

In the control of Th-1 polarization and generation of CD8+ responses, dendritic cells (DC) must interpret a complex array of stimuli, many of which are poorly understood. Here it is demonstrated that Th-1 polarization is heavily influenced by DC-autonomous phenomena triggered by the loading of DC with antigenically matched MHC class I and class II determinants, i.e., class I and II peptide epitopes exhibiting significant amino acid sequence overlap (such as would be physiologically present during infectious processes requiring Th-1 immunity for clearance). Data were derived from thirteen independent antigenic models including whole-cell systems, single protein systems, and three different pairs of overlapping class I and II binding epitopes. Once loaded with matched class I and II antigens, these "Th-1 DC" exhibited differential cytokine secretion and surface marker expression, a distinct transcriptional signature, and acquired the ability to enhance the generation of CD8+ T-lymphocytes. Mechanistically, tRNA-synthetases were implicated as components of a putative sensor complex involved in the comparison of class I and II epitopes. These data provide rigorous conceptual explanations for the process of Th-1 polarization and the antigenic specificity of cognate T-cell help, enhance the understanding of Th-1 responses, and should contribute to the formulation more effective vaccination strategies.

Certain embodiments of the invention are directed to methods for inducing an immunologic response to a tumor in a patient. Such methods can comprise one or more steps of (a) obtaining monocytic dendritic cell precursors from a patient; (b) culturing the monocytes with specific cytokines thereby inducing functional differentiation into immature dendritic cells; (c) differentiating the immature dendritic cells into mature dendritic cells by (i) transfecting into the immature dendritic cells a nucleic acid composition encoding one or more tumor antigens; and (ii) contacting the immature dendritic cells with a tumor antigen composition; (d) culturing the immature dendritic cells to produce mature dendritic cells; and (e) administering the mature dendritic cells to the patient. In certain aspects, a tumor antigen composition can comprise all or a fraction of a cell lysate and one or more isolated recombinant proteins or peptides. In a further aspect, a nucleic acid composition of the invention can include a nucleic acid fraction of a tumor or target cell and one or more recombinant expression vectors or RNA transcribe there from. This addition of other purified components is referred to herein as spiking a composition.

In certain aspects, the mature dendritic cells are selected for CD83 expression, wherein the selected mature dendritic cells are enriched for cells expressing increased levels of CD83 as compared to reference dendritic cells contacted with a tumor antigen composition and not a nucleic acid composition. CD83 (Cluster of Differentiation 83) is a human protein encoded by the CD83 gene and is illustrate in GenBank submissions NM_001040280 (mRNA) and NP_001035370 (protein). In a further aspect, CD83 expression is between 10% and 40% higher than the reference dendritic cells.

In other aspect the method can comprise selecting a cell population, cell type, nucleic acid population, cell fraction(s), and/or antigen population. The immature dendritic cells can subjected to negative and/or positive selection using an agent that binds a non-target dendritic or a target dendritic cell, respectively. The term "negative selection" refers to the elimination, removal, or reduction in amount of an undesirable or non-target component in a composition, such cells, RNA, or antigens. Positive selection refers to the retention, enrichment, or increase in the relative amount desirable or target component in a composition, such as cells, RNA, or antigens.

In a further aspect, the nucleic acid composition can comprise total nucleic acid from a tumor source, mRNA isolated from a tumor source (e.g., poly A RNA), or one or more isolated RNA or DNA. An isolated mRNA can be enriched for mRNA encoding tumor specific antigens. In certain aspects the isolated mRNA is subjected to mRNA subtraction using non-tumor RNA. Nucleic acids related to the invention can be amplified (e.g., U.S. Pat. No. 4,683,195, which is incorporated herein by reference in its entirety). Examples of subtraction techniques can be found in U.S. Pat. Nos. 5,032,502; 5,221,608; 5,436,142; 5,580,726; 5,589,339; 5,804,382; 6,107,023; 6,458,566; Travis et al. Proc. Natl. Acad. Sci. USA pp 1696-1700, 1988; and Clontech's PCR-Select cDNA Subtraction Kit (protocol number PT-1117-1), all of which are incorporated herein by reference in their entirety.

In still a further aspect, the methods include a tumor antigen composition that is an enriched tumor antigen composition. The enriched tumor antigen composition can comprise a cellular fraction from cells of a tumor source. In certain aspects the cells from the tumor source are selected by removing cells expressing proteins that are typically not expressed or expressed at significantly reduced levels in a tumor cell and/or cells from the tumor source are selected using cell surface markers preferentially expressed by tumor cells. The enriched tumor antigen composition can comprise one or more protein fractions of a tumor cell lysate. The enriched tumor antigen composition can be produced by contacting a tumor cell lysate with a protein array that preferentially binds non-tumor specific antigens or preferentially binds tumor specific antigens. Both of which may be used in a variety of combinations. Examples of such methods can be found at least in U.S. Pat. Nos. 4,859,464; 7,195,874; and 7,264,810; each of which is incorporated herein by reference.

In certain embodiments the nucleic acid composition comprises an expression construct. The expression construct encodes one or more tumor antigen. In certain aspect 1, 2, 3, 4, 5, 6, 7, 8, 9, 10 or more tumor antigens are selected from the group consisting of 707-AP=707 alanine proline; AFP=alpha (α)-fetoprotein; AIM-2=interferon-inducible protein absent in melanoma 2; ART-4=adenocarcinoma antigen recognized by T cells 4; BAGE=B antigen; Bcr-abl=breakpoint cluster region-Abelson; CAMEL=CTL-recognized antigen on melanoma; CAP-1=carcinoembryonic antigen peptide-1; CASP-8=caspase-8; CDC27=cell-division-cycle 27; CDK4=cyclin-dependent kinase 4; CEA=carcino-embryonic antigen; CLCA2=calcium-activated chloride channel-2; CT=cancer/testis (antigen); Cyp-B=cyclophilin B; DAM=differentiation antigen melanoma (DAM-6 and DAM-10); ELF2=elongation factor 2; Ep-CAM=epithelial cell adhesion molecule; EphA2, 3=Ephrin type-A receptor 2, 3; ETV6-AML1=Ets variant gene 6/acute myeloid leukemia 1 gene ETS; FGF-5=Fibroblast growth factor-5; FN=fibronectin; G250=glycoprotein 250; GAGE=G antigen; GnT-V=N-acetylglucosaminyltransferase V; Gp100=glycoprotein 100 kD; HAGE=helicase antigen; HER-2/neu=human epidermal receptor-2/neurological; HLA-A*0201-R170I=arginine (R) to isoleucine (I) exchange at residue 170 of the α-helix of the α2-domain in the HLA-A2 gene; HSP70-2M=heat shock protein 70-2 mutated; HST-2=human signet ring tumor-2; hTERT=human telomerase reverse transcriptase; iCE=intestinal carboxyl esterase; IL-13Rα2=interleukin 13 receptor α2 chain; KIAA0205; LAGE=L antigen; LDLR/FUT=low density lipid receptor/GDP-L-fucose: β-D-galactosidase 2-α-L-fucosyltransferase; MAGE=melanoma antigen; MART-1/Melan-A=melanoma antigen recognized by T cells-1/Melanoma antigen A; MART-2=melanoma Ag recognized by T cells-2; MC1R=melanocortin 1 receptor; M-CSF=macrophage colony-stimulating factor gene; MUC1, 2=mucin 1, 2; MUM-1, -2, -3=melanoma ubiquitous mutated 1, 2, 3; NA88-A=NA cDNA clone of patient M88; Neo-PAP=Neo-poly(A) polymerase; NPM/ALK=nucleophosmin/anaplastic lymphoma kinase fusion protein; NY-ESO-1=New York-esophageous 1; OA1=ocular albinism type 1 protein; OGT=O-linked N-acetylglucosamine transferase gene; OS-9; P15=protein 15; p190 minor bcr-abl=protein of 190 KD bcr-abl; Pml/RARα=promyelocytic leukemia/retinoic acid receptor α; PRAME=preferentially expressed antigen of melanoma; PSA=prostate-specific antigen; PSMA=prostate-specific membrane antigen; PTPRK=receptor-type protein-tyrosine phosphatase kappa; RAGE=renal antigen; RU1, 2=renal ubiquitous 1, 2; SAGE=sarcoma antigen; SART-1, -2, -3=squamous antigen rejecting tumor 1, 2, 3; SSX-2=synovial sarcoma, X breakpoint 2; Survivin-2B=intron 2-retaining survivin; SYT/SSX=synaptotagmin I/synovial sarcoma, X fusion protein; TEL/AML1=translocation Ets-family leukemia/acute myeloid leukemia 1; TGFβRII=transforming growth factor β receptor 2; TPI=triosephosphate isomerase; TRAG-3=taxol resistant associated protein 3; TRG=testin-related gene; TRP-1=tyrosinase related protein 1, or gp75; TRP-2=tyrosinase related protein 2; TRP-2/INT2=TRP-2/intron 2; TRP-2/6b=TRP-2/novel exon 6b; PAP=prostatic acid phosphatase; PR1=proteinase 3; tyrosinase, MAGE-3, GAGE-2, SCP-1, Hom/MeI-40, PRAME, p53, H-Ras, E2A-PRL, H4-RET, IGH-IGK, MYL-RAR, Epstein Barr virus antigens, EBNA, human papillomavirus (HPV) antigens E6 and E7, TSP-180, MAGE-3, MAGE-4, MAGE-5, MAGE-6, p185erbB2, p180erbB-3, c-met, mn-23H1, TAG-72-4, CA 19-9, CA 72-4, CAM 17.1, NuMa, K-ras, β-Catenin, p16, TAGE, PSCA, CT7, 43-9F, 5T4, 791Tgp72, β-HCG, BCA225, BTAA, CA 125, CA 15-3 (CA 27.29\BCAA), CA 195, CA 242, CA-50, CAM43, CD68\KP1, CO-029, HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, ING1, mamaglobin, cyclin B1, S100, BRCA1, BRCA2, epidermal growth factor receptor; and WT1=Wilms' tumor gene. In certain aspects, the method further comprising screening a patient or patient tumor for expression of one or more of these tumor antigens. An expression construct expressing an identified tumor antigen can then be transfected into an immature or mature dendritic cell. In certain aspects the immature dendritic cell is contacted with a tumor antigen composition comprising a recombinant identified tumor antigen.

In certain embodiments the nucleic acid composition encodes components of the tumor antigen composition.

In still other embodiments, the immature dendritic cells are transfected with the nucleic acid composition prior to contact with the tumor antigen composition, or the immature dendritic cells are contacted with the tumor antigen composition prior to transfection with the nucleic acid composition, or the immature dendritic cells are simultaneously transfected with the nucleic acid composition and contacted with the tumor antigen composition.

In certain aspects a tumor is a renal cell cancer, melanoma, prostate cancer or chronic lymphocytic leukemia, bladder, blood, bone, bone marrow, brain, breast, colon, esophagus, gastrointestine, gum, head, kidney, liver, lung, nasopharynx, neck, ovary, pancreas, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, RNA can be evaluated in pre-cancers, such as metaplasia, dysplasia, and hyperplasia.

In other aspects methods can be directed to inducing T-cell proliferation comprising: (a) obtaining T-cells from a patient; (b) obtaining immature dendritic cells from the patient; (c) culturing the immature dendritic cells; (d) differentiating the immature dendritic cells into mature dendritic cells by (i) transfecting into the immature dendritic cells a nucleic acid composition encoding one or more tumor antigens; and (ii) contacting the immature dendritic cells with a tumor antigen composition; (e) culturing the immature dendritic cells to produce mature [or conditioned] dendritic cells; and (f) contacting the T-cells with the mature dendritic cells.

Compositions of the invention include an isolated population of mature dendritic cells comprising mature dendritic cells selected for high level CD83 expression as compared to a reference level derived from a mature dendritic cell population exposed to tumor antigen alone. Cells can be isolated using flow cytometry and the like.

The isolated population of mature dendritic cells can be selected by expression of 1, 2, 3, 4, or more additional marker. The additional marker(s) include, but are not limited to CD83, CD40, IL-2β and TLR-4.

In still a further aspect, compositions of dendritic cells, wherein the dendritic cells (a) constitutively express the cell surface markers CD83 and CD40; (b) secrete the cytokine IL-12; and (c) upon antigenic stimulation with a cell lysate and RNA corresponding to the cell lysate.

Cell fractionation is the separation of homogeneous sets of compartments of organelles or cell components from a population of cells. Cell fraction can include, but is not limited to differential centrifugation, filtration, precipitation, chromatography (paper, column, ionic, size exclusion, affinity, etc.). Typically, cells are disrupted prior to fraction, disruption methods include homogenization, sonication, detergent lysis, mechanical shearing, freeze/thaw cycles and combinations thereof.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen that gives rise to a biological response is referred to herein as an "antigenic determinant." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Two possible models by which dendritic cells might compare the sequence similarity of MHC class I and class II antigens. FIG. 1A. tRNA synthetases (transparent blue) might bind directly to their cognate amino acid substrate (red circle), and identical synthetases might recognize each other by Watson-Crick base pairing between stem loop structures of their bound tRNAs (dotted red lines). This model might be compromised by steric considerations. FIG. 1B. tRNA synthetases in the lysosmal compartment mediate the covalent attachment of tRNAs to cognate amino acid residues of peptide epitopes loaded in MHC binding pockets. Identical epitopic sequences would then recognize each other directly by tRNA stem loop interactions without relying upon bulky synthetase enzymes. This model, in its current form, does not fit well with the known biochemistry of aminoacyl-tRNA synthetases. In either model, a critical threshold of aggregated tRNA molecules is hypothesized to attract an RNA-binding intermediary complex (transparent yellow) that triggers signaling through CD63. MHC class I and II binding pockets derived from Hertz and Yanover, 2006.

FIGS. 13A-B. A. Positioning of MHC class I and II peptides along the primary sequence of influenza HA antigen (SEQ ID NO: 3). B. Schematic representation of the class I/II overlapping peptide pair (B8-166 (SEQ ID NO: 4)/DR3-162 (SEQ ID NO: 5)), the sequence comparison of which is predicted to be disrupted by ethanolamine. The control class I/II overlapping peptide pair (A2-443 (SEQ ID NO: 6)/DR3-440 (SEQ ID NO: 7)) is predicted to be unaffected by the presence of ethanolamine.

FIGS. 14A-D. A system of overlapping/non-overlapping defined class I and II peptides demonstrates that enhanced $T_h$-1 responses mediated by DC are dependent upon sequence overlap of loaded class I and II antigenic epitopes. A. Full class I/II sequence overlap. Gray bar=IFN-γ release induced by DC loaded with overlapping class I and II peptides. White bars=IFN-γ release induced by DC loaded with non-overlapping class I and II peptides or singly-loaded DC. Y-axis=total IFN-γ release in square MM. B. Partial (5 residues) class I/II sequence overlap. C. Peptides defined as B8- and DR3-restricted elicit responses in an HLA-B8−/HLA-DRI31*03− background ($p<0.03$ in this representative experiment). D. DCs loaded with overlapping class I and II peptide epitopes support enhanced production of activated CD8+ cells ($p<0.0001$). Gray bars=Percent CD8+ CD25+ cells induced by DC loaded with overlapping class I and II peptides. White bars=Percent CD8+ CD25+ cells induced by singly-loaded DC. Black bar=average percent CD8+ CD25+ cells induced by all populations of singly-loaded DC. Y-axis=Percent CD8+ CD25+ cells.

FIGS. 15A-D. Treatment of DC with the glycyl-tRNA synthetase inhibitor ethanolamine inhibits $T_h$-1 responses induced by DC loaded with overlapping class I and II MHC binding peptides only when glycine residues are present in the class I/II sequence overlap region. A. Addition of ethanolamine reduced CD8+ production over 70% when DC were loaded with the glycine-containing B8-166/DR3-162 peptide pair. CD8+ production induced by the non-glycine containing peptide pair A2-443/DR3-440 was unaffected. Y-axis=Percent CD3+CD8+ cells. B. CD8+ production in the presence of ethanolamine shown as a percentage of CD8+ production in the absence of ethanolamine (normalized to 100%). Y-axis=Percent of control (no ethanolamine). C. Addition of ethanolamine reduced CD8+CD25+ production over 80% when DC were loaded with the glycine-containing B8-166/DR3-162 peptide pair. CD8+CD25+ production induced by the non-glycine containing peptide pair A2-443/DR3-440 was largely unaffected. Y-axis=Percent CD8+ CD25+ cells. D. Data normalized similarly as described above. Y-axis=Percent of control (no ethanolamine). All figures: White bars=T-cells stimulated by untreated DC. Gray bars=T-cells stimulated by ethanolamine-treated DC.

FIG. 16. PSP94 levels in individual mice.

FIG. 17. PSP94 levels in individual mice.

DETAILED DESCRIPTION OF THE INVENTION

A "dendritic cell" (DC) belongs to a group of cells called professional antigen presenting cells (APCs). DCs have a characteristic morphology, with thin sheets (lamellipodia) extending from the dendritic cell body in several directions. Several phenotypic criteria are also typical, but can vary depending on the source of the dendritic cell. These include high levels of MHC molecules (e.g., class I and class II MHC) and costimulatory molecules (e.g., B7-1 and B7-2), and a lack of markers specific for granulocytes, NK cells, B cells, and T cells. Many dendritic cells express certain markers; for example, some Human dendritic cells selectively express CD83, a member of the immunoglobulin superfamily (Zhou and Tedder (1995) Journal of Immunology 3821-3835). Dendritic cells are able to initiate primary T cell responses in vitro and in vivo. These responses are antigen specific. Dendritic cells direct a strong mixed leukocyte reaction (MLR) compared to peripheral blood leukocytes, splenocytes, B cells and monocytes. Dendritic cells are optionally characterized by the pattern of cytokine expression by the cell (Zhou and Tedder (1995) Blood 3295-3301). DCs can be generated in vivo or in vitro from immature precursors (e.g., monocytes).

I. $T_h$-1 Dendritic Cells

Figure 2:
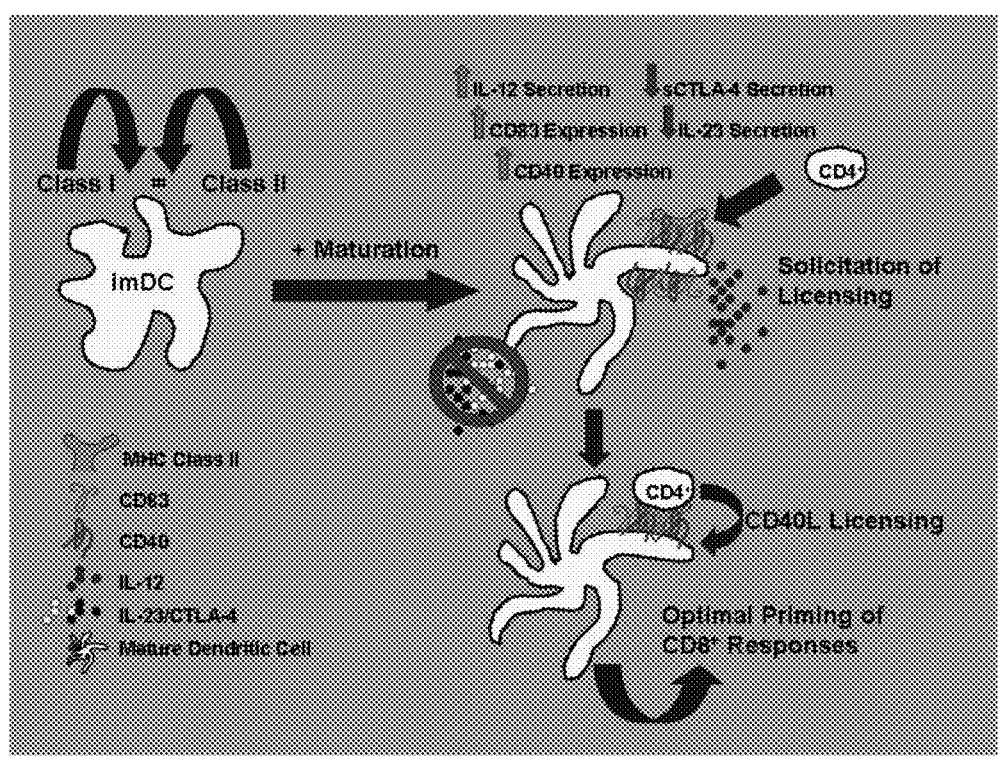
FIG. 2. Solicitation of CD4 licensing by $T_h$-1 dendritic cells.

Methods for isolating cell populations enriched for dendritic cell precursors and immature dendritic cells from various sources, including blood and bone marrow, are known in the art. For example, dendritic cell precursors and immature dendritic cells can be isolated by collecting heparinized blood, by apheresis or leukapheresis, by preparation of buffy coats, rosetting, centrifugation, density gradient centrifugation (e.g., using Ficoll (such as FICOLL-PAQUE®), PERCOLL® (colloidal silica particles (15-30 mm diameter) coated with non-dialyzable polyvinylpyrrolidone (PVP)), sucrose, and the like), differential lysis of cells, filtration, and the like. In certain embodiments, a leukocyte population can be prepared, such as, for example, by collecting blood from a subject, defribrinating to remove the platelets and lysing the red blood cells. Dendritic cell precursors and immature dendritic cells can optionally be enriched for monocytic dendritic cell precursors by, for example, centrifugation through a PERCOLL® gradient. In other aspects, dendritic cell precursors can be selected using CD14 selection of G-CSF mobilized peripheral blood.

Dendritic cell precursors and immature dendritic cells optionally can be prepared in a closed, aseptic system. As used herein, the terms "closed, aseptic system" or "closed system" refer to a system in which exposure to non-sterilize, ambient, or circulating air or other non-sterile conditions is minimized or eliminated. Closed systems for isolating dendritic cell precursors and immature dendritic cells generally exclude density gradient centrifugation in open top tubes, open air transfer of cells, culture of cells in tissue culture plates or unsealed flasks, and the like. In a typical embodiment, the closed system allows aseptic transfer of the dendritic cell precursors and immature dendritic cells from an initial collection vessel to a sealable tissue culture vessel without exposure to non-sterile air.

In certain embodiments, monocytic dendritic cell precursors are isolated by adherence to a monocyte-binding substrate. For example, a population of leukocytes (e.g., isolated by leukapheresis) can be contacted with a monocytic dendritic cell precursor adhering substrate. When the population of leukocytes is contacted with the substrate, the monocytic dendritic cell precursors in the leukocyte population preferentially adhere to the substrate. Other leukocytes (including other potential dendritic cell precursors) exhibit reduced binding affinity to the substrate, thereby allowing the monocytic dendritic cell precursors to be preferentially enriched on the surface of the substrate.

Suitable substrates include, for example, those having a large surface area to volume ratio. Such substrates can be, for example, a particulate or fibrous substrate. Suitable particulate substrates include, for example, glass particles, plastic particles, glass-coated plastic particles, glass-coated polystyrene particles, and other beads suitable for protein absorption. Suitable fibrous substrates include microcapillary tubes and microvillous membrane. The particulate or fibrous substrate usually allows the adhered monocytic dendritic cell precursors to be eluted without substantially reducing the viability of the adhered cells. A particulate or fibrous substrate can be substantially non-porous to facilitate elution of monocytic dendritic cell precursors or dendritic cells from the substrate. A "substantially non-porous" substrate is a substrate in which at least a majority of pores present in the substrate are smaller than the cells to minimize entrapping cells in the substrate.

Adherence of the monocytic dendritic cell precursors to the substrate can optionally be enhanced by addition of binding media. Suitable binding media include monocytic dendritic cell precursor culture media (e.g., AIM-V®, RPMI 1640, DMEM, X-VIVO 15®, and the like) supplemented, individually or in any combination, with for example, cytokines (e.g., Granulocyte/Macrophage Colony Stimulating Factor (GM-CSF), Interleukin 4 (IL-4), or Interleukin 13 (IL-13)), blood plasma, serum (e.g., human serum, such as autologous or allogenic sera), purified proteins, such as serum albumin, divalent cations (e.g., calcium and/or magnesium ions) and other molecules that aid in the specific adherence of monocytic dendritic cell precursors to the substrate, or that prevent adherence of non-monocytic dendritic cell precursors to the substrate. In certain embodiments, the blood plasma or serum can be heated-inactivated. The heat-inactivated plasma can be autologous or heterologous to the leukocytes.

Following adherence of monocytic dendritic cell precursors to the substrate, the non-adhering leukocytes are separated from the monocytic dendritic cell precursor/substrate complexes. Any suitable means can be used to separate the non-adhering cells from the complexes. For example, the mixture of the non-adhering leukocytes and the complexes can be allowed to settle, and the non-adhering leukocytes and media decanted or drained. Alternatively, the mixture can be centrifuged, and the supernatant containing the non-adhering leukocytes decanted or drained from the pelleted complexes.

Isolated dendritic cell precursors can be cultured ex vivo for differentiation, maturation and/or expansion. (As used herein, isolated immature dendritic cells, dendritic cell precursors, T cells, and other cells, refers to cells that, by human hand, exists apart from their native environment, and are therefore not a product of nature. Isolated cells can exist in purified form, in semi-purified form, or in a non-native environment.) Briefly, ex vivo differentiation typically involves culturing dendritic cell precursors, or populations of cells having dendritic cell precursors, in the presence of one or more differentiation agents. Suitable differentiating agents can be, for example, cellular growth factors (e.g., cytokines such as (GM-CSF), Interleukin 4 (IL-4), Interleukin 13 (IL-13), and/or combinations thereof). In certain embodiments, the monocytic dendritic cells precursors are differentiated to form monocyte-derived immature dendritic cells.

The dendritic cell precursors can be cultured and differentiated in suitable culture conditions. Suitable tissue culture media include AIM-V®, RPMI 1640, DMEM, X-VIVO 15®, and the like. The tissue culture media can be supplemented with serum, amino acids, vitamins, cytokines, such as GM-CSF and/or IL-4, divalent cations, and the like, to promote differentiation of the cells. In certain embodiments, the dendritic cell precursors can be cultured in the serum-free media. Such culture conditions can optionally exclude any animal-derived products. A typical cytokine combination in a typical dendritic cell culture medium is about 500 units/ml each of GM-CSF (50 ng/ml) and IL-4 (10 ng/ml). Dendritic cell precursors, when differentiated to form immature dendritic cells, are phenotypically similar to skin Langerhans cells. Immature dendritic cells typically are $CD14^-$ and $CD11c^+$, express low levels of CD86 and CD83, and are able to capture soluble antigens via specialized endocytosis. The immature DC expressed very high levels of CD86. Also, the population was mixed in terms of CD14 and CD11C. Though the majority were CD11c+, there were distinct subpopulations that were CD11c− and CD14+.

The immature dendritic cells are matured to form mature dendritic cells. Mature DC lose the ability to take up antigen and display up-regulated expression of costimulatory cell surface molecules and various cytokines. Specifically, mature DC express higher levels of MHC class I and II antigens than immature dendritic cells, and mature dendritic cells are generally identified as being CD80+, CD83+, CD86+, and CD14−. Greater MHC expression leads to an increase in antigen density on the DC surface, while up regulation of costimulatory molecules CD80 and CD86 strengthens the T cell activation signal through the counterparts of the costimulatory molecules, such as CD28 on the T cells.

Mature dendritic cells of the present invention can be prepared (i.e., matured) by contacting the immature dendritic cells with effective amounts or concentrations of a nucleic acid composition and a tumor antigen composition. Effective amounts of nucleic acid composition typically range from at most, at least, or about 0.01, 0.1, 1, 5, 10, to 10, 15, 20, 50, 100 ng or mg of nucleic acid per culture dish or per cell, including all values and ranges there between. Effective amounts of tumor antigen composition typically range from at most, at least, or about 0.01, 0.1, 1, 5, 10, to 10, 15, 20, 50, 100 ng or mg of protein per culture dish or per cell. In certain aspects 0.001 ng of tumor antigen/cell to 1 µg of tumor antigen/million cells) can be used. The tumor antigen composition can optionally be heat inactivated or treated (e.g., exposed to protease) prior to contact with dendritic cells. Maturing the immature dendritic cells with a nucleic acid composition and a tumor antigen composition primes the mature dendritic cells for a type 1 (Th-1) response.

The immature DC are typically contacted with effective amounts of a nucleic acid composition and a tumor antigen composition for at most, at least, or about 1, 2, 3, 4, 5, 6, 7, 8, 9, 10, 11, 12, to 10, 11, 12, 13, 14, 15, 16, 17, 18, 19, 20, 21, 22, 23, or 24 minutes, hours, or days. The immature dendritic cells can be cultured and matured in suitable maturation culture conditions. Suitable tissue culture media include AIM-V®, RPMI 1640, DMEM, X-VIVO 15®, and the like. The tissue culture media can be supplemented with amino acids, vitamins, cytokines, such as GM-CSF and/or IL-4, divalent cations, and the like, to promote maturation of the cells.

Maturation of dendritic cells can be monitored by methods known in the art. Cell surface markers can be detected in assays familiar to the art, such as flow cytometry, immunohistochemistry, and the like. The cells can also be monitored for cytokine production (e.g., by ELISA, FACS, or other immune assay). Dendritic cell precursors, immature dendritic cells, and mature dendritic cells, either primed or unprimed, with antigens can be cryopreserved for use at a later date. Methods for cryopreservation are well-known in the art. For example, U.S. Pat. No. 5,788,963, which is incorporated herein by reference in its entirety.

A. Tumor Antigen Composition

A tumor antigen composition can comprise tumor cell lysate, including both tumor cells removed from a patient and/or tumor cells grown in primary culture or cell line culture; and/or at least one recombinantly expressed protein or peptide. The tumor antigen composition can be a full lysate or a lysate that has been purified or processed as is well known in the art. In certain aspects the tumor antigen is a fully or partially purified recombinant protein(s) or peptide(s). In certain embodiments a tumor antigen composition contains both a tumor lysate and a recombinant protein or peptide component. This combination tumor antigen composition increases the prevalence of certain known tumor antigens or other proteins or peptides that enhance the effectiveness of the methods and compositions described herein.

In certain embodiments, the tumor lysate can be prepared from surgically resected tumor tissue. Isolated tumor tissue can be minced and placed into a container with a buffer solution containing a proteinase (e.g., collagenase) to dissociate the tissue, producing liberated tumor cells. Following filtering of the tissue digest, liberated tumor cells can be centrifuged into a pellet. The cell pellet can then be suspended in a small volume of culture medium and subjected to cell disruption methods such as sonication or freeze-thaw cycles. After disruption, the tumor lysate can be, optionally, clarified by centrifugation and the protein containing supernatant can filtered for sterilization or otherwise processed.

Tumor antigens that can be produced recombinantly include, but are not limited to 707-AP=707 alanine proline; AFP=alpha (α)-fetoprotein; AIM-2=interferon-inducible protein absent in melanoma 2; ART-4=adenocarcinoma antigen recognized by T cells 4; BAGE=B antigen; Bcr-abl=breakpoint cluster region-Abelson; CAMEL=CTL-recognized antigen on melanoma; CAP-1=carcinoembryonic antigen peptide-1; CASP-8=caspase-8; CDC27=cell-division-cycle 27; CDK4=cyclin-dependent kinase 4; CEA=carcino-embryonic antigen; CLCA2=calcium-activated chloride channel-2; CT=cancer/testis (antigen); Cyp-B=cyclophilin B; DAM=differentiation antigen melanoma (DAM-6 and DAM-10); ELF2=elongation factor 2; Ep-CAM=epithelial cell adhesion molecule; EphA2, 3=Ephrin type-A receptor 2, 3; ETV6-AML1=Ets variant gene 6/acute myeloid leukemia 1 gene ETS; FGF-5=Fibroblast growth factor-5; FN=fibronectin; G250=glycoprotein 250; GAGE=G antigen; GnT-V=N-acetylglucosaminyltransferase V; Gp100=glycoprotein 100 kD; HAGE=helicase antigen; HER-2/neu=human epidermal receptor-2/neurological; HLA-A*0201-R170I=arginine (R) to isoleucine (I) exchange at residue 170 of the α-helix of the α2-domain in the HLA-A2 gene; HSP70-2M=heat shock protein 70-2 mutated; HST-2=human signet ring tumor-2; hTERT=human telomerase reverse transcriptase; iCE=intestinal carboxyl esterase; IL-13Rα2=interleukin 13 receptor α2 chain; KIAA0205; LAGE=L antigen; LDLR/FUT=low density lipid receptor/GDP-L-fucose: β-D-galactosidase 2-α-L-fucosyltransferase; MAGE=melanoma antigen; MART-1/Melan-A=melanoma antigen recognized by T cells-1/Melanoma antigen A; MART-2=melanoma Ag recognized by T cells-2; MC1R=melanocortin 1 receptor; M-CSF=macrophage colony-stimulating factor gene; MUC1, 2=mucin 1, 2; MUM-1, -2, -3=melanoma ubiquitous mutated 1, 2, 3; NA88-A=NA cDNA clone of patient M88; Neo-PAP=Neo-poly(A) polymerase; NPM/ALK=nucleophosmin/anaplastic lymphoma kinase fusion protein; NY-ESO-1=New York-esophageous 1; OA1=ocular albinism type 1 protein; OGT=O-linked N-acetylglucosamine transferase gene; OS-9; P15=protein 15; p190 minor bcr-abl=protein of 190 KD bcr-abl; Pml/RARa=promyelocytic leukemia/retinoic acid receptor α; PRAME=preferentially expressed antigen of melanoma; PSA=prostate-specific antigen; PSMA=prostate-specific membrane antigen; PTPRK=receptor-type protein-tyrosine phosphatase kappa; RAGE=renal antigen; RU1, 2=renal ubiquitous 1, 2; SAGE=sarcoma antigen; SART-1, -2, -3=squamous antigen rejecting tumor 1, 2, 3; SSX-2=synovial sarcoma, X breakpoint 2; Survivin-2B=intron 2-retaining survivin; SYT/SSX=synaptotagmin I/synovial sarcoma, X fusion protein; TEL/AML1=translocation Ets-family leukemia/acute myeloid leukemia 1; TGFβRII=transforming growth factor β receptor 2; TPI=triosephosphate isomerase; TRAG-3=taxol resistant associated protein 3; TRG=testin-related gene; TRP-1=tyrosinase related protein 1, or gp75; TRP-2=tyrosinase related protein 2; TRP-2/INT2=TRP-2/intron 2; TRP-2/6b=TRP-2/novel exon 6b; PAP=prostatic acid phosphatase; PR1=proteinase 3; tyrosinase, MAGE-3, GAGE-2, SCP-1, Hom/Mel-40, PRAME, p53, H-Ras, E2A-

PRL, H4-RET, IGH-IGK, MYL-RAR, Epstein Barr virus antigens, EBNA, human papillomavirus (HPV) antigens E6 and E7, TSP-180, MAGE-3, MAGE-4, MAGE-6, p185erbB2, p180erbB-3, c-met, mn-23H1, TAG-72-4, CA 19-9, CA 72-4, CAM 17.1, NuMa, K-ras, β-Catenin, p16, TAGE, PSCA, CT7, 43-9F, 5T4, 791Tgp72, β-HCG, BCA225, BTAA, CA 125, CA 15-3 (CA 27.29\BCAA), CA 195, CA 242, CA-50, CAM43, CD68\KP1, CO-029, HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, ING1, mamaglobin, cyclin B1, S100, BRCA1, BRCA2, epidermal growth factor receptor; and WT1=Wilms' tumor gene.

Various cells lines can be used to prepare tumor antigen compositions as well as nucleic acid compositions of the invention. These cell lines include, but are not limited to J82, RT4, ScaBER T24, TCCSUP 5637, SK-N-MC, SK-N-SH, SW 1088, SW 1783, U-87 MG, U-118 MG, U-138 MG, U-373 MG Y79, BT-20, BT-474, MCF7, MDA-MB-134-V, MDA-MD-157, MDA-MB-175-VII, MDA-MB-361, SK-BR-3, C-33 A, HT-3, ME-180, MEL-175, MEL-290, HLA-A*0201, MS751, SiHa, JEG-3, Caco-2, HT-29, SK-CO-1, HuTu 80, A-253, FaDu, A-498, A-704, Caki-1, Caki-2, SK-NEP-1, SW 839, SK-HE-1, A-427, Calu-1, Calu-3, Calu-6, SK-LU-1, SK-MES-1, SW 90, EB1, EB2, P3 HR-1, HT-144, Malme-3M, RPMI-7951, SK-MEL-1, SK-MEL-2, SK-MEL-3, SK-MEL-5, SK-MEL-24, SK-MEL-28, SK-MEL-31, Caov-3, Caov-4, SK-OV-3, SW 626, Capan-1, Capan-2, DU 145, A-204, Saos-2, SK-ES-1, SK-LNS-1, SW 684, SW 872, SW 982, SW 1353, U-2 OS, Malme-3, KATO III, Cate-1B, Tera-1, Tera-2, SW579, AN3 CA, HEC-1-A, HEC-1-B, SK-UT-1, SK-UT-1B, Sk-Me128, SW 954, SW 962, NCI-H69, NCI-H128, BT-483, BT-549, DU4475, HBL-100, Hs 578Bst, Hs 578T, MDA-MB-330, MDA-MB-415, MDA-MB-4355, MDA-MB-436, MDA-MB-453, MDA-MB-468 T-47D, Hs 766T, Hs 746T, Hs 695T, Hs 683, Hs 294T, Hs 602, JAR, Hs 445, Hs 700T, H4, Hs 696, Hs 913T, Hs 729, FHs 738Lu, FHs 173We, FHs 738B1, NIH:OVCAR-3, Hs 67, RD-ES, ChaGo K-1, WERI-Rb-1, NCI-H446, NCI-H209, NCI-H146, NCI-H441, NCI-H82 H9, NCI-H460, NCI-H596, NCI-H676B, NCI-H345, NCI-H820, NCI-H520, NCI-H661, NCI-H510A, D283 Med, Daoy, D341 Med, AML-193, and MV4-11.

B. Nucleic Acid Composition

Nucleic acids of the invention can comprise tumor derived nucleic acids and/or recombinant nucleic acids encoding one or more proteins or peptides associated or induce an immune response that is effective against a tumor or tumor cell. In certain embodiments a nucleic acid composition contains both a tumor derived nucleic acid population and a recombinant nucleic acid component. This combination nucleic acid composition increases the prevalence of certain known tumor antigens or other nucleic acids encoding proteins or peptides that enhance the effectiveness of the methods and compositions described herein.

A nucleic acid or nucleic acid primed dendritic cell is a dendritic cell that was incubated or transfected with RNA, e.g., RNA derived from a tumor or tumor cell. Such RNA can be transfected using conventional nucleic acid transfection methods, such as lipid-mediated transfection, electroporation, and calcium phosphate transfection. For example, RNA can be introduced into a DC by incubating the DC with the RNA (or extract) for 1 to 24 hours (e.g., 2 hours) at 37° C.

A "tumor-derived" nucleic acid refers to a nucleic acid that has its origin in a tumor cell, and which includes RNA corresponding to a tumor antigen(s). Included is RNA that encodes all or a portion of a tumor antigen or a previously identified tumor antigen. Such nucleic acid can be "in vitro transcribed," e.g., reverse transcribed to produce cDNA that can be amplified by PCR and subsequently be transcribed in vitro, with or without cloning the cDNA. Also included is RNA that is provided as a fractionated preparation of tumor cell. Because even unfractionated RNA preparation (e.g., total RNA or total poly A RNA) can be used, it is not necessary that a tumor antigen be identified. In one embodiment, the preparation is fractionated with respect to a non-RNA component(s) of the cell in order to decrease the concentration of a non-RNA component, such as protein, lipid, and/or DNA and enrich the preparation for RNA. If desired, the preparation can be further fractionated with respect to the RNA (e.g., by subtractive hybridization) such that "tumor-specific" or "pathogen-specific" RNA is produced.

By "tumor-specific" RNA is meant an RNA sample that, relative to unfractionated tumor-derived RNA, has a high content of RNA that is preferentially present in a tumor cell compared with a non-tumor cell. For example, tumor-specific RNA includes RNA that is present in a tumor cell, but not present in a non-tumor cell. Also encompassed in this definition is an RNA sample that includes RNA that is present both in tumor and non-tumor cells, but is present at a higher level in tumor cells than in non-tumor cells. Also included within this definition is RNA that encodes a previously identified tumor antigen and which is produced in vitro, e.g., from a plasmid or by PCR. Alternatively, tumor-specific RNA can be prepared by fractionating an RNA sample such that the percentage of RNA corresponding to a tumor antigen is increased, relative to unfractionated tumor-derived RNA. For example, tumor-specific RNA can be prepared by fractionating tumor-derived RNA using conventional subtractive hybridization techniques against RNA from non-tumor cells.

A variety of methods are suitable for producing the tumor-derived nucleic acid or RNA that can be used in the invention. It is not necessary that the nucleic acid be provided to the DC in a purified form. Preferably, the RNA sample (i.e., the fractionated tumor preparation) is at least 50%, more preferably 75%, 90%, or even 99% RNA (wt/vol). In practicing the invention, dendritic cells and their precursors are used. Such cells can be isolated according to previously-described procedures.

Any of a variety of methods can be used to produce nucleic acid compositions of the invention. For example, tumor preparations can be produced by sonicating tumor cells in a mammalian cell culture medium such as Opti-MEM or a buffer such as phosphate buffered saline. Other methods for disrupting cells also are suitable, provided that the method does not completely degrade the tumor-derived RNA. Typically, the RNA preparation has $10^6$ to $10^8$ cells/ml; most preferably $10^7$ cells/ml. As alternatives, or in addition, to sonication, the tumor-derived nucleic acid can be prepared by employing conventional RNA purification methods such as guanidinium isothiocyanate methods and/or oligo dT chromatography methods for isolating poly A RNA. RNA, synthesized according to conventional methods, can be used in lieu of RNA in tumor preparations. For example, RNA from a tumor can be reverse transcribed into cDNA, which then is amplified by conventional PCR techniques to provide an essentially unlimited supply of cDNA corresponding to the tumor or pathogen RNA antigen. Conventional in vitro transcription techniques and bacterial polymerases then are used to produce RNA. As an alternative, RNA can be synthesized from a cloned DNA sequence encoding a tumor polypeptide antigen. Methods for identifying such antigens are known in the art; for example, several melanoma peptide antigens have been identified. RNA transcribed in vitro from cDNA encoding identified peptide antigens can serve as tumor-specific RNA in the invention. As an alternative, RNA can be transcribed from "minigenes" consisting of a portion of the tumor antigen cDNA that encodes an epitope. Tumor-specific RNA can also be produced by employing conventional techniques for subtractive hybridization. For example, an RNA sample from tumor cells and non-tumor cells can be used in the subtractive hybridization method to obtain tumor-specific RNA.

Art-known transfection methods are suitable for introducing the tumor-derived nucleic acid into a dendritic cell. For example, 5-50 µg of RNA in 500 µl of Opti-MEM can be mixed with a cationic lipid at a concentration of 10 to 100 µg, and incubated at room temperature for 20 to 30 minutes. Other suitable lipids include LIPOFECTIN™ (1:1 (w/w) DOTMA:DOPE), LIPOFECTAMINE™ (3:1 (w/w) DOSPA:DOPE), DODAC:DOPE (1:1), CHOL:DOPE (1:1), DMEDA, CHOL, DDAB, DMEDA, DODAC, DOPE, DOR1, DORIE, DOSPA, DOTAP, and DOTMA. The resulting RNA-lipid complex is then added to $1\text{-}3\times10^6$ cells, preferably $2\times10^6$, antigen-presenting cells in a total volume of approximately 2 ml (e.g., in Opti-MEM), and incubated at 37° C. for 2 to 4 hours. Alternatively, the RNA can be introduced into the antigen presenting cells by employing conventional techniques, such as electroporation or calcium phosphate transfection with $1\text{-}5\times10^6$ cells and 5 to 50 µg of RNA. Typically, 5-20 µg of poly A RNA or 25-50 µg of total RNA are typically used.

When the RNA is provided as a tumor preparation, the preparation typically is fractionated or otherwise treated to decrease the concentration of proteins, lipids, and/or DNA in the preparation, and enrich the preparation for RNA. For example, art-known RNA purification methods can be used to at least partially purify the RNA from the tumor cell or pathogen. It is also acceptable to treat the RNA preparation with proteases or RNase-free DNases.

The nucleic acid-loaded antigen-presenting cells of the invention can be used to stimulate CTL proliferation in vivo or ex vivo. The ability of the nucleic acid-loaded dendritic cells to stimulate a CTL response can be measured by assaying the ability of the effector cells to lyse target cells. For example, the commonly-used europium release assay can be used. Typically, $5\text{-}10\times10^6$ target cells are labeled with europium diethylenetriamine pentaacetate for 20 minutes at 4° C. After several washes $10^4$ europium-labeled target cells and serial dilutions of effector cells at an effector:target ratio ranging from 50:1 to 6.25:1 are incubated in 200 µl RPMI 1640 with 10% heat-inactivated fetal calf serum in 96-well plates. The plates are centrifuged at 500×g for 3 minutes and the incubated at 37° C. in 5% $CO_2$ for 4 hours. A 50 µl aliquot of the supernatant is collected, and europium release is measured by time resolved fluorescence (Volgmann et al., J. Immunol. Methods 119:45-51, 1989).

C. Loading

Dendritic cells can be loaded under conditions and amounts of a tumor antigen composition, processed tumor cells, tumor cell debris, processed tumor antigens, processed tumor cells, processed cultured tumor cells and/or antigens that are needed to load the MHC of a dendritic cell. As used herein, the term "suitable" for antigen loading are those conditions that permit a DC to contact, process and present one or more tumor antigens on MHC, whether intracellular or on the cell surface. Based on the present disclosure and the examples herein, the skilled artisan will know the incubation, temperature and time period sufficient to allow effective binding, processing and loading. Incubation steps are typically from between about 1 to 2 to 4 hours, at temperatures of between about 25° to 37° C. (or higher) and/or may be overnight at about 4° C. and the like.

D. Culture

Activation of dendritic cells initiates the process that converts immature DCs, which are phenotypically similar to skin Langerhans cells, to mature, antigen presenting cells that can migrate to the lymph nodes. This process results in the gradual and progressive loss of the powerful antigen uptake capacity that characterizes the immature dendritic cell, and in the up-regulation of expression of co-stimulatory cell surface molecules and various cytokines. Various stimuli can initiate the maturation of DCs. One other consequence of maturation is a change in the in vivo migratory properties of the cells. For example, maturation induces several chemokine receptors, including CCR7, which direct the cells to the T cell regions of draining lymph nodes, where the mature DCs activate T cells against the antigens presented on the DC surface in the context of class I and class II MHC molecules. The terms "activation" and "maturation", and "activated" and "mature" describe the process of inducing and completing the transition from an immature DC (partially characterized by the ability to take up antigen) to a mature DC (partially characterized by the ability to effectively stimulate de novo T cell responses). The terms typically are used interchangeably in the art.

Known maturation protocols are based on the in vivo environment that DCs are believed to encounter during or after exposure to antigens. The best example of this approach is the use of monocyte conditioned media (MCM) as a cell culture medium. MCM is generated in vitro by culturing monocytes and used as a source of maturation factors, See, US 2002/0160430, incorporated herein by reference. The major components in MCM responsible for maturation are reported to be the (pro)inflammatory cytokines Interleukin 1 beta (IL-1β), Interleukin 6 (IL-6) and tumor necrosis factor alpha (TNFα).

Maturation of DCs therefore can be triggered by a multitude of different factors that act via a host of signal transduction pathways. Consequently, there is no single maturation pathway or outcome, but there exists in fact a universe of mature DC stages, each with their own distinct functional characteristics. Conceptually this makes sense because the various threats to the body that the immune system must respond to are manifold, requiring different attack strategies. As an example, while bacterial infection is best cleared by activated macrophages supplemented with specific antibodies, a viral infection is best attacked through cytotoxic T cells that effectively kill virus-infected cells. The killing of cancer cells typically involves a combination of cytotoxic T cells, natural killer cells, and antibodies.

In vitro maturation of DCs can therefore be designed to induce the immune system to favor one type of immune response over another, i.e., to polarize the immune response. Directional maturation of DCs describes the notion that the outcome of the maturation process dictates the type of ensuing immune response that results from treatment with the matured DCs. In its simplest form, directional maturation results in a DC population that produces cytokines that direct a T cell response polarized to either a $T_h1$-type or $T_h2$-type response. DCs express up to nine different Toll-like receptors (TLR1 through TLR9), each of which can be used to trigger maturation. Addition of interferon gamma (IFN-γ) to most maturation protocols results in the production of interleukin 12 by the mature DCs, which dictates a $T_h1$-type response. Conversely, inclusion of prostaglandin E2 has the opposite effect.

Factors that can be used in the directional maturation of activated DCs can therefore include for example, Interleukin 1 beta (IL-β), Interleukin 6 (IL-6), and tumor necrosis factor alpha (TNFα). Other maturation factors include prostaglandin E2 (PGE2), poly-dIdC, vasointestinal peptide (VIP), bacterial lipopolysaccharide (LPS), as well as mycobacteria or components of mycobacteria, such as specific cell wall constituents. Additional maturation factors include for example, an imidazoquinoline compound, e.g., R848 (WO 00/47719, incorporated herein by reference in its entirety), a synthetic double stranded polyribonucleotide, agonists of a Toll-like receptor (TLR), such as TLR3, TLR4, TLR7 and/or TLR9, a sequence of nucleic acids containing unmethylated CpG motifs known to induce the maturation of DC, and the like. Further, a combination of any of the above agents can be used in inducing the maturation of dendritic precursor cells.

Fully mature dendritic cells differ qualitatively and quantitatively from immature DCs. Once fully mature, DCs express higher levels of MHC class I and class II antigens, and higher levels of T cell costimulatory molecules, i.e., CD80 and CD86. These changes increase the capacity of the dendritic cells to activate T cells because they increase antigen density on the cell surface, as well as the magnitude of the T cell activation signal through the counterparts of the costimulatory molecules on the T cells, e.g., CD28 and the like. In addition, mature DCs produce large amounts of cytokines, which stimulate and polarize the T cell response.

Generally methods for ex vivo DC generation comprise obtaining a cell population enriched for DC precursor cells from a patient and then differentiating the DC precursor cells in vitro into mature DCs prior to introduction back into the patient. Typically, to generate immature dendritic cells (DC), one must first purify or enrich the monocytic precursors from other contaminating cell types. This is commonly done through adherence of the monocytic precursors to a plastic (polystyrene) surface, as the monocytes have a greater tendency to stick to plastic than other cells found in, for example, peripheral blood, such as lymphocytes and natural killer (NK) cells. After substantially removing the contaminating cells by vigorous washing, the monocytes are cultured with cytokines that convert the monocytic precursors to either immature DC or directly to mature DC. Methods for differentiating the monocytic precursor cells to immature DC were first described by Sallusto and Lanzavecchia (J. Exp. Med., 179: 1109-1118, 1994, incorporated herein by reference), who used the cytokines GM-CSF and IL-4 to induce the differentiation of the monocytes to immature DC. While this combination of cytokines is most typically used, various other combinations have been described to accomplish the same goals, such as replacing IL-4 with IL-13 or IL-15. The end result of this process is a "veiled" cell, which expresses T cell costimulatory molecules, as well as high levels of molecules of the major histocompatibility complex (MHC), but does not express the dendritic cell maturation marker CD83. These cells are similar to Langerhans cells in the skin, and their prime physiological function is to capture invading microorganisms.

Variations on this method include different methods of purifying monocytes, including, for example, tangential flow filtration (TFF), or by binding antibodies attached to beads to surface molecules on the monocytes. The beads with the bound cells are then concentrated in a column, or on a magnetic surface, such that contaminating cells can be washed away, after which the monocytes are eluted off the beads. In yet another method to obtain dendritic cells precursors, cells expressing the stem cell marker CD34, either from blood (U.S. Pat. No. 5,994,126, incorporated herein by reference) or from the bone marrow are purified. These cells can be cultured with the essential cytokine GM-CSF to differentiate into immature DC. These DC apparently have very similar characteristics and functional properties as immature DC generated from monocytes.

Immature DC have a high capacity for taking up and processing antigen, but have a limited ability to initiate immune responses. The ability to initiate an immune response is acquired by maturation of the immature DC. This maturation is also referred to as activating, or activation of, the DC. The maturation process is initiated through contact with maturation-inducing cytokines, tumor antigen compositions and/or nucleic acid compositions, and the like, as described herein.

II. Therapeutic Methods and Compositions

A. Pharmaceutical Compositions

In certain embodiments, the present invention concerns formulation of one or more dendritic cell or T-cell compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein.

In certain aspects of the present invention, pharmaceutical compositions are provided comprising one or more of the dendritic cell or T-cell compositions described herein in combination with a physiologically acceptable carrier. In certain preferred embodiments, the pharmaceutical compositions of the invention comprise immunologic cells of the invention for use in prophylactic and therapeutic applications. Generally, such compositions will comprise one or more dendritic or T cell composition of the present invention in combination with one or more immunostimulants.

B. Administration of Cell Populations

In another aspect of the invention, methods are provided for administration of mature dendritic cells or activated, polarized T cells, or a cell population containing such cells, to a subject in need thereof. Such cell populations can include both mature dendritic cell populations and/or activated, polarized T cell populations. In certain embodiments, such methods are performed by obtaining dendritic cell precursors or immature dendritic cells, differentiating and maturing those cells in the presence of a nucleic acid composition and a tumor antigen composition to form a mature dendritic cell population primed towards Th-1 response. The immature dendritic cells can be contacted with antigen prior to or during maturation. Such mature, primed dendritic cells can be administered directly to a subject in need of immunostimulation.

In a related embodiment, the mature dendritic cells can be contacted with lymphocytes from a subject to stimulate T cells within the lymphocyte population. The activated, polarized lymphocytes, optionally followed by clonal expansion in cell culture of antigen-reactive CD4+ and/or CD8+ T cells, can be administered to a subject in need of immunostimulation. In certain embodiments, activated, polarized T cells are autologous to the subject.

In another embodiment, the dendritic cells, T cells, and the recipient subject have the same MHC (HLA) haplotype. Methods of determining the HLA haplotype of a subject are known in the art. In a related embodiment, the dendritic cells and/or T cells are allogenic to the recipient subject. For example, the dendritic cells can be allogenic to the T cells and the recipient, which have the same MHC (HLA) haplotype. The allogenic cells are typically matched for at least one MHC allele (e.g., sharing at least one but not all MHC alleles). In a less typical embodiment, the dendritic cells, T cells and the recipient subject are all allogeneic with respect to each other, but all have at least one common MHC allele in common.

According to one embodiment, the T cells are obtained from the same subject from which the immature dendritic cells were obtained. After maturation and polarization in vitro, the autologous T cells are administered to the subject to provoke and/or augment an existing immune response.

III. Adoptive Immunotherapy Methods

As used herein, treating a subject using the compositions and methods of the present invention refers to reducing the symptoms of the disease, reducing the occurrence of the disease, and/or reducing the severity of the disease. Treating a subject can refer to the ability of a therapeutic composition of the present invention, when administered to a subject, to prevent a disease from occurring and/or to cure or to alleviate disease symptoms, signs or causes. As such, to treat a subject means both preventing disease occurrence (prophylactic treatment) and treating a subject that has a disease (therapeutic treatment). In particular, treating a subject is accomplished by providing or enhancing an immune response in the subject.

More specifically, therapeutic compositions as described herein, when administered to a subject by the methods of the present invention, preferably produce a result which can include alleviation of the disease, elimination of the disease, reduction of symptoms associated with the disease, elimination of symptoms associated with the disease, prevention of a secondary disease resulting from the occurrence of a primary disease, and prevention of the disease.

In certain embodiments, in vitro or in vivo generated $T_{H1}$-polarized CD8+DCs are used as adoptive immunotherapy for amelioration of disease symptoms.

In some of these embodiments, the $T_{H1}$-polarized CD8+ DCs are autologous/syngeneic to the subject and present antigen(s) associated with the aberrant immune response. For example, immature DCs can be harvested from a subject and treated in vitro with a $T_{H1}$-polarizing composition that contains the antigen of interest (e.g., tumor antigen(s)). The resultant mature DC can then be administered to the subject. In some embodiments, a single antigen or antigenic peptide is included in the tumor antigen composition whereas in other embodiments, more than one antigen or antigenic peptide may be used, including 2, 3, 4, 10 or more including a cell lysate or varying purities. Additionally, multiple independently generated DCs can be administered to a subject. Furthermore, administration of DCs to a subject can be done as often as is required to ameliorate the symptoms associated with the disease state.

In other of these embodiments, the DCs are allogeneic to the subject. For example, immature dendritic cells can be harvested from an organ donor and treated in vitro with a nucleic acid and tumor antigen composition. The resultant allogeneic mature DCs can then be administered to the subject to promote the cure or treatment of disease in that subject.

In certain embodiments, in vivo or in vitro generated cells are used in an adoptive immunotherapy method to ameliorate symptoms associated with a disease, such as cancer, in a subject.

In certain of these embodiments, the cells are autologous/syngeneic to the subject. For example, naive and/or memory T cells can be harvested from a subject and cultured in vitro with mature DCs. The antigen specific cells that develop can be purified and administered to the subject where they function to provide or enhance a therapeutic immune response.

In certain embodiments of the adoptive immunotherapy methods described above, the cells of interest (i.e., mature DCs or T cells) can be purified prior to administration to the subject. Purification of the cells can be done using a variety of methods known in the art, including methods in which antibodies to specific cell surface molecules are employed. These methods include both positive and negative selection methods. For example, T cells generated in vitro can be isolated by staining the cells with fluorescently labeled antibodies to cell surface markers followed by sorting of the cells that express both of these markers on their cell surface using fluorescence activated cell sorting (FACS). These and other purification/isolation methods are well known to those of skill in the art.

The mature DCs or T cells of the invention either can be used immediately after their generation (and purification, if applicable) or stored frozen for future use. In certain embodiments, enough mature DCs or T cells are generated to provide an initial dose for the subject as well as cells that can be frozen and stored for future use if necessary.

In certain other embodiments, mature DCs or T cells can be expanded in vitro from freshly isolated or frozen cell stocks to generate sufficient numbers of cells for effective adoptive immunotherapy. By effective dose is meant enough cells to ameliorate at least one symptom caused by the disease of interest. The determination of an effective dose for therapeutic purposes is known in the art. The expansion of the cells can be achieved by any means that maintains their functional characteristics. The phenotypic and functional properties of the resultant expanded cells can be tested prior to their therapeutic use and/or storage to verify that the expansion process has altered their activity.

IV. Expression Assays

One application of interest is the examination of gene expression in mature DCs or T cells of the invention. The expressed set of genes may be compared with a variety of cells of interest, e.g. other DCs, etc., as known in the art. For example, one could perform experiments to determine the genes that are regulated during development of the maturation processes.

Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A mRNA. One of skill in the art can readily use these methods to determine differences in the size or amount of mRNA transcripts between two samples. For example, the level of particular mRNAs in DCs is compared with the expression of the mRNAs in a reference sample.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of polynucleotides, particularly polynucleotides corresponding to one or more differentially expressed genes.

Alternatively, gene expression in a test sample can be performed using serial analysis of gene expression (SAGE) methodology (Velculescu et al., Science (1995) 270:484). SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific polynucleotide sequences (or restriction enzyme sites) are used as unique identifiers of genes, coupled with information about fragment length or fragment location within the expressed gene. The relative representation of an expressed gene with in a sample can then be estimated based on the relative representation of the fragment associated with that gene within the pool of all possible fragments. Methods and compositions for carrying out DD are well known in the art, e.g., U.S. Pat. Nos. 5,776,683; and 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry).

Methods for collection of data from hybridization of samples with arrays are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., Genome Res. (1996) 6:639.

In another screening method, the test sample is assayed at the protein level. Analysis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry, microscopy, radiography, scintillation counting, etc. Any suitable alternative methods of qualitative or quantitative detection of levels or amounts of differentially expressed polypeptide can be used, for example ELISA, western blot, immunoprecipitation, radioimmunoassay, etc.

V. Screening Assays

The subject cells are useful for in vitro assays and screening to detect or characterize cells contributing to a disease state. A wide variety of assays may be used for this purpose, including immunoassays for protein binding; determination of cell growth, differentiation and functional activity; production of cytokines; and the like.

In screening assays for biologically active agents the subject cells, usually a culture or a biopsy comprising the subject cells, is contacted with the agent of interest, and the effect of the agent assessed by monitoring output parameters, such as expression of markers, cell viability, and the like. The cells may be freshly isolated, cultured, genetically altered, or the like.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

VI. Kits

The present invention further pertains to a packaged pharmaceutical composition for producing $T_h1$ dendritic cells or T cells stimulated by the same such as a kit or other container. The kit or container holds an effective amount of a pharmaceutical composition for carrying out the methods or producing the compositions described herein and/or instructions for producing or using the compositions for therapy of a patient or subject having or suspected of having or at risk of developing cancer. The pharmaceutical composition includes at least one nucleic acid, polypeptide, or antibody of the present invention, in an effective amount such that the selected cancer is controlled. The kit may also contain various reagents and containers for monitoring the isolation and maturation and function of $T_h1$ dendritic cells or activated T cells.

VII. Cancers

In some methods of the invention, the cancer cell is a tumor cell. The cancer cell may be in a patient. The patient may have a solid tumor. In such cases, embodiments may further involve performing surgery on the patient, such as by resecting all or part of the tumor. In additional embodiments compositions may be administered directly, endoscopically, intratracheally, intratumorally, intravenously, intralesionally, intramuscularly, intraperitoneally, regionally, percutaneously, topically, intrarterially, intravesically, or subcutaneously. Compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. It is specifically contemplated that any of the compounds or derivatives or analogs, can be used with these combination therapies.

In some embodiments, the cancer cell that is administered viral compositions may be a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell.

Cancers that may be evaluated by methods and compositions of the invention include cancer cells that include cells and cancer cells from the bladder, blood, bone, bone marrow, brain, breast, colon, esophagus, gastrointestine, gum, head, kidney, liver, lung, nasopharynx, neck, ovary, pancreas, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, RNA can be evaluated in pre-cancers, such as metaplasia, dysplasia, and hyperplasia.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Materials and Methods

Generation of Immature Dendritic Cells.

Cryopreserved, normal donor, granulocyte colony stimulating factor (G-CSF) mobilized peripheral blood progenitor cells donated for research under M.D. Anderson IRB protocol #Lab 02-630 were used for these studies. Upon thawing, samples were resuspended in 100 ml CliniMacs buffer (Miltenyi Biotec, Auburn, Calif.) supplemented with 0.5% human serum albumin (Baxter, Deerfield, Ill.) and the mononuclear cells (MNCs) separated by centrifugation on a Histopaque1077 (Sigma, St. Louis, Mo.) gradient for 20 min at 450×g. Following purification, CD14+ MNCs were isolated on a magnetic separation column with CD14 Microbeads according to the manufacturer's instructions (Miltenyi Biotec). CD3, CD14, CD83, and CD209 surface expression of all cell preparations were characterized both pre- and post-selection by flow cytometry (BD Biosciences, San Diego, Calif.). CD14+ cells were cultured for 6 days at a concentration of $2\times10^6$ cells/ml in AIM-V medium (Invitrogen, Carlsbad, Calif.) supplemented with 10% Human AB Serum (Atlanta Biologicals, Lawrenceville, Ga.), 50 µg/ml streptomycin sulfate (Invitrogen), 10 µg/ml gentamycin sulfate, 2 mM L-glutamine (Invitrogen), 50 ng/ml GM-CSF (Amgen, Thousand Oaks, Calif.), and 10 ng/ml IL-4 (R&D Systems, Minneapolis, Minn.). The culture medium was removed and replenished with an equal volume of fresh medium on day 3. Cells were cultured in a humidified chamber at 37° C. and 5% atmospheric $CO_2$.

Preparation of Tumor Lysate and Tumor mRNA.

Tumor lysate was prepared by the suspension of AML blasts in unsupplemented AIM-V medium at a concentration of $2\times10^7$ cells/ml followed by three successive freeze/thaw cycles at −80° C./37° C. The lysate fraction was placed at −80° C. until needed for use. Protein concentration was determined by the bicinchoninic acid (BCA) assay according to the manufacturer's instructions (Pierce, Rockford, Ill.). Total tumor RNA was extracted from AML blasts using Trizol reagent (Invitrogen) at an original concentration of $10^7$ cells/ml Trizol according to the manufacturer's instructions. mRNA was isolated from total tumor RNA using an Oligotex Direct Maxi Kit (Qiagen, Valencia, Calif.) also according to the manufacturer's instructions. mRNA yield was determined by UV spectroscopy, and mRNA quality was verified by gel electrophoresis. Antigenic materials were derived from one of three different products of emergency leukodepletion performed to prevent patient leukostasis. These products were randomly provided to the investigators and consisted of 93%, 74%, and 95% malignant cells identified as FAB M3, FAB M4, and biphenotypic acute leukemia, respectively.

DC Loading and Maturation.

After 6 days of culture in GM-CSF and IL-4, immature dendritic cells were loaded with either tumor lysate, tumor mRNA, or both. When loaded with lysate, immature dendritic cells were cultured for three hours at 37° C. at a concentration of $5\times106$ cells/ml in a fourfold dilution of blast lysate. Following lysate loading, cells were pelleted, washed once to remove residual lysate, and matured for 48 h in AIM-V supplemented as previously described but with the addition of ITIP [10 ng/ml IL-1β (R&D Systems), 10 ng/ml TNF-α (R&D Systems), 15 ng/ml IL-6 (R&D Systems), and 1 R9/m1PGE2 (Sigma)]. CD3, CD14, CD83, and CD209 surface expression of all cell preparations were characterized both pre- and post-maturation by flow cytometry. Additionally, CD11c, CD80, CD86, and HLA-DR surface expression of mature dendritic cells was also characterized by flow cytometry (BD Biosciences). In addition to flow cytometry, a variety of 3H-based growth controls confirmed that dendritic cell preparations were devoid of CD3+ lymphocytes, and dendritic cells were never irradiated. For loading with mRNA, immature dendritic cells were suspended at a concentration of $4\times10^7$ cells/ml in Viaspan (Barr Laboratories, Pomona, N.Y.), mixed with tumor mRNA to a concentration of 1 mRNA/106 cells, and incubated for 10 min on ice in an electroporation cuvette with an 0.4 cm gap (Biorad, Hercules, Calif.). Cells were then electroporated at 300 V, 1501 1F, and S2=oo using a GenePulser Xcell (Biorad). Following electroporation, cells were immediately introduced into culture and treated identically to lysate-loaded DCs. DC viability post-electroporation was typically greater than 75%. Doubly-loaded dendritic cells always received lysate and mRNA preparations from the same leukemia unless specifically stated otherwise. When loaded with both mRNA and lysate, cells originally received lysate first and mRNA second. As the experimental procedure was refined, mRNA was loaded first and lysate second to prevent RNase contamination from leukemic lysates from degrading the mRNA. In general, this procedural difference did not overtly alter the experimental results, and results obtained from either protocol were comparable.

T-Cell Priming and Restimulation.

Upon full maturation of loaded dendritic cells, $10^6$ mature DCs were incubated with $10^7$ autologous non-adherent PBMCs (typically 50% CD3+) in 10 ml RPMI-1640 supplemented with 10% Human AB Serum, 100 U/ml penicillin G/100 U/ml streptomycin, and 2 mM L-glutamine in a T25 tissue culture flask (Corning, Corning, N.Y.). Unused mature dendritic cells were frozen at −80° C. in 90% Human AB Serum/10% DMSO for future use. No IL-2 was added to the culture medium during the primary stimulation. Restimulation was performed every 8-10 days by the withdrawal of $10^7$ lymphocytes from the previous culture and the addition $10^6$ thawed dendritic cells. All restimulations were performed in T75 flasks to allow increased lymphocyte proliferation. At 48 h post-restimulation, lymphocytes were typically supplemented with IL-2 (Chiron, Emeryville, Calif.) at a concentration of 1000 U/ml to aid T-cell expansion. Subsequently, fresh IL-2 was added every 48 h.

ELISpot Assay.

ELISpot assays were performed on day 5 of primary stimulations or day 3 of restimulations unless otherwise indicated. Typically, $10^4$-$10^5$ lymphocytes from each stimulation culture were plated in triplicate on anti-IFN-γ coated ELISpot plates (BD Biosciences) and cultured overnight (12-18 h) at 37° C. IFN-γ spots were developed using an ELISpot Human IFN-γ Kit (BD Biosciences) according to the manufacturer's instructions and were read with an Axioplan2 Imaging Microscope (Carl Zeiss, Thornwood, N.Y.) and interpreted using KS EliSpot Version 4.5.21 software (Carl Zeiss). ELISpot assays were performed independently on multiple occasions using 11 different normal donor products and antigenic material derived from one of three different tumor products.

CD40 Agonism/Antagonism and CD4 Depletion.

CD40 agonism was simulated by addition of 1 μg/ml antiCD40 clone 82111 (R&D Systems) during both primary and secondary T-cell stimulations. Similarly, CD40 antagonism was performed by addition of 1 μg/ml anti-CD40L clone 40804 (R&D Systems) during both primary and secondary T-cell stimulations. Recall responses were quantitated by IFN-γ ELISpot 72 h following restimulation. In CD4 depletion experiments, CD4 cells were depleted by positive magnetic selection using anti-CD4 magnetic beads (Miltenyi Biotec).

$^{51}$Cr CTL Assay.

Typically, $10^6$ target cells were labeled overnight at 37° C. in 200 μl RPMI-1640 supplemented with 100 μCi $^{51}$Cr (Perkin-Elmer, Boston, Mass.). Targets included the TF1 a (human erythroblast) cell line [30], allogeneic leukemic blasts, and autologous AML-loaded dendritic cells. AML blast targets were derived directly from fresh patient leukodepletion products prior to cryopreservation. In a few instances, these fresh blasts were able to be cultured in perpetuity in RPMI-1640 supplemented with IL-3. After labeling, target cells were washed once and incubated for one hour in 10 ml RPMI-1640 to allow washout of loosely-associated chromium. Targets were washed a second time and then added to 96-well V-well plates (Corning) to which effector cells had already been added. All reactions were carried out in 100 μl RPMI-1640 unless otherwise indicated. Mixed target and effector cells were pelleted for 4 min at 300×g and then incubated for 6 h at 37° C. Plates were then recentrifuged, and 45 μl of supernatant was transferred to Luma96 plates (Perkin-Elmer). Following evaporation of the supernatant, Luma plates were read on a TopCount NXT (Perkin-Elmer, formerly Packard Instruments) running version 1.06 software. Specific lysis was determined by the following formula: SL= (sample value−spontaneous lysis value)/(maximum lysis value−spontaneous lysis value)×100%. Spontaneous lysis was always less than 15% of maximal lysis.

Statistical Analysis.

Statistical differences were calculated by Student's unpaired two-tailed t-test unless stated otherwise. Significance was defined as $p<0.05$. In some instances, multiple p-values were generated by a pairwise comparison between the doubly-loaded group and any other relevant groups listed in the figure; however, only the least significant of these multiple p-values was given.

Results

Doubly-Loaded, Matured DCs Express High Levels of Dendritic Cell-Specific Markers and do not Differ Objectively from Singly-Loaded Dendritic Cells.

Figure 3:
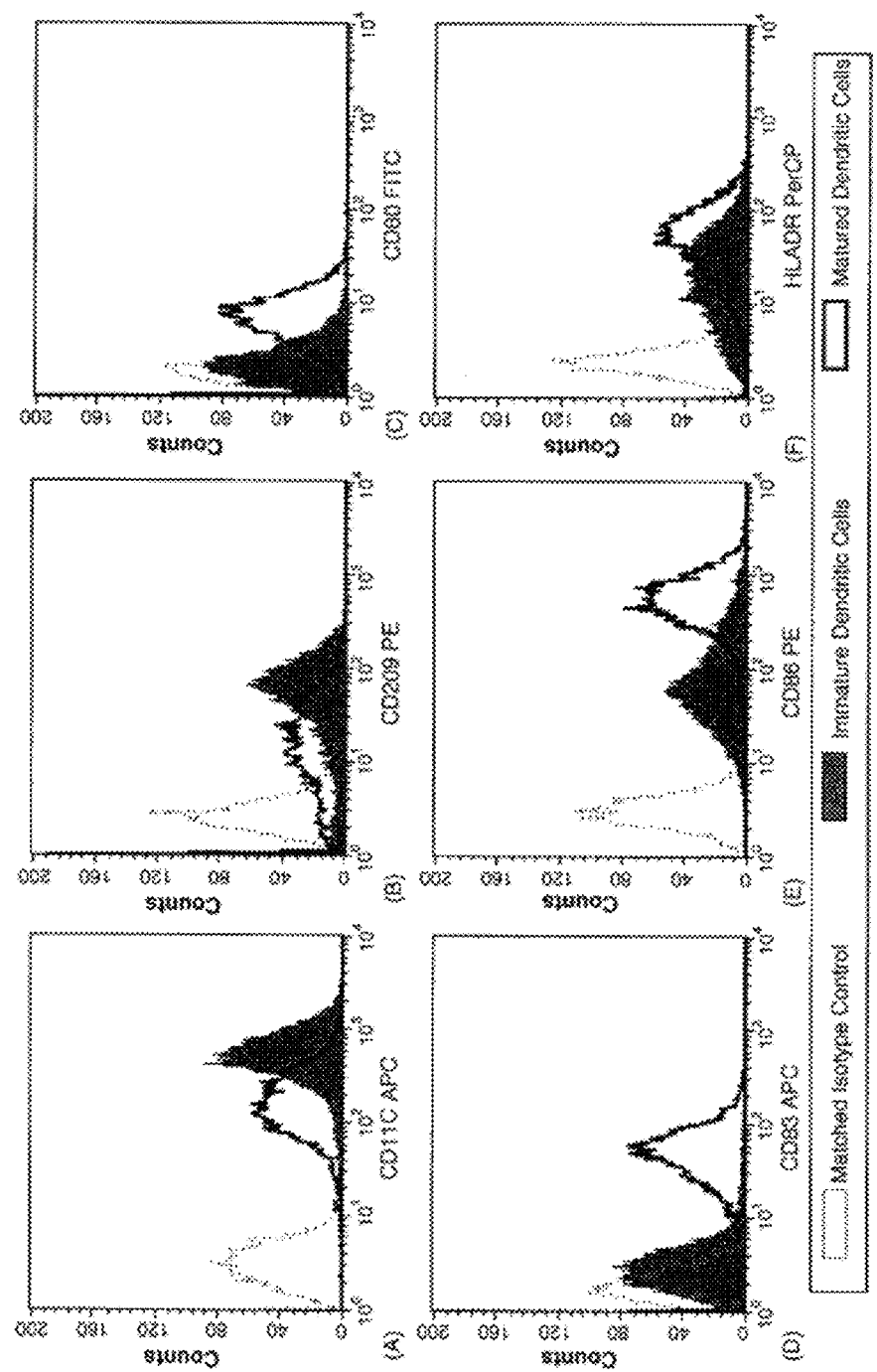
FIGS. 3A-F. Doubly-loaded dendritic cells show appropriate upregulation of DC-specific markers upon maturation. Immature dendritic cells were generated by the culture of CD 14+ selected monocytes in GM-CSF and IL-4 for 6 days. Immature dendritic cells were then doubly-loaded and matured for 48 h. Doubly-loaded DCs were stained for CD11c, CD80, CD83, CD86, CD209, and HLA-DR surface expression as determined by flow cytometry. More than 20 experiments were performed using 11 different normal donors and antigenic materials derived from three different patients; a typical experiment is shown here. (A) CD11c; (B) CD209; (C) CD80; (D) CD83; (E) DC86; (F) HLA-DR. Gray plot: immature dendritic cells. Thick line: matured dendritic cells. Thin dotted line: matched isotype control.

Following 6 days of culture in GM-CSF and IL-4, immature dendritic cells displayed the phenotype of $CD11c^+$, $CD80^-$, $CD83^-$, $CD86^+$, $CD209^+$, and $HLA-DR^+$ as determined by flow cytometry (FIG. 3, gray shaded plots). Following loading and maturation with ITIP, DCs doubly-loaded with both mRNA and lysate displayed the phenotype of $CD11c^+$, $CD80^+$, $CD83^+$, $CD86^{++}$, $CD209^+$, and $HLA-DR^{++}$ (FIG. 3, thick black lines). There were no statistical differences in the expression levels of B7-1 (CD80), B7-2 (CD86), or HLA-DR between matured doubly-loaded dendritic cells and matured singly-loaded dendritic cells. Expression of adhesion markers (i.e. CD209 and CD11c) between doubly and singly-loaded dendritic cells was indistinguishable as well (data not shown). These experiments were performed over 20 times using various combinations of 11 different normal donor products and one of three different tumor products as antigenic material. A representative experiment is shown. Note that markers involved with co-stimulation or antigen presentation were upregulated upon maturation (CD80, CD83, CD86, HLA-DR), whereas markers involved with adhesion were downregulated (CD11c, CD209). Essentially 100% of matured, doubly-loaded DCs expressed CD11c, CD86, and HLA-DR. Approximately 80-95% expressed the CD80 and CD83 maturation-specific markers, and approximately 40-70% expressed CD209.

T-Cells Primed and/or Restimulated by Doubly-Loaded Dendritic Cells Consistently Exhibit Enhanced IFN-γ Secretion by ELISpot Assay.

Figure 4:
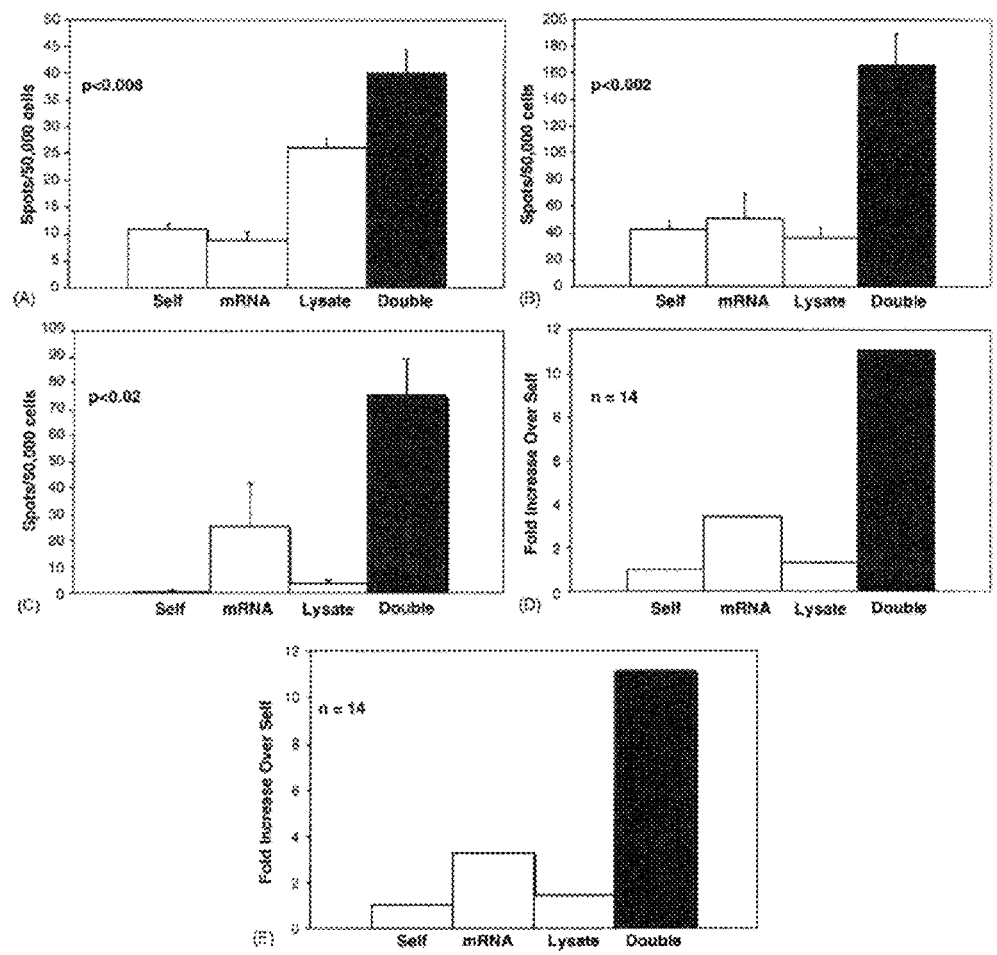
FIGS. 4A-E. Doubly-loaded dendritic cells consistently enhance T-cell priming as assayed by IFN-γ ELISpot of primary stimulations. Following differentiation, immature DCs were loaded with either AML mRNA, AML tumor lysate, both AML mRNA and AML tumor lysate, or nothing (self-antigen control), and then matured for 48 h. Matured DCs ($10^6$) were co-cultured for 5 days with $10^7$ non-adherent, autologous PBMCs. After a single 5-day stimulation, $10^4$-$10^5$ cells were plated in triplicate onto a 96-well ELISpot plate and incubated at 37° C. for 18 h. ELISpots were then developed, and the total number of IFN-γ spots was quantitated. Medium-only, dendritic cell-only, and lymphocyte-only controls were always devoid of spots and have been omitted from the data. Fourteen different experiments were performed using one of 11 different normal donor products and one of three different tumor products as antigen. Three representative experiments (panels A through C) are shown here to demonstrate biological variability observed between donors. Panel D shows a composite of 14 different experiments in which the autoantigen control has been arbitrarily assigned a value of 1. In any given experiment, the response from T-cells primed by doubly-loaded dendritic cells was statistically greater than that of all other experimental groups (p<0.05), similarly as shown in A-C. Panel E shows a composite of similar results obtained following recall stimulation. Self: T-cells primed by dendritic cells presenting self-antigens only (not loaded with tumor antigens). mRNA: T-cells primed by dendritic cells loaded with AML-specific mRNA. Lysate: T-cells primed by dendritic cells loaded with AML-specific lysate. Double: T-cells primed by AML-specific doubly-loaded dendritic cells. Y-axis A-C: ELISpots/given cell number. Y-axis D-E: fold increase in IFN-γ ELISpots in comparison to self. Error bars: ±S.E.M.

Following differentiation, immature DCs were loaded with either acute myelogenous leukemia mRNA, AML tumor lysate, both AML mRNA and AML tumor lysate, or nothing (autoantigen control), and then matured for 48 h. Matured DCs ($10^6$) were co-cultured for 5 days with $10^7$ non-adherent, autologous PBMCs in RPMI-1640 supplemented with 10% Human AB Serum. After a single 5-day stimulation, $10^4$-$10^5$ cells were plated in triplicate onto a 96-well ELISpot plate and incubated at 37° C. for 18 h. ELISpots were then developed, and the total number of IFN-γ spots was quantitated. ELISpot assays were performed independently on 14 different occasions using 11 different normal donor products and antigenic material derived from one of three different tumor products. Three representative experiments (FIG. 4A-4C) are shown here to demonstrate the typical biological variability observed between donors. FIG. 4D shows a composite of all experiments in which the autoantigen control has been arbitrarily assigned a value of 1. This composite demonstrates that lymphocytes primed by doubly-loaded dendritic cells demonstrated an 11-fold increase in IFN-γ secreting cells in comparison to unloaded self-antigen controls. Lysate-loaded and mRNA-loaded dendritic cells imparted only a 1.3-fold increase and a 3.4-fold increase, respectively, over the self-antigen control. Similar results were also observed following recall stimulation (FIG. 4E). In any given experiment, the response from T-cells primed by doubly-loaded dendritic cells was always statistically greater than that of all other experimental groups ($p<0.05$). Medium-only, DC-only, and unstimulated controls were always devoid of spots. While it is possible that these results were due solely to increased antigen concentrations within doubly-loaded DCs, neither the doubling or halving of the lysate concentration, nor the halving of the mRNA concentration affected the outcome of these experiments in a statistically significant manner (data not shown).

Doubly-Loaded Dendritic Cells Enhance T-Cell Help as Demonstrated by CD40 Agonism and Antagonism.

Figure 5:
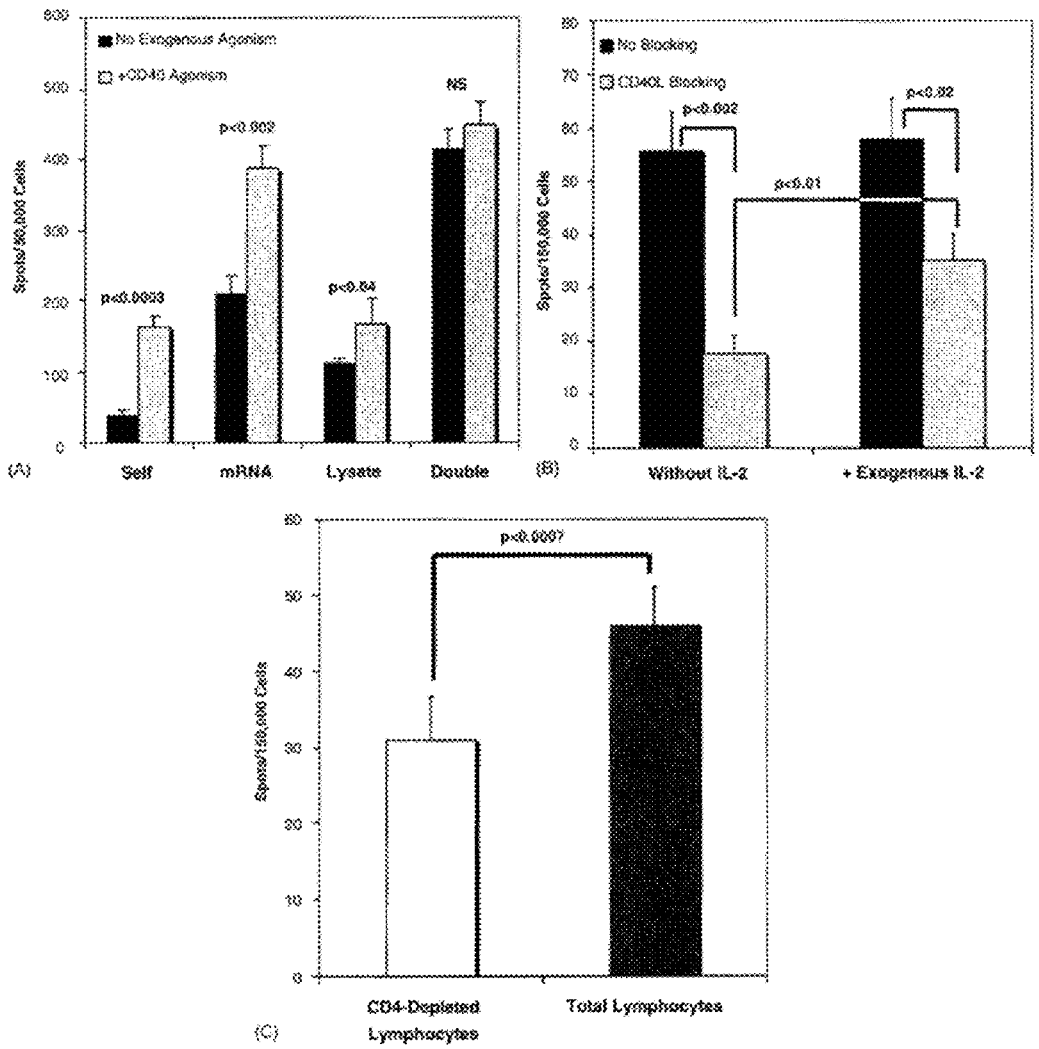
FIGS. 5A-C. Doubly-loaded dendritic cells capitalize upon T-cell help to enhance T-lymphocyte activation as demonstrated by addition of exogenous CD40 agonism/antagonism and detection of IFN-γ ELISpots upon recall. Non-adherent PBMCs were primed and restimulated once with one of four populations of autologous dendritic cells: unloaded (self-antigen control), mRNA-loaded, lysate-loaded, or doubly-loaded. (A) CD40 Agonism. Priming and restimulation were performed in both the presence and absence of a CD40 agonist antibody (1 µg/ml) that mimics the effect of T-cell help as provided by CD40L. Nine days after the primary stimulation, primed lymphocytes were restimulated with the same dendritic cell populations and assayed for IFN-γ secretion by IFN-γ ELISpot assay 72 h after restimulation. Self: T-cells primed by dendritic cells presenting self-antigens only. mRNA: T-cells primed by dendritic cells loaded with AML-specific mRNA. Lysate: T-cells primed by dendritic cells loaded with AML-specific lysate. Double: T-cells primed by AML-specific doubly-loaded dendritic cells. IFN-γ ELISpots observed in the absence of exogenous CD40 agonism (control) are shown by the black bars. IFN-γ ELISpots observed in the presence of CD40 agonism are demonstrated by the gray bars. The experiment was performed on three independent occasions with comparable results. A representative experiment is shown here. Exogenous CD40 agonism was unable to increase the number of IFN-γ ELISpots produced by lymphocytes primed/restimulated by doubly-loaded dendritic cells, an indication that double loading of dendritic cells may impart a maximal availability of T-cell help. (B) CD40 Antagonism. The reciprocal experiment was then performed with an antagonist antibody that blocks the CD40/CD40L interaction. IFN-γ ELISpots observed in the absence of CD40L antagonism (control) are shown by the black bars. IFN-γ ELISpots observed in the presence of CD40L antagonism are demonstrated by the gray bars. Antibody blockade of the CD40/CD40L interaction reduced by 68% (p<0.002) the number of IFN-γ ELISpots produced by lymphocytes primed/restimulated by doubly-loaded dendritic cells. CD40 antibody blockade had no effect on the number of IFN-γ ELISpots observed from T-cells primed and restimulated by unloaded (self-antigen) or singly-loaded (data not shown). The addition of exogenous IL-2 to the ELISpot reaction could moderate the reduction in IFN-γ signaling observed from lymphocytes primed/restimulated by doubly-loaded dendritic cells following CD40 antibody blockade. (C) Degree of CD4 depletion.

To demonstrate that doubly-loaded dendritic cells indeed aid in the enhancement of CD40L-mediated T-cell help, non-adherent PBMCs were primed and restimulated once with one of four populations of autologous dendritic cells: unloaded (self-antigen control), mRNA-loaded, lysate loaded, or doubly-loaded. Priming and restimulation were then performed both in the presence and absence of a CD40 agonist antibody that mimics the effect of T-cell help as provided by CD40L. Nine days after the primary stimulation, primed lymphocytes were restimulated with the same dendritic cell populations and assayed for IFN-γ secretion by IFN-γ ELISpot assay on day 3 following the restimulation. The experiment was performed independently on three separate occasions with comparable results. The number of IFN-γ ELISpots observed in the absence of CD40 agonism is shown by the black bars. The number of IFN-γ ELISpots observed in the presence of CD40 agonism is demonstrated by the gray bars (FIG. 5A). In the representative experiment shown here, CD40 agonism increased the number of IFN-γ ELISpots observed upon restimulation of T-cells primed by mRNA-loaded DCs by 86% ($p<0.002$) and of T-cells primed by lysate-loaded DCs by 51% ($p<0.04$). T-cells primed by doubly-loaded DCs were unaffected by CD40 agonism following restimulation, demonstrating a net 8% increase in IFN-γ ELISpots ($p>0.05$, not statistically significant). Self-antigen controls demonstrated a six-fold increase in IFN-γ ELISpots ($p<0.0003$), and medium-only, DC-only, and lymphocyte-only controls were devoid of spots (data not shown). These results suggest that doubly-loaded dendritic cells may allow for a maximal recruitment of CD40L mediated T-cell help, i.e. the addition of exogenous CD40 agonism was able to improve the ability of unloaded/singly loaded dendritic cells to prime T-lymphocytes; however, exogenous CD40 agonism was unable to improve the ability of doubly-loaded dendritic cells to prime T-lymphocytes.

To verify these results, the reciprocal experiment was performed with an antagonist antibody that binds CD40L, blocking its interaction with CD40 (FIG. 5B). In agreement with the previous experiment, T-lymphocytes primed and restimulated by unloaded/singly-loaded dendritic cells were wholly unaffected by the addition of CD40 antagonism ($p>0.05$) in terms of IFN-γ secretion (data not shown). In contrast, T-lymphocytes primed and restimulated by doubly-loaded dendritic cells demonstrated a net 68% decrease in IFN ELISpots ($p<0.002$). Addition of exogenous IL-2 to the ELISpot reaction could moderate the reduction in IFN-γ signaling observed from lymphocytes primed/restimulated by doubly-loaded dendritic cells following CD40 antibody blockade ($p<0.01$); however, complete IFN-γ signaling could not be restored ($p<0.02$). Addition of exogenous IL-2 to self-antigen/singly-loaded control dendritic cells had no effect on lymphocyte IFN-γ signaling. Furthermore, 75-80% depletion of CD4+ cells from the lymphocyte subset prior to priming and restimulation by doubly-loaded dendritic cells (FIG. 5C) resulted in a 33% decrease in IFN-γ ELISpots following recall ($p<0.0007$). The degree of CD4 depletion was determined by flow cytometry (data not shown). FIG. 5C as shown is a composite of an experiment performed in duplicate. In aggregate, these results strongly suggest that CD40L signaling between the CD4+ helper T-lymphocyte and the dendritic cell is mechanistically important to T-cell priming by doubly-loaded dendritic cells.

Activation of CD8+ Lymphocytes is Significantly Enhanced Following Stimulation with Doubly-Loaded Dendritic Cells.

Figure 6:
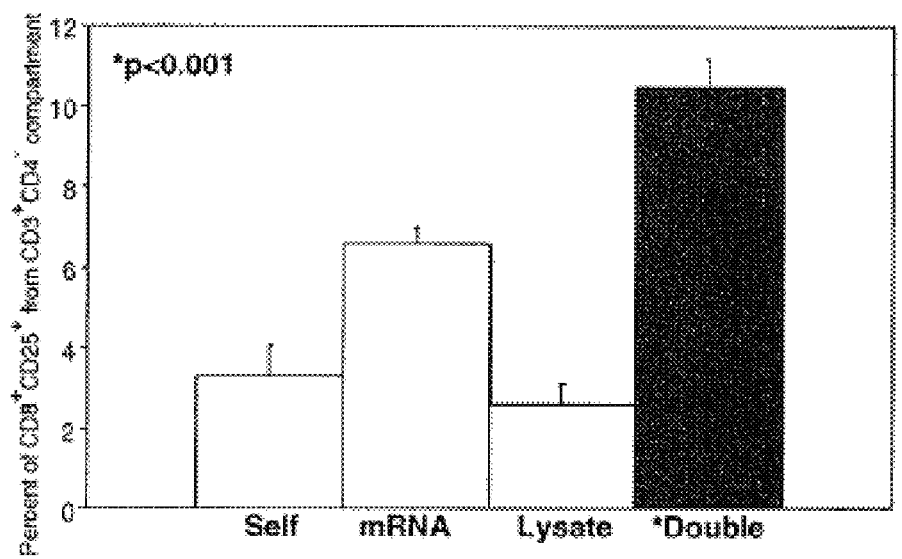
FIG. 6. Activation of CD8+ Lymphocytes is Significantly Enhanced following Stimulation with Doubly-Loaded Dendritic Cells. Non-adherent PBMCs were primed for 9 days and restimulated once with one of four populations of autologous dendritic cells: self (autoantigen control), mRNA-loaded, lysate-loaded, or doubly-loaded. Three days after restimulation, non-adherent cells (typically >80% T-lymphocytes) were harvested and analyzed by flow cytometry for the CD3, CD4, CD8, and CD25 surface markers. The percentage of CD8+CD25+ cells in the CD31−CD4− compartment were then determined. Shown here are the composite results of three independent experiments. Results indicated that priming/restimulation with doubly-loaded dendritic cells could elevate the number of activated CD8+ lymphocytes (CD3+ CD4−CD8+CD25+) almost twofold (p<0.001) in comparison to stimulation with mRNA-loaded dendritic cells and almost fourfold in comparison to background controls (p<0.0003). As anticipated, lysate loaded dendritic cells were relatively poor activators of CD8+ lymphocytes in the system. Self: unloaded dendritic cells presenting only autoantigens. mRNA: mRNA-loaded dendritic cells. Lysate: lysate-loaded dendritic cells. Double: doubly-loaded with tumor mRNA and lysate. Y-axis: percent of CD8+CD25+ Cells in the CD3+ CD4− Compartment. Error bars: ±S.E.M.

To correlate CD8+ CTL activation with ELISpot results, non-adherent PBMCs were primed for 9 days and restimulated once with one of four populations of autologous dendritic cells: unloaded (autoantigen control), mRNA-loaded, lysate-loaded, or doubly-loaded. Three days after restimulation, non-adherent cells (typically >80% lymphocytes) were harvested and analyzed by flow cytometry for the CD3, CD4, CD8, and CD25 surface markers. The percentage of CD8+ CD25+ cells in the CD3+CD4− compartment was then determined. Shown in FIG. 6 are the composite results of three independent experiments. Results indicate that priming/restimulation with doubly-loaded dendritic cells could elevate the number of activated CD8+ lymphocytes (CD3+CD4−CD8±CD25±) almost twofold ($p<0.001$) in comparison to stimulation with mRNA-loaded dendritic cells and almost fourfold in comparison to background (self-antigen) controls ($p<0.0003$). As anticipated, lysate-loaded dendritic cells were relatively poor activators of CD8+ lymphocytes in this system ($p<0.00009$). There were no statistically significant differences in CD4+CD25+ lymphocytes among the four experimental groups.

Doubly-Loaded Dendritic Cells May Enhance Th-1 Type Responses as Evidenced by Increased IL-12 (p70) Secretion.

Figure 7:
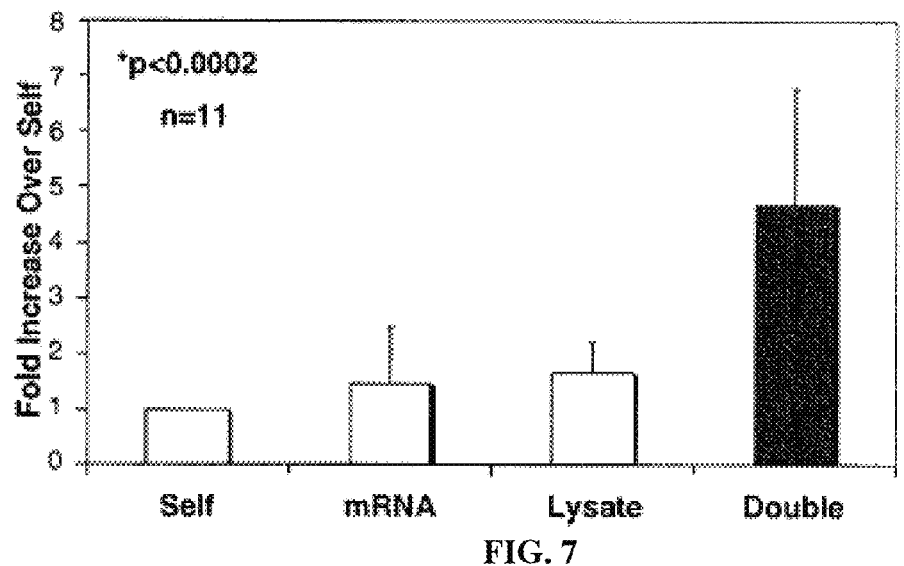
FIG. 7. Double loading of dendritic cells enhances IL-12 (p70) secretion. Shown here is a composite of 11 different experiments in which IL-12 secretion from dendritic cells was determined following loading with lysate, mRNA, both lysate and mRNA, or nothing. Analyses were performed using 11 different normal donor products in conjunction with tumor materials derived from one of three different leukemic patients. Since IL-12 secretion varied significantly by donor (20-400 pg/ml/$10^6$ cells), secretion was normalized to that of the self-antigen (unloaded) control which was arbitrarily assigned a value of 1. While the single loading of dendritic cells with either mRNA or lysate lead to a 1.5-fold (46%) and 1.7-fold (65%) increase in IL-12 secretion, respectively, the double loading of dendritic cells with both mRNA and lysate preparations lead to a fivefold (471%) increase in the amount of bioactive IL-12 secretion (p<0.0002). Y-axis: fold increase in IL-12 secretion in comparison to the self (unloaded) control. Error bars: ±S.E.M.

In addition to increased IFN-γ secretion by T-cells primed by doubly-loaded dendritic cells, additional evidence of enhanced Th-1 type responses was looked for by analyzing culture supernatants for increased IL-12 secretion. Analyses were performed using 11 different normal donor products in conjunction with tumor materials derived from one of three different leukemic patients. Since IL-12 secretion varied significantly by donor (20-400 pg/ml/$10^6$ cells), secretion was normalized to that of the self-antigen (unloaded) control which was arbitrarily assigned a value of 1. A composite of 11 different experiments is shown in FIG. 7. While single loading of dendritic cells with either mRNA or lysate lead to a 1.5-fold (46%) and 1.7-fold (65%) increase in IL-12 secretion, respectively, the double loading of dendritic cells with both mRNA and lysate preparations lead to a fivefold (471%) increase in the amount of bioactive IL-12 secretion ($p<0.0002$).

Cytotoxic T-Lymphocytes Primed by Doubly-Loaded Dendritic Cells Demonstrate Enhanced Specific Lysis of Leukemic Blasts and Loaded DC Targets.

Figure 8:
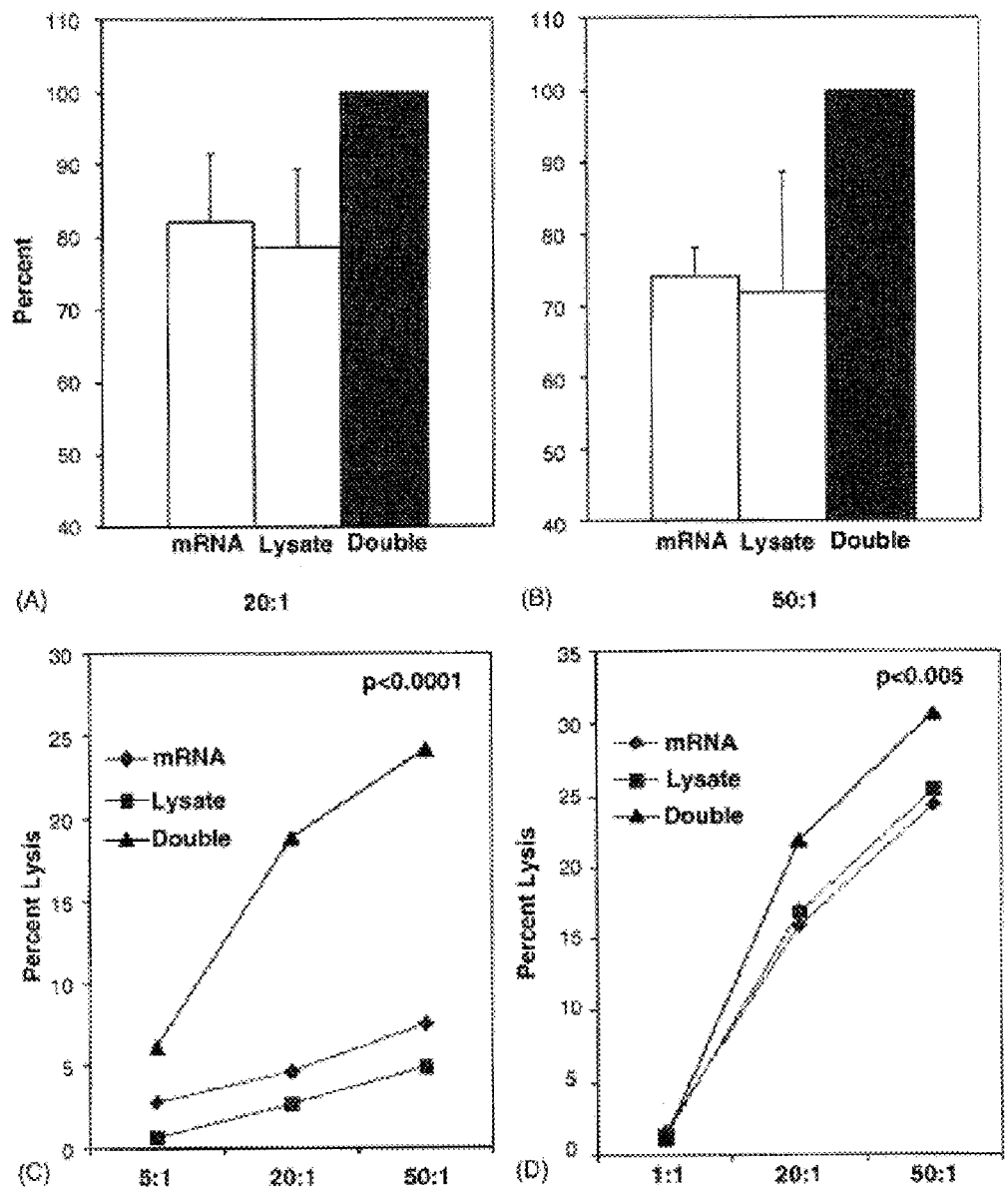
FIGS. 8A-D. CTL lysis of leukemic targets is enhanced when T-cells are primed and restimulated by doubly-loaded dendritic cells. Normal donor CTLs were primed and restimulated twice using autologous DCs loaded with mRNA and/or lysate that had been derived from an AML patient. Leukemic targets against which CTLs had been primed were $^{51}$Cr-labeled, and were assayed for the ability of these CTLs to lyse the labeled targets by $^{51}$Cr release. Targets consisted of allogeneic leukemic blasts or autologous dendritic cells loaded with leukemic antigens. A composite of four independent experiments is shown in panels A and B. Lytic activity of effectors stimulated by doubly-loaded dendritic cells was arbitrarily assigned a value of 100%. Irrespective of the target used, T-cells stimulated by doubly-loaded DCs consistently demonstrated 20% more lytic activity than T-cells stimulated by singly-loaded dendritic cells at an E:T ratio of 20:1 (Panel A). At an E:T ratio of 50:1, a 30% lytic advantage was consistently observed (Panel B). The effect was generally detectable at lower E:T ratios as well but was not always statistically significant. Effector lymphocytes and targets always shared in common at least one HLA class I allele. In all independent experiments, lysis mediated by T-cells stimulated with doubly-loaded dendritic cells was statistically different than lysis mediated by T-cells stimulated with singly-loaded dendritic cells (p<0.05) at the given E:T ratios. White bars: lytic activity of CTLs stimulated by singly-loaded dendritic cells. Gray bars: lytic activity of CTLs stimulated by doubly-loaded dendritic cells. X-axis: E:T ratio. Y-axis: percent comparative CTL lytic activity. Error bars: ±S.E.M. Panels C and D demonstrate two representative experiments using leukemic blasts as targets. X-axis: E:T ratio. Y-axis: percent lysis.

To examine the specific cytotoxic abilities of T-cells stimulated by doubly-loaded dendritic cells, the inventors $^{51}$Cr-labeled leukemic targets against which CTLs had been primed and assayed for the ability of CTLs to lyse these labeled targets by $^{51}$Cr release. Targets consisted of either allogeneic leukemic blasts or of autologous dendritic cells loaded with leukemic antigens. Shown is a composite of four independent experiments in which target lysis by effectors primed/restimulated by doubly-loaded DCs has been arbitrarily normalized to 100% (FIGS. 6A and 6B). Irrespective of the target used, T-cells stimulated by doubly-loaded DCs consistently demonstrated 20% more lytic activity than T-cells stimulated by singly-loaded dendritic cells at an E:T ratio of 20:1. At an E:T ratio of 50:1, a 30% lytic advantage was consistently observed. In general, this effect was also detectable at lower E:T ratios but was not always statistically significant. Percent CTL lysis ranged from 15 to 55%, depending, presumably, upon the number of HLA class I alleles shared by the target and the allogeneic donor from which effector T-cells were derived. Effector lymphocytes and targets always shared in common at least one HLA class I allele. The highest lytic levels were observed when effectors and targets (i.e., leukemia-loaded dendritic cells) were autologous. Shown in FIGS. 8C and 8D are two representative experiments. In any independent experiment, lysis mediated by T-cells stimulated with doubly-loaded dendritic cells was statistically different than lysis mediated by T-cells stimulated with singly-loaded dendritic cells ($p<0.05$) at the given E:T ratios. It has been previously demonstrated that target cell lysis in the system is mediated by an HLA-dependent mechanism (Xing et al., 2004).

Figure 9:
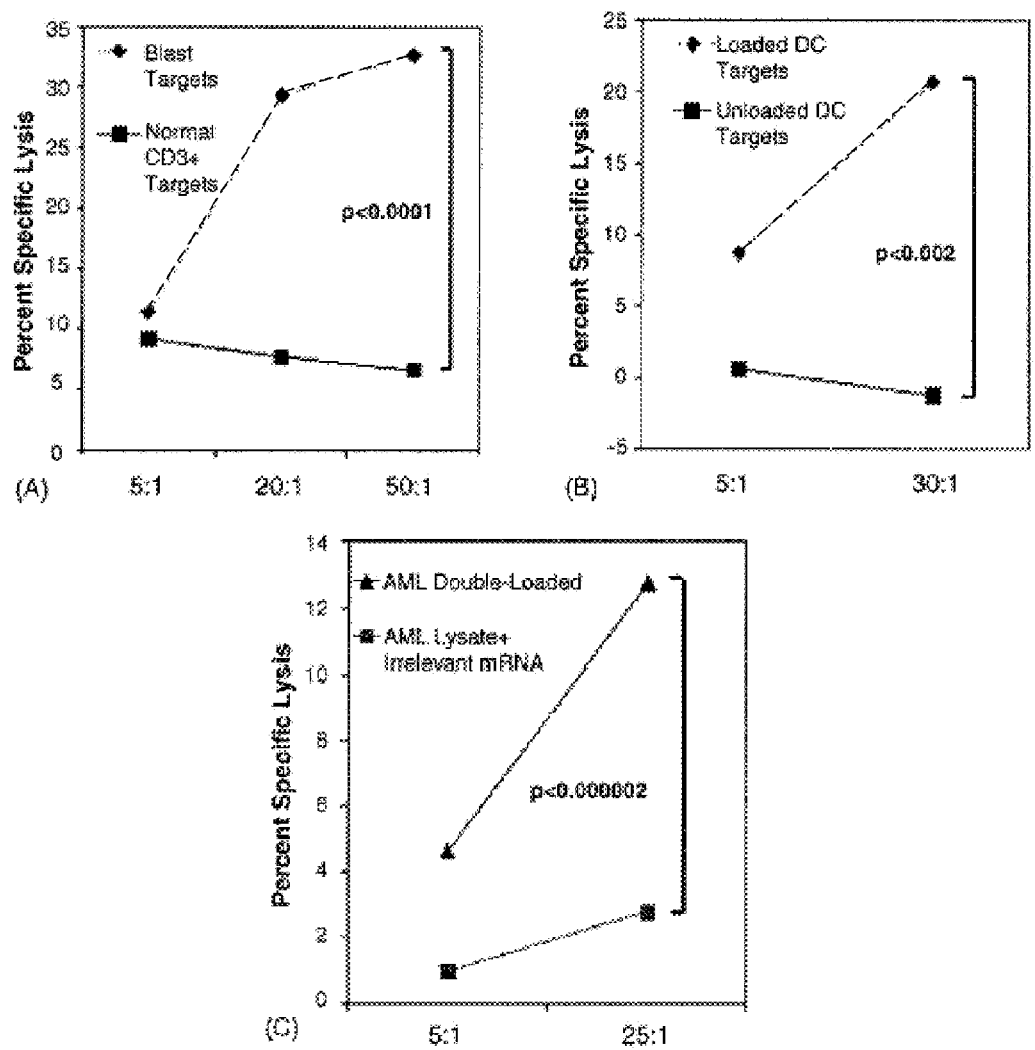
FIG. 9A-C. T-cells primed by doubly-loaded dendritic cells lyse targets in a specific fashion that is not dependent upon alloantigens. Non-leukemic CD3+ lymphocytes were magnetically isolated from an AML patient leukodepletion product and were expanded in vitro. Using these non-leukemic targets, the ability of CTLs primed by dendritic cells doubly-loaded with the same patient's leukemic antigens to lyse the non-leukemic targets by $^{51}$Cr release assay was assessed. Panel A demonstrates that effectors primed by doubly-loaded dendritic cells can efficiently lyse allogeneic leukemic blasts but cannot lyse the non-leukemic CD3+ controls (HLA-identical to the blasts). This experiment was performed on three independent occasions using two different normal donors. Results were comparable. Shown here is a representative experiment. Panel B depicts a similar experiment in the autologous setting. Here, effectors primed by doubly-loaded dendritic cells lyse autologous AML-loaded dendritic cell targets but cannot lyse the autologous unloaded controls. Black diamonds/dotted lines: leukemic targets. Black squares/solid lines: non-leukemic targets. X-axis: E:T ratios. Y-axis: percent CTL lysis. Panel C: loading of dendritic cells with AML lysate and FBMD-1 mRNA rather than matched AML mRNA generates effectors than cannot lyse AML blast targets ($p<0.000002$). Black triangles/line: effectors primed by DCs loaded with matched AML lysate and mRNA. Gray squares/line: effectors primed by DCs loaded with mismatched AML lysate and FBMD-1 mRNA. X-axis: E:T ratios. Y-axis: percent CTL lysis.

To establish the specificity of killing mediated by T-cells stimulated with doubly-loaded dendritic cells, normal CD3+ T-cells were isolated from an AML patient leukodepletion product by magnetic bead selection (Miltenyi Biotec) and cultured for 10 days in the presence of IL-2 and the absence of IL-3 to remove blast contamination. Surviving CD3+ T-cells were then expanded for 6 days in the presence of IL-2 with anti-CD3/anti-CD28 Dynabeads (Xcyte Technologies) to induce the proliferation necessary to incorporate $^{51}$Cr. A $^{51}$Cr incorporation experiment prior to bead expansion of the CD3+ cells confirmed that $^{51}$Cr uptake was extremely poor (data not shown), suggesting a negligible number of surviving blasts in the pre-expansion population. After bead expansion, examination of the cell population by light microscopy also confirmed that few, if any, surviving blasts were present in the expanded CD3+ population. Using these non-leukemic targets, the ability of CTLs primed by dendritic cells doubly-loaded with the same patient's leukemic antigens to lyse the non-leukemic targets were assessed. FIG. 9A demonstrates that effectors primed by doubly-loaded dendritic cells can efficiently lyse allogeneic leukemic blasts but cannot lyse the non-leukemic CD3+ controls (HLA-identical to the blasts) ($p<0.0001$). This experiment was performed on three independent occasions using two different normal donors. Results were comparable. Shown is a representative experiment. FIG. 9B depicts a similar experiment in the autologous setting. Here, effectors primed by doubly-loaded dendritic cells lyse autologous AML-loaded dendritic cell targets but cannot lyse the autologous unloaded controls ($p<0.002$). These results strongly suggest that CTL lysis can be dependent upon antigens provided by the tumor mRNA and lysate and need not be dependent upon alloreactivity or non-specific interaction between effector and target. While the lack of alloreactivity in the allogeneic setting may seem somewhat surprising, it should be pointed out that normal donor lymphocytes used in the system were partially HLA-matched with the allogeneic leukemic blasts and were also selected based upon empirical pre-screening for relatively low levels of alloreactivity with these blasts. The normal donor was typed as HLA A03/24, B35/35, and C01/01. The leukemic donor was typed as HLA A31/31, B15/35, and C01/04. Class II HLA typing was not available.

To further explore the role that class I antigenic specificity might play in specific lysis, dendritic cells were loaded with AML lysate, then subsequently electroporated them with either matched AML mRNA or mismatched mRNA derived from an irrelevant murine cell line, FBMD-1 (fetal bone marrow derived). Lytic effectors were then generated by dendritic cell priming and restimulation of autologous T-cells. As demonstrated in FIG. 7C, substitution of AML mRNA with FBMD-1 mRNA completely abrogated lysis of matched AML blast targets ($p<0.000002$), further demonstrating the specificity of effectors produced by doubly-loaded dendritic cells. In addition, abrogation of lysis by effectors primed with FBMD-1 mRNA suggested that cytotoxic effects were primarily MHC class I-mediated.

Example 2

Materials and Methods

Generation of Immature Dendritic Cells, Preparation of Antigenic Materials, DC Loading and Maturation.

DC were generated as described previously from cryopreserved, normal donor, G-CSF mobilized PBPCs donated for research under MD Anderson IRB protocol #Lab02-630.(3) Cellular tumor antigens were prepared as described previously.(3) HLA-restricted peptide sequences derived from the sequence of the Influenza A/New Calcdonia HA antigen were generated and characterized as described.(11) Immature DC were loaded with either tumor lysate, tumor mRNA, both, or neither as described previously.(3) Conditions for delivering single antigens (i.e., single proteins and/or plasmids) were identical unless stated otherwise. DC were loaded with one of two different protein antigens [eGFP (Invitrogen) or mIL-4 (eBioscience, San Diego, Calif.)] by incubation of cells in 100 µg/ml antigen for three hours followed by the electroporation of at least 1 plasmid DNA/$10^6$ cells. When loaded with peptides, immature DC were incubated for 90 minutes at a concentration of 10 µg/ml per peptide. DC were then matured for 2 hours in GM-CSF, IL-4, IL-113, TNF-a, IL-6, and PGE2 (ITIP) after which they were washed thoroughly in PBS to remove excess peptide. DC were then resuspended in AIM-V supplemented with GM-CSF, IL-4, and ITIP and matured for an additional 30 to 36 hours. If loaded in the presence of ethanolamine, ethanolamine was added in conjunction with the peptide epitopes at concentrations between 0.04% and 0.08% (6.7 to 13.3 mM). Ethanolamine was thoroughly washed off the mature DC before the advent of T-cell stimulation.

Transcriptome Analysis.

DC preparations were pooled according to the manner by which they had been loaded. Total RNA was then generated as described (Decker et al., 2006) from unloaded preparations, mRNA-loaded preparations, lysate-loaded preparations, matched, doubly-loaded preparations, and mismatched, doubly-loaded preparations. The five total RNA samples were used to probe the Human Genome U133 Plus 2.0 Array (Affymetrix, Santa Clara, Calif.) in duplicate (ten arrays total) in conjunction with Codon Biosciences, LP (Houston, Tex.). For comparison of transcript expression levels, Cohen's d was calculated for each transcript by the method of pooled standard deviation using the root mean square of the standard deviations: $d=(M_1-M_2)/\sqrt{(\sigma_1^2+\sigma_2^2)/2}$. Transcripts of matched, doubly-loaded dendritic cells were identified as differentially-regulated if they conformed to Cohen's>1.0 (large effect) and q-value (Benjamini-Hochberg false discovery)<0.01. Functional class analysis of transcripts was performed using the data mining software WEBGESTALT(12) MIAME-compliant microarray data is freely available in the GEO database (on the world wide web at ncbi.nlm.nih.gov/geo/), Accession #GSE7247.

CTLA-4 RT-PCR and IL-12 ELISA.

cDNA of differentially loaded DC populations was generated from total RNA pools using the SMART cDNA Synthesis Kit (Clontech, Mountain View, Calif.) according to the manufacturer's instructions. Exon 2 of CTLA-4 was amplified from DC cDNA with forward primer 5'-TGGCCCAGC-CTGCTGTGG-3' (SEQ ID NO:1) and reverse primer 5'-TCTGGGTTCCGTTGCCTATG-3' (SEQ ID NO:2) for 25 or 30 cycles, annealing at 58° C. IL-12 ELISA was performed as described previously. (Decker et al., 2006)

Statistical Analysis.

Statistical differences were calculated by Student's unpaired two-tailed t-test unless stated otherwise. Significance was defined as $p<0.05$. Error bars in all figures=±SD unless otherwise indicated.

Results

DC IL-12 Secretion and CD83 Expression are Regulated by Loading with Matched Class I and Class II Antigens.

Figure 10:
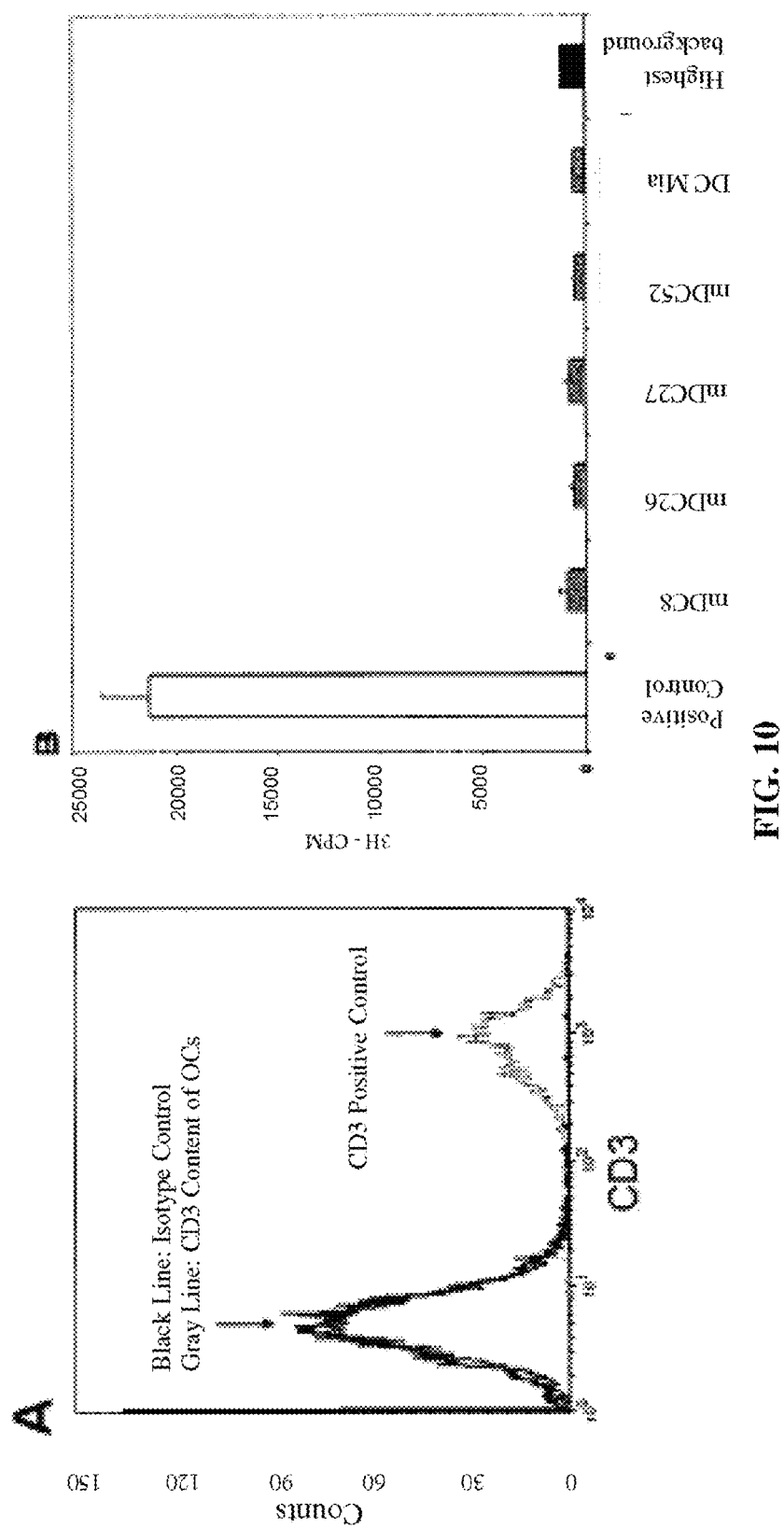
FIGS. 10A-B. DC cultures are devoid of accessory CD3+ cells. A. Solid black line=CD3 staining; solid gray line=isotype control staining. Dotted line=CD3 positive control. B. White bar=positive alloreactive control. Gray bars=DC cultures. Black bar=assay background.

In order to confirm cell-autonomous DC phenomena, the absence of accessory T-cells in dendritic cell cultures was demonstrated. Following monocyte isolation and ex vivo tissue culture for eight days, cell cultures were completely devoid of CD3+ cells as determined by flow cytometry (e.g., FIG. 10A) subsequently, up to four different allogeneic populations of DCs were mixed together in an attempt to detect the presence of contaminating T-cells by alloreactive stimulus. $^3$H-thymidine uptake in mixed DC wells was indistinguishable from that of the assay background (FIG. 10B). From these data it was concluded that DC populations were effectively devoid of accessory CD3+ cells. DCs utilized in subsequent experiments were also verified to be fee of CD3+ cells by flow cytometry.

It was previously reported that doubly-loaded DCs secrete the Th-1 cytokine IL-12 at much higher levels than their unloaded and singly-loaded counterparts (Decker et al., 2006). To demonstrate that upregulation of IL-12 secretion is specific to the presence of matched MHC class I and MHC class II antigenic determinants, the well-characterized, multi-antigen system was departed from (Decker et al., 2006; Decker et al., 2008; Decker W K and Schpall, 2008; Decker et al., 2006) developing a simple, single antigen system. Utilizing GFP as a model antigen and the murine isoform of IL-4 (biologically inactive in human systems) as an irrelevant, unmatched antigen, immature DCs were loaded by electroporation of GFP or mIL-4 expression plasmids, incubation with protein antigen, both plasmid and protein, or neither. Following maturation, DC IL-12 secretion was determined by ELISA of culture supernatants. FIG. 2A demonstrates that only DCs loaded with identical class I (expression plasmid) and class II (purified recombinant protein) antigens exhibited upregulation of IL-12 secretion over weak baseline. Singly-loaded and mismatched doubly-loaded DCs did not exhibit significant IL-12 secretion (p<0.001, representative experiment shown). This result was reproducible within this particular system as well as within a different system in which endogenous GFP was delivered by recombinant retroviral vector and the irrelevant soluble antigen was luciferase (p<0.03, data not shown).

Figure 11:
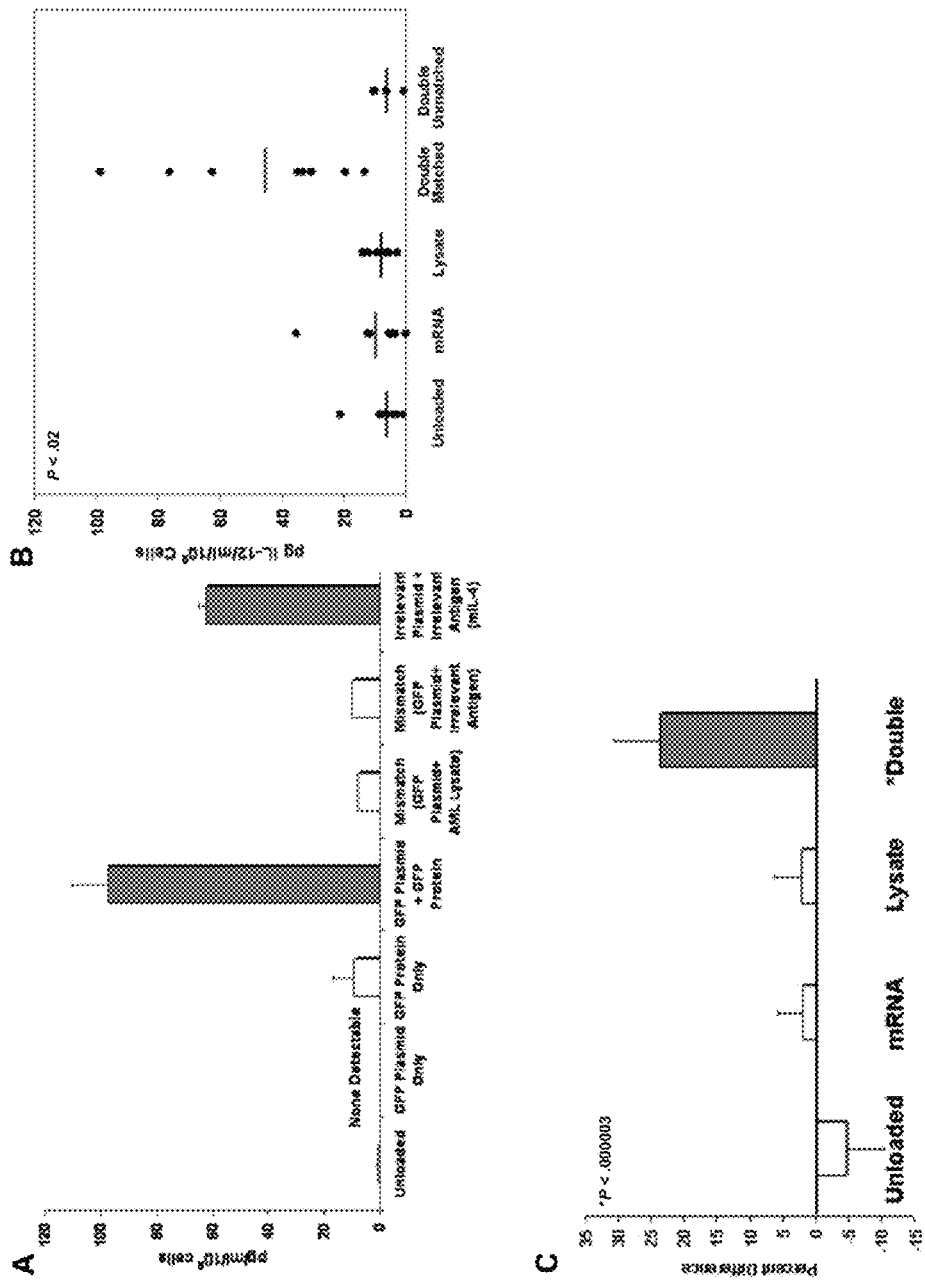
FIGS. 11A-C. A. Double-loading of DCs with matched MHC class I and II determinants enhances dendritic cell IL-12 secretion in a single-antigen system. Gray bar=IL-12 secretion from dendritic cells loaded with matched class I (plasmid) and class II (soluble protein). White bars=IL-12 secretion from other DC loaded by any other method. Y axis=pg IL-12/ml/$10^6$ cells (both A and B). B. Double-loading of DCs with matched MHC class I and II antigens enhances dendritic cell IL-12 secretion. Eight experiments shown (double unmatched—five experiments shown). C. Double-loading of DC with matched class I and II determinants causes enhanced upregulation of CD83 expression. Average value of unloaded and singly-loaded DCs=0. White bars=percent by which CD83 expression of all unloaded or singly-loaded DCs differs from the average. Gray bar=percent by which CD83 expression of all doubly-loaded DCs differs from the average ($p<0.000003$). Y axis=percent difference of CD83 expression from the average of unloaded and singly-loaded DCs.

Returning to the model system of AML immunotherapy, IL-12 secretion was characterized from DC singly-loaded with tumor mRNA, singly-loaded with tumor lysate, doubly-loaded with mRNA and lysate derived from the same tumor product, or doubly-loaded with tumor mRNA and a lysate derived from disparate tissues (human erythroid or xenogenic stromal cell lines). Following maturation, culture supernatants were examined for IL-12 (p70) secretion by ELISA. FIG. 11B demonstrates that only DCs loaded with mRNA and lysate taken from the same tumor or cell line (p<0.02) were able to produce markedly elevated levels of IL-12 secretion. Results were derived from eight independent experiments using a variety of different normal donors. Results were in good agreement with similar experiments reported previously. (Decker et al., 2006)

CD83 is one of the most consistent indicators of dendritic cell maturity. Upon maturation, its expression is upregulated on the DC's surface from undetectable levels pre-maturation. (Lechmann et al., 2002) CD83 is a sialic acid-binding Ig-like lectin adhesion receptor (Scholler et al., 2001) vitally important in the development of CD4+ T-cells (Garcia-Martinez, 2001) as well as in the promulgation of productive CD8+ T-cell responses. (Lechmann et al., 2002; Garcia-Martinez et al., 2004; Lechmann et al., 2001; Zinser et al., 2004; Kobelt et al., 2003; Scholler et al., 2002; Aerts-Toegaert et al., 2007) Soluble CD83 blocks both allogeneic and autologous CD8+ T-cell proliferation in a concentration dependent manner in vitro, and its administration abolishes experimental autoimmune encephalomyelitis by downregulating T-cell responses in vivo. (Lechmann et al., 2001; Zinser et al., 2004) While phenotyping preparations of DCs, it was noted that doubly-loaded DCs always expressed higher levels of CD83 than singly-loaded controls. To characterize CD83 surface expression, CD83 surface expression of doubly-loaded versus singly-loaded were compared and unloaded dendritic cells following maturation. In eight independent experiments (FIG. 11C), CD83 expression was 24% higher among doubly-loaded dendritic cells (p<0.000003) than among the mean expression level of all singly-loaded and unloaded controls. Examination of other surface markers did not demonstrate this pattern of upregulation, suggesting that this phenomenon was not artifactual (data not shown).

Figure 12:
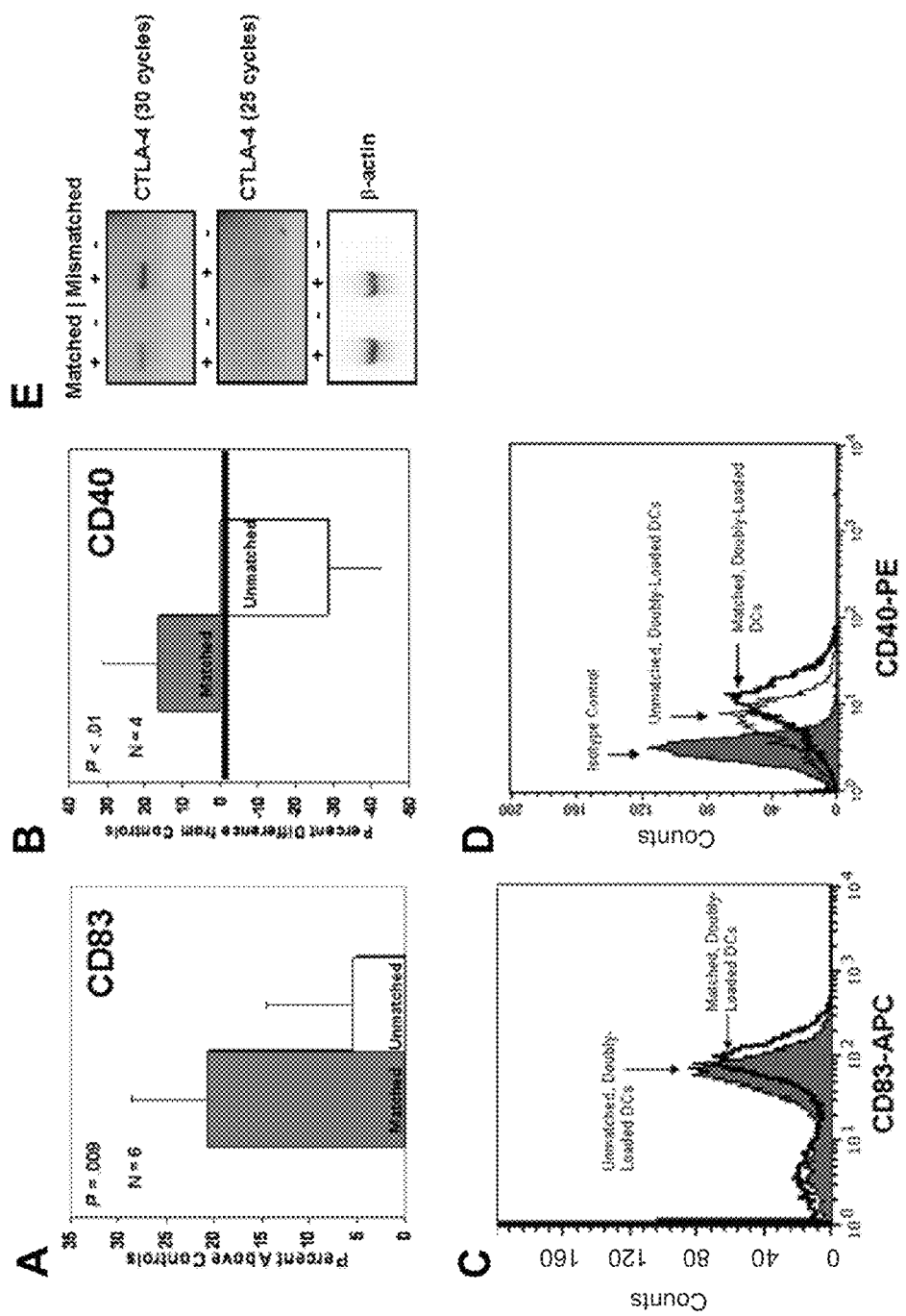
FIGS. 12A-E. Differential regulation of CD83, CD40, and CTLA-4 is dependent upon the double-loading of DCs with matched class I and II antigens. A. Percent difference of CD83 expression from average of unloaded and singly-loaded controls between matched doubly-loaded (gray bar) and unmatched doubly-loaded (white bar) DCs ($p=0.009$). Y axis=percent difference from average of unloaded and singly-loaded controls. B. Same as 3A but with CD40 staining rather than CD83 ($p<0.01$). C-D. Histograms demonstrating representative results for A (CD83) and B (CD40). E. Semi-quantitative RT-PCR demonstrates differential expression of CTLA-4 between DCs doubly-loaded with matched antigens and DCs doubly-loaded with mismatched antigens. Matched=DC loaded with matched class I and II antigens. Mismatched=DC loaded with mismatched class I and II antigens. +/−=+/− reverse transcriptase.

To test the hypothesis that the enhanced upregulation of DC CD83 was specific to loading with matched class I and class II antigenic determinants, DCs were loaded with matched mRNA and lysate (derived from the same tumor product) or with unmatched determinants derived from disparate combinations of AML tumor products, the human TF-1 a erythroblast cell line, or the mouse FBMD-1 stromal cell line. Singly-loaded controls in each experiment were loaded with the AML-derived antigenic determinant(s). Enhanced upregulation of CD83 among the matched and unmatched doubly-loaded DC populations was then compared to average CD83 expression levels of unloaded and singly-loaded controls independently in each of six different experiments. As demonstrated in FIG. 12A, DCs doubly-loaded with matched determinants exhibited a 21% enhancement of CD83 upregulation while DCs loaded with unmatched determinants exhibited an enhancement of only 5.5% (p=0.009), statistically indistinguishable from the 2-3% upregulation observed among singly-loaded controls. A typical flow cytometry overlay of this phenomenon is shown by FIG. 12C.

DC Loaded with Overlapping Class I and II HLA Binding Peptides Support Enhanced Th-1 Lymphocyte Responses.

While these data suggested DC autonomous phenomena, it could be argued that, in the absence of specific, defined MHC class I and class II binding peptides, the data are difficult to interpret. It might further be argued that, in a total antigen system, the DC-specific phenomenon of cross-presentation (Heath et al., 2004) renders impossible any discernment that important MHC class I epitopes were derived from a pool of mRNA or from an expression plasmid. In order to address these potential concerns and to remove the phenomenon of cross presentation as a confounding variable, a model system was developed comprised solely of HLA-restricted binding peptides derived from the hemagglutinin antigen (HA) of Influenza A/New Caledonia. The positioning of the peptides along the primary HA sequence is illustrated in FIG. 13A. In this new model system, HLA-compatible DC were loaded phagocytically with class I and II peptides for 90 minutes, after which the peptides were washed away, and the DC were matured for 30-36 hours. Because the half life of MHC class I is only 4 hours, the majority of any peptide antigen bound by surface MHC class I during the loading process is gone after the 36 hour maturation. Hence, differences in the abilities of differentially-loaded DCs to prime Th-1 responses are due to signals that were sent following the initial loading process 36 hours earlier. After maturation, DC were co-cultured with autologous T-cells, and the ability of DC to support Th-1 responses was assayed by IFN-γ release and flow cytometry of proliferating T-cells.

Figure 14:
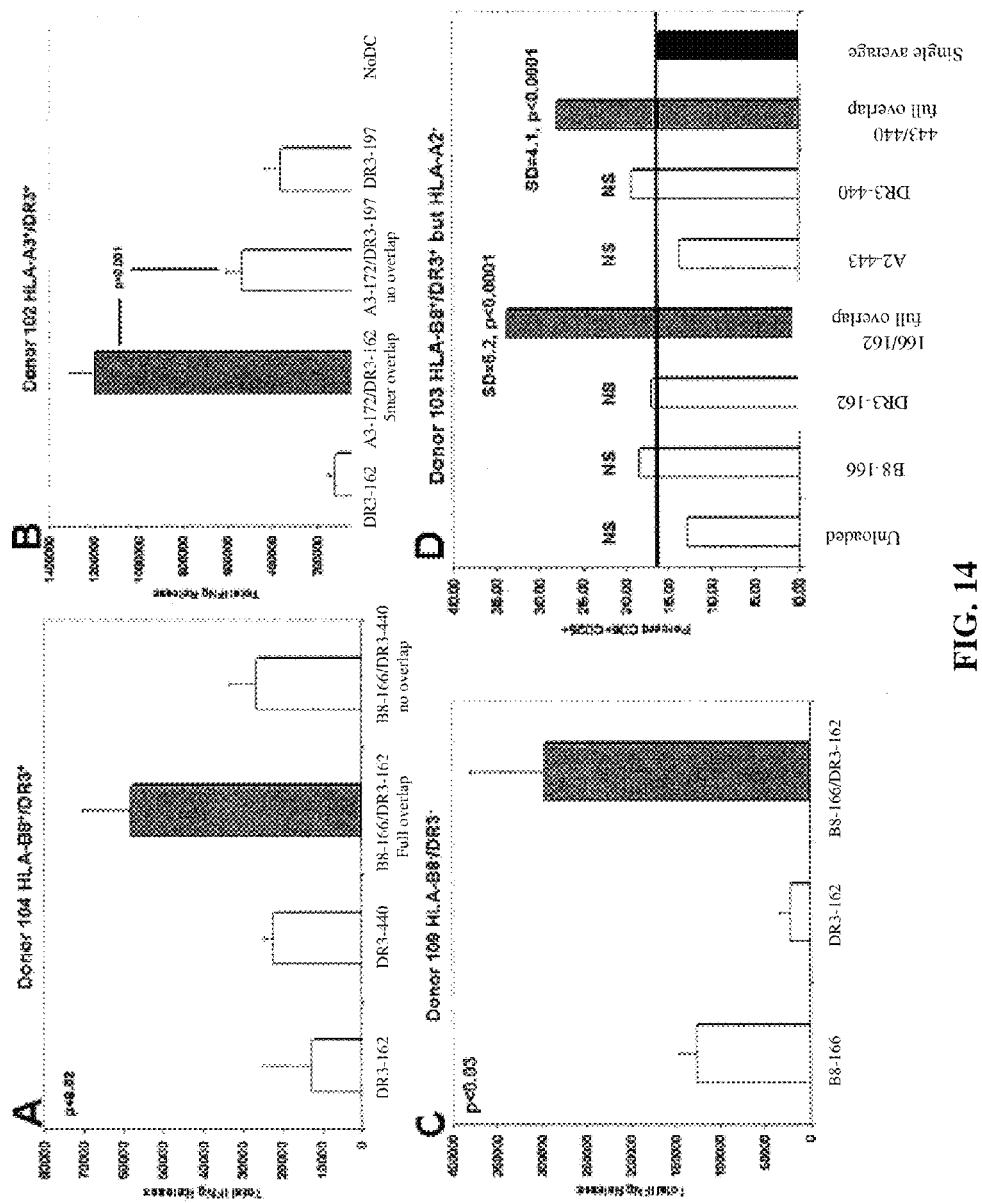

FIG. 14A illustrates a representative IFN-γ release experiment in which DC loaded with overlapping class I (B8-162) and class II (DR3-166) peptides stimulated the secretion of excess IFN-γ from autologous T-cells in comparison to DC loaded with the same class I peptide (B8-162) and a non-overlapping class II peptide (DR3-440). Indeed, IFN-γ release stimulated by DC loaded with non-overlapping peptides was indistinguishable from singly-loaded class II controls (p<0.02). In similar series of experiments, the inventors sought to determine if a partial sequence overlap between class I and II epitopes would be sufficient to enhance the release of IFN-γ. In the representative experiment illustrated by FIG. 14B, DC loading with class I and II peptides that overlapped by five amino acid residues (A3-172/DR3-162) was still sufficient to promote enhanced IFN-γ secretion. An overlap of 2 residues was insufficient to elicit enhanced IFN-γ production (data not shown). With repeated experiments in both HLA-compatible and HLA-disparate donor backgrounds, the inventors were able to demonstrate that stringent HLA-matching between defined peptide epitope and donor was helpful, but not always an absolute requirement for all peptides (e.g., FIG. 14C). Such a result is predictable given the high concentration at which the binding peptides were loaded (10 μg/ml) and the likely existence of multiple HLA binding affinities to undefined haplotypes.

Ultimately, DC doubly-loaded with overlapping class I and II peptides had to demonstrate the ability to expand CD8+ T-cells to levels significantly different from unloaded DC, singly-loaded DC, or DC doubly-loaded with non-overlapping class I and II peptides. In FIG. 14D, this reproducible phenomenon is demonstrated. DC loaded with overlapping class I and II peptides (e.g. B8-166/DR3-162 and A2-443/DR3-440) were able to induce and support much higher levels of activated CD8+ T-cells than DC loaded by other methods (p<0.0001).

DCs Loaded with Matched Class I and II Antigenic Determinants Exhibit a Unique Transcriptional Signature.

According to the hypothesis, DCs doubly-loaded with matched class I and II antigens should exhibit a unique functional phenotype with, presumably, a correspondingly unique transcriptional signature differing from that of DC loaded by any other method. To investigate this hypothesis, a substantial analysis of the DC transcriptome was performed using extensive controls and stringent statistical inclusion criteria. Following loading by one of five different methods (unloaded control, mRNA-loaded only control, lysate loaded only control, mismatched mRNA/lysate doubly-loaded control, and the matched mRNA/lysate doubly-loaded experimental group), DCs were matured for 48 hours and cryopreserved. Matured DCs from at least six distinct individual donors were then pooled together according to the method by which they had been loaded. RNA was isolated from pooled DCs, and samples were analyzed in duplicate using the Affymetrix U133 Plus 2.0 Array, a human genome microarray containing over 54,000 transcripts (GEO Ascension GSE7247). Expression concordance among sample duplicates averaged 99.2%. Cohen's d (a measure of effect size) was calculated for each transcript, and transcripts that differed in expression level between matched, doubly-loaded DC and all of the other four control groups were identified as differentially-expressed if they stringently conformed to Cohen's>1.0 (large effect is >0.8) and q-value (Benjamini-Hochberg false discovery value)<0.01. Given the stringent statistical parameters, the likelihood that any given gene has been identified in error is at most 1%.

DCs loaded with matched class I and II determinants did indeed exhibit a unique transcriptional signature in comparison to unloaded DCs and DCs loaded by any other method, including double loading with mismatched class I and II determinants. Data illustrate the top 100 genes that were differentially regulated between DC doubly-loaded with matched class I and II determinants and the four control groups. Cohen's for these genes ranged from 17.1 to 7.7. A full genetic signature of 1,750 differentially-expressed genes as defined by the statistical inclusion criteria. A majority of these differentially-expressed genes were downregulated.

Differentially Regulated Genes of DCs Doubly-Loaded with Matched Class I and II Antigens Promote Th-1 Polarization.

According to the understanding, known genes identified as differentially-regulated among DCs doubly-loaded with matched class I and II determinants should be related in some fashion to the promotion of Th-1 type cellular immunity. To examine this issue, differentially-expressed genes with immune-related functions were identified by the data-mining software WEBGESTALT, and Cohen's d values for each identified transcript were independently reviewed to verify low standard deviations between experimental and controls groups. This analysis revealed 43 immune-related genes involved with cell survival, antigen presentation, T-cell regulation, anti-viral responses, and T-helper polarization (Table 1). Significantly, the results demonstrated both a substantial upregulation of some class I presentation components and a significant downregulation of the class II presentation machinery including the CIITA transcriptional activator. Antiviral, Th-1 promoting, and IFN-inducible responses were significantly upregulated. Genes involved in the generation of humoral immunity were significantly downregulated.

TABLE 1

| Gene | Regulation | Cohen's [d] | q | Function |
|---|---|---|---|---|
| Cell Survival | | | | |
| TNFRSF5 | Down | 8.67 | <0.002 | Induction of Cell Death |
| IL-2Rβ | Up | 7.73 | <0.008 | Inhibition of Cell Death |
| IL-1α | Down | 4.76 | <0.002 | Multiple (Including Survival) |
| CLU (2) | Up | 3.38 | <0.001 | Multiple (Including Survival) |
| Antigen Presentation | | | | |
| IGλ Locus | Up | 6.72 | <0.0007 | MHC I Antigen Presentation |
| IGHμ | Up | 4.14 | <0.008 | MHC I Antigen Presentation |
| HLA-DRβ1/DRβ3 | Down | 3.80 | <0.004 | MHC II Antigen Presentation |
| HLA-DQα1 (2) | Down | 3.33 | <0.00006 | MHC II Antigen Presentation |
| CITA | Down | 3.32 | <0.001 | MHC II Antigen Presentation (TF) |
| CD1b | Up | 3.03 | <0.0003 | Lipid Antigen Presentation |
| HLA-DQβ1 (2) | Down | 2.99 | <0.0002 | MHC II Antigen Presentation |
| GtP2 | Up | 2.71 | <0.0002 | IFNα-Inducible Signal Transeductions |
| CBLB (2) | Down | 2.24 | <0.002 | Ubiquitination |

TABLE 1-continued

| Gene | Regulation | Cohen's [d] | q | Function |
|---|---|---|---|---|
| T-Cell Regulation | | | | |
| CTLA-4 (2) | Down | 3.32 | <0.0003 | Induction of T-cell Allergy |
| CD40 (2) | Up | 2.57 | <0.0006 | CD8+ T-cell Priming |
| IL-23α | Dowm | 1.84 | <0.00002 | Inhibition of CD8+ Responses |
| Anti-Viral Response | | | | |
| TRIM22 | UP | 3.74 | <0.001 | Anti-Viral Response (TF) |
| PRKRA | Down | 3.54 | <0.0006 | dsRNA Anti-Viral Response |
| CTBP1 | Down | 3.04 | <0.006 | Viral Genome Regulations |
| IRF1 | Down | 2.37 | <0.004 | Regulations of IFN-Inducible Response |
| MX2 | Up | 2.32 | <0.0008 | Anti-Viral Response |
| MX1 | Up | 2.08 | <0.0004 | Anti-Viral Response |
| CCL4 | Down | 1.74 | <0.004 | Chemotaxis & Viral Replication |
| IFI27 | Up | 1.69 | <0.004 | IFN-Inducible Immune Response |
| GBP2 | Down | 1.53 | <0.002 | IFN-Inducible Immune Response |
| T-Helper Polarization | | | | |
| TLR-4 | Up | 4.50 | <0.004 | Pathogen Detection & Upreg. of Th-1 Responses |
| PTAFR | Down | 4.02 | <0.002 | Humoral Immunity |
| COLEC12 | Down | 3.92 | <0.003 | Humoral Immunity |
| LILR-B2 | Down | 3.82 | <0.0002 | Humoral Immunity |
| LY9 | Down | 3.48 | <0.002 | Humoral Immunity |
| CCL26 | Down | 5.14 | <0.0000007 | Th-2 Response (Eosinophil Chemotaxis) |
| MYD68 | Up | 3.12 | <0.002 | TLR Signal Transduction |
| Other Immune-Related | | | | |
| DCLRE1C | Down | 5.49 | <0.0008 | DNA Damage Repair |
| XBP1 | Down | 2.83 | <0.0005 | Transcription Factor |
| IL-1R1 | Down | 2.52 | <0.0004 | Signal Transduction |
| MS4A1 | Up | 2.52 | <0.01 | Intracellular Signal Transduction |
| FUS | Down | 2.27 | <0.002 | Nucleic Acid Binding |
| OAS2 | Up | 2.14 | <0.0005 | Microsomal Nuclsic Acid Metabolism |
| LST1 (2) | Up | 2.04 | <0.004 | Dendrite Morphogenesis |
| C1Qβ | Up | 1.88 | <0.0006 | Complement Activation |
| CRH | Down | 1.88 | <0.0006 | Synaptic Transmission |
| LIL-RA3 | Up | 1.34 | <0.001 | Antigen Binding |
| C1Qα | Up | 1.32 | <0.004 | Complement Activation |

Of special note, both CD40 and CTLA-4 were shown to be differentially-regulated. CD40 is a critical DC surface molecule, the stimulation of which permits "licensing" of CD8+ responses by DC if stimulated by a CD4+ helper T-cell expressing CD40L. (23-28) In contrast, CTLA-4 suppresses CD8+ T-cell responses, causing T-cell anergy by a variety of hypothesized mechanisms including CD28 antagonism and/or inhibitory signaling. Interestingly, CTLA-4 has not previously been shown to be expressed by DCs, but principally by regulatory CD4+ T-cells. (29) When class I and II antigens were matched, dendritic cells upregulated CD40 expression and downregulated CTLA-4 expression. In addition, WEB-GESTALT analysis demonstrated that more than 2% of the differentially-regulated genes were directly involved in ubiquitination, a key step in class I antigen processing (Table 2).

The differential expression of CD40 was verified with expression data as determined by flow cytometry. In four independent experiments (FIGS. 12B and 12D), it was demonstrated that CD40 surface expression varied significantly between matched doubly-loaded DCs (15% above the mean of the unloaded/singly-loaded controls) and unmatched, doubly-loaded DCs (30% below the mean of unloaded/singly-loaded controls; p<0.01). Consistent with the literature, CTLA-4 expression was not detected on the DC surface, nor was it detectable intracellularly. Moreover, the addition of autologous T-cells was unable to stimulate expression of CTLA-4 on the DC surface in a manner analogous to B-lymphocytes as reported by Kuiper. (Decker et al., 2006) Given these data, it was contemplated that DCs might be secreting the soluble, secreted isoform of CTLA-4 (sCTLA-4) which lacks the exon 3-encoded transmembrane domain. (Oaks et al., 2000) Accordingly, differential CTLA-4 expression in DC RNA pools was confirmed by semi-quantitative RT-PCR (FIG. 3E), demonstrating high levels of sCTLA-4 expression when class I and II determinants were mismatched and low levels of sCTLA-4 expression when class I and II determinants were matched.

TABLE 2

| Ubiquitin Metabolism | | | | |
|---|---|---|---|---|
| Gene | Regulation | Cohen's [d] | q | Function |
| RFP2 | Down | 8.28 | <0.0008 | Ubiquitin ligation |
| BIRC4 | Down | 7.74 | <0.007 | Ubiquitin ligation |
| USP40 | Down | 7.56 | <0.009 | Ubiquitin-Dependent Protein Catabolism |
| EDEM1 | Down | 7.49 | <0.00006 | Enhancer of ER Protein Catabolism |
| MDM4 | Down | 7.26 | <0.0002 | Ubiquitin ligation |
| UCHL1 | Up | 7.01 | <0.00002 | Deubiquitination |
| TRIP12 | Down | 6.89 | <0.0003 | Ubiquitin ligation |

TABLE 2-continued

Ubiquitin Metabolism

| Gene | Regulation | Cohen's [d] | q | Function |
|---|---|---|---|---|
| USP4 | Down | 6.73 | <0.004 | Ubiquitin-Dependent Protein Catabolism |
| RNF44 | Down | 6.69 | <0.002 | Transcriptional Regulation |
| MAP3K7IP2 (2) | Down | 6.63 | <0.0005 | Signal Transduction |
| MAP3K1 | Down | 6.38 | <0.0003 | Signal Transduction |
| FBXL3 | Down | 5.70 | <0.002 | Ubiquitin ligation |
| TRIM56 | Down | 5.69 | <0.007 | Ubiquitin ligation |
| FLJ13855 | Down | 5.62 | <0.0005 | Ubiquitin ligation |
| TRIM50B | Down | 5.44 | <0.0002 | Ubiquitin ligation |
| UBE2B (2) | Down | 5.28 | <0.002 | Ubiquitin ligation |
| MAR7 | Down | 5.16 | <0.001 | Unknown |
| UBE3C | Down | 5.15 | <0.01 | Ubiquitin ligation |
| UBE2D3 (3) | Down | 5.13 | <0.0002 | Ubiquitin ligation |
| SENP6 | Down | 5.00 | <0.004 | Ubiquitin-Dependent Protein Catabolism |
| FLJ31951 | Down | 4.57 | <0.0008 | Unkoown |
| ANAPC5 | Down | 4.38 | <0.0003 | Ubiquitin ligation |
| PARK2 | Down | 4.07 | <0.006 | Ubiquitin ligation |
| VCPIP1 | Up | 3.82 | <0.008 | Signal Transduction |
| TRIM22 | Up | 3.74 | <0.001 | Transcriptional Regulation |
| PSMB2 | Up | 3.61 | <0.002 | Ubiquitin-Dependent Protein Catabolism |
| SENP8 | Up | 3.59 | <0.007 | Ubiquitin-Dependent Protein Catabolism |
| BIRC6 | Down | 3.25 | <0.003 | Ubiquitin ligation |
| RNF34 | Down | 3.03 | <0.003 | Ubiquitin ligation |
| TBL1X (3) | Down | 2.92 | <0.0003 | Signal Transduction |
| G1P2 | Up | 2.71 | <0.0002 | IFN-Inducible Signal Transduction |
| PRPF19 | Down | 2.66 | <0.00003 | Ubiquitin ligation |
| KIAA0317 | Up | 2.64 | <0.01 | Ubiquitin ligation |
| UBE2I | Down | 2.44 | <0.004 | Ubiquitin ligation |
| C17orf27 | Down | 2.30 | <0.003 | Ubiquitin ligation |
| CBLB (3) | Down | 2.24 | <0.008 | Ubiquitin ligation |
| TSG101 | Up | 2.22 | <0.002 | Transcriptional Regulation |
| FBXO6 | Up | 2.12 | <0.0006 | Generalized Ubiquitination |
| USP18 | Up | 2.10 | <0.0007 | Ubiquitin-Dependent Protein Catabolism |
| MYLIP (2) | Down | 1.55 | <0.004 | Ubiquitin ligation |

Glycyl-tRNA Synthetase Inhibitor Ethanolamine Implicates Aminoacyl-tRNA Synthetases as Components of a "Recognisome" Sensor Complex.

Having thoroughly demonstrated that the loading of dendritic cells with "matched" or overlapping MHC class I and II determinants is sufficient to elicit a significant Th-1 polarization, it becomes necessary to develop mechanistic hypotheses that can adequately accommodate this observation. Obviously, such mechanisms must be somewhat speculative at this juncture.

Aminoacyl-tRNA synthetases and their associated tRNA molecules possess the alluring molecular qualities required by a "sensor" system capable of discerning sequence similarities among short peptide epitopes: each tRNA-synthetase is capable of recognizing the amino acid residue for which it is specific, and identical tRNAs are capable of stably recognizing each other via Watson-Crick base-pairing of their extensive stem-loop structures. Again, much anecdotal and experimental evidence exists to support such a hypothesis. It has been reported that the level of extracytoplasmic (microsomal) aminoacyl-tRNA synthetase activity in both human and mouse leukocytes is at least as great as the cytoplasmic tRNA-synthetase activity associated with mRNA translation. (Agris et al., 1976) Further, a substantial body of evidence suggests that tRNA-synthetases and tRNAs very frequently come into close contact with the MHC antigen presentation machinery. Both tRNA-synthetases and tRNAs are the major autoantigens of a wide variety of autoimmune diseases including myositis, systemic lupus erythematosus, interstitial lung disease, and rheumatoid arthritis. (Mathews and Bernstein, 1983; Bunn et al., 1986; Dang et al., 1988; Targoff et al., 1993; Vartanian, 1991; Arnett et al., 1996; Beaulande et al., 1998; Ohosone et al., 1998; Ioannou et al., 1999; Becker et al., 1999) Moreover, the transcriptome analysis revealed that eight tRNA-aminoacyl synthetases were differentially regulated among DC doubly-loaded with matched class I and II determinants (data not shown). Partly on the basis of these considerations, the hypothesis that a "recognisome" might form between MHC class I and MHC class II in the post-lysosomal microsome was generated and further hypothesized that sequence comparisons within this "recognisome" could be mediated by extracytoplasmic tRNAs and/or their associated tRNA synthetases reported by Agris. To examine this, a model system to demonstrate the participation of tRNAs/tRNA synthetases in the process was developed by which the DC compares the sequence similarity of loaded class I and class II epitopes. This model system was able to further emphasize that the generation of Th-1 responses against specific epitopes is highly dependent upon amino acid sequence similarities between class I and class II antigens.

Ethanolamine is the alcohol derivative of the amino acid glycine, i.e., its 3' carboxyl group has been replaced with a hydroxyl moiety. Ethanolamine specifically inhibits glycyl-tRNA synthetase by blocking the first step of glycine aminoacylation, the conversion of glycine and ATP to glycyl-adenylate. Thus, ethanolamine traps glycyltRNA synthetase complexed with its substrate molecules and terminates further reaction. (Arnez et al., 1999) Because ethanolamine competitively inhibits only glycyl-tRNA synthetase, it is possible to specifically block the generation of Th-1 responses by DC loaded with glycine-containing class I/class II peptides by the addition of ethanolamine during loading and maturation. Th-1 responses generated by glycine-free overlapping class I and II epitopes should remain unaffected by the presence of ethanolamine. To utilize such a system, the B8-166/DR3-162 class I/class II peptide pair was taken advantage of, possessing two glycine residues in the sequence overlap region, and the A2-443/DR3-440 peptide pair which possesses no glycine residues in the overlap region (as outlined in FIG. 13B). Because ethanolamine can also inhibit protein synthesis, independent experiments were necessary to establish the proper concentration of ethanolamine for experimentation (range 0.1% to 0.01%, data not shown). Experiments were performed identically to the previous peptide experiments with the exception that 0.04-0.08% ethanolamine was added during loading and maturation. No ethanolamine was present after mature DC harvest and during T-cell stimulation. Following stimulation, T-cells were phenotyped by flow cytometry to determine the ability of peptide-loaded DC to support the proliferation of CD8 cells.

Figure 15:
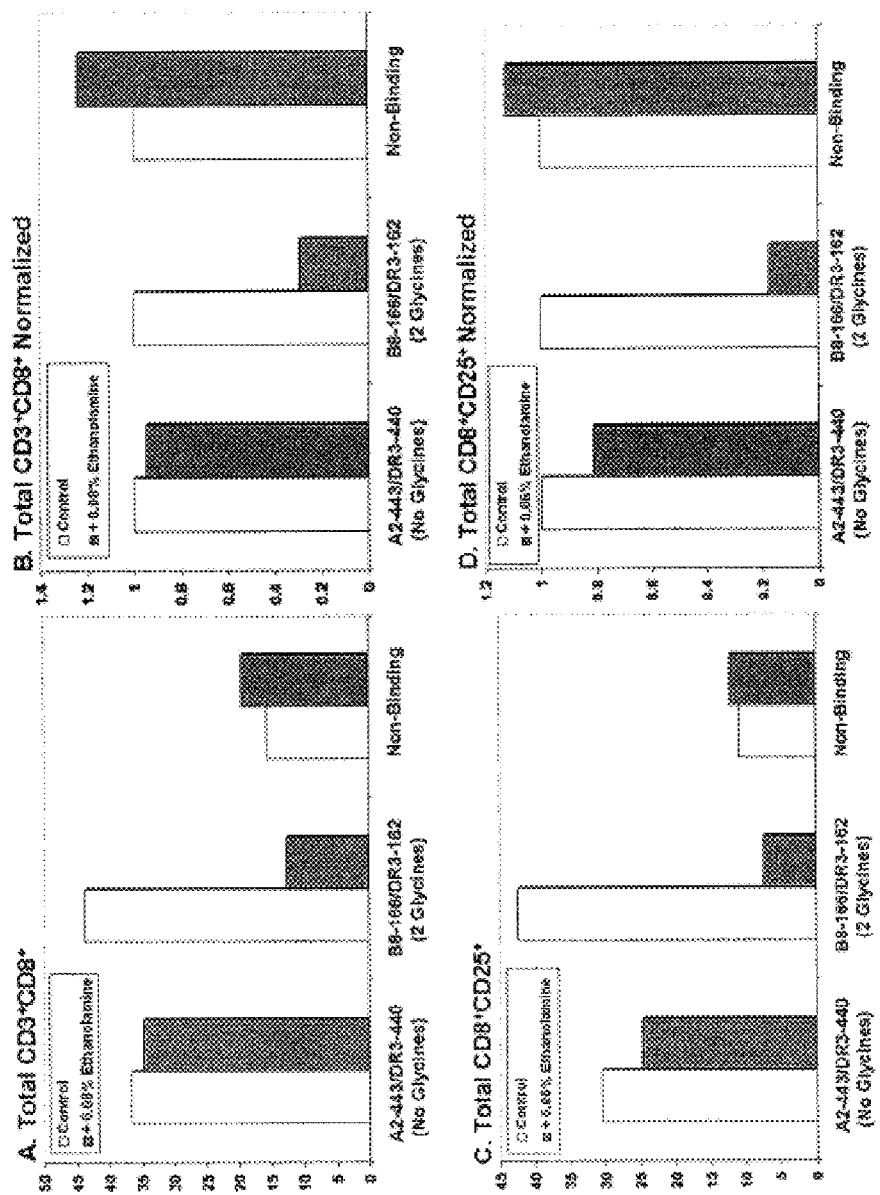

As contemplated, ethanolamine had no effect upon the ability of DC doubly-loaded with non-glycine containing peptides to support the proliferation of CD8+ T-cells. In contrast, DC loaded with peptides containing glycine residues in class I/II sequence overlap region were profoundly affected by the presence of 0.04%-0.08% ethanolamine. The representative experiment depicted by FIGS. 15A and 15B demonstrates that the presence of ethanolamine during DC loading and maturation resulted in a 71% reduction in the number of CD3+CD8+ T-cells (43.7% to 12.7% total CD3+CD8+) generated by the overlapping class I/II peptide pair B8-166/DR3-162 (2 glycine residues in the overlap region). In contrast, DC loaded with the A2-443/DR3-440 peptide pair (no glycine residues in the overlap region) maintained high production levels of CD3+CD8+ cells in either the presence (34.9%) or absence (36.6%) of ethanolamine. DC loaded with nonbinding control peptides also produced CD3+CD8+ cells at equivalent levels in either the presence or absence of ethanolamine and allowed discernment of background CD3+CD8+ levels. A second representative experiment demonstrates equivalent results in the production of activated CD8+ cells (CD8+CD25+). As demonstrated by FIGS. 15C and 15D, the presence of ethanolamine during DC loading and maturation resulted in an 83% reduction in the number of CD8+CD25+ T-cells (42.4% to 7.3% total CD8+CD25+) generated by the overlapping class I/II peptide pair B8-166/DR3-162. Ethanolamine treatment did not induce a similar reduction in CD8+CD25+ generation by A2-443/DR3-440-loaded DC (30.4% vs. 24.8%) nor DC loaded with non-binding peptides (10.7% vs. 12.1%).

Example 3

Materials and Methods

Mice.

Six week old male Balb/c animals were obtained from Harlan Laboratories (Indianapolis, Ind.) and maintained in accordance with IACUC requirements at Baylor College of Medicine.

Preparation of Antigenic Materials.

Prostate and seminal vesicle (SV) were harvested from male mice and immediately frozen at −80° C. To generate cell lysates or mRNA, tissue fractions were first disrupted using a Polytron PT1200E tissue homogenizer (Kinematica, Inc, Bohemia, N.Y.). To generate cell lysates, homogenized tissue suspensions were diluted to 50 mg/ml in PBS (Life Technologies, Carlsbad, Calif.) and subjected to repetitive freeze-thaw cycles. Lysates were clarified by centrifugation and stored at −20° C. Total RNA was isolated from homogenized tissues using Trizol reagent (Life Technologies) according to the manufacturer's instructions, and mRNA was isolated from total RNA using an Oligotex mRNA Maxi Kit (Qiagen, Valencia, Calif.), also according to the manufacturer's instructions. mRNA was quantitated by UV spectroscopy and stored at −20° C.

Preparation and Loading of Dendritic Cells.

Splenocytes were harvested on two separate occasions from a total of 25 Balb/c mice and were adhered for in T300 flasks (Phenix Research, Candler N.C.) in RPMI-1640 (Life Technologies) supplemented with 10% mouse serum (Equitech Bio, Kerrville, Tex.) and 1% penicillin/streptomycin/amphotericin B (Anti-anti, Life Technologies). After two hours of adherence, the non-adherent fraction was removed, and both adherent and non-adherent fractions were cultured in RPMI-1640 supplemented with mouse serum, anti-anti, 30 ng/ml rmGM-CSF (R&D Systems, Minneapolis, Minn.), 10 ng/ml rmIL-4 (R&D Systems), and 100 ng/ml rhFlt3-L (R&D Systems). After three days of culture, the medium was removed and replaced with fresh medium supplemented as described previously but without rhFlt3-L. After an additional three days in culture (six days total), newly adherent cells derived from the non-adherent fraction as well as the original adherent fraction were harvested by incubation in cold PBS and subsequent incubation in Cell Dissociation Buffer (Life Technologies). Immature dendritic cells were characterized by staining with antibodies against CD8a, CD11c, CD80, CD83, and CD86 (all purchased from BD Biosciences, San Jose, Calif.) and subsequent analysis by flow cytometry. Immature DC were first loaded with prostate or SV mRNA by resuspension in Viaspann (Barr Laboratories, Pomona, N.Y.) at a concentration of $4 \times 10^7$/ml and incubated for 10 min on ice in an electroporation cuvette with an 0.4 cm gap (Biorad, Hercules, Calif.). Cells were then electroporated at 250V, 125 µF, and $\Omega = \infty$ using a GenePulser Xcell (Biorad). Electroporated cells were incubated for three hours in serum-free RPMI-1640 supplemented only with anti-anti and 2 mg/ml tissue lysate, then washed and matured overnight in RPMI-1640 supplemented with 10% mouse serum, 1% anti-anti, 30 ng/ml rmGM-CSF, 10 ng/ml rmIL-4, 10 ng/ml rmL-1β (R&D Systems), 10 mg/ml rmTNF-α (R&D Systems), 15 ng/ml rmIL-6 (R&D Systems), and 1 µg/ml $PGE_2$ (Sigma-Aldrich, St. Louis, Mo.). In addition, some maturing DC were also supplemented with 3,000 U/ml rmIFN-α (PBL, Piscataway, N.J.). After overnight maturation, DC were harvested, characterized by flow cytometry, and resuspended at $5 \times 10^6$/ml for injection.

Vaccination.

The day before the primary vaccination some mice were pretreated intraperitoneally with 100 µg anti-CD25 (BD Biosciences) to ablate regulatory T-cell populations. The following day, all mice were vaccinated intraperitoneally with $5 \times 10^5$ DC, and some mice were also contemporaneously injected intraperitoneally with 1 mg TLR-7 agonist imiquimod (LC Labs, Woburn, Mass.) suspended but not solubilized in 20% DMSO/80% RPMI-1640. Hence one mouse each was vaccinated as follows:

1. Anti-CD25+$5 \times 10^5$ prostate-loaded DC+1 mg imiquimod
2. $5 \times 10^5$ prostate-loaded DC+1 mg imiquimod
3. $5 \times 10^5$ prostate-loaded DC
4. Anti-CD25+$5 \times 10^5$ prostate-loaded, IFN-α matured DC+1 mg imiquimod
5. $5 \times 10^5$ prostate-loaded, IFN-α matured DC+1 mg imiquimod
6. $5 \times 10^5$ prostate-loaded, IFN-α matured DC
7. Anti-CD25+$5 \times 10^5$ SV-loaded, IFN-α matured DC+1 mg imiquimod
8. $5 \times 10^5$ SV-loaded, IFN-α matured DC+1 mg imiquimod
9. $5 \times 10^5$ SV-loaded, IFN-α matured DC
10. Unvaccinated Mice were vaccinated once every ten days for a total of four cycles of vaccination. Serum was harvested by retroorbital bleed in conjunction with each vaccination as well as 10 and 20 days after the final vaccination.

PSP94 ELISA.

Serum samples are analyzed for alterations in PSP94, a mouse secretory protein with prostate-specific expression. Briefly, ELISA plates are coated overnight with 100 ng anti-PSP94 rabbit polyclonal antibody (Santa Cruz Biotechnology, Santa Cruz, Calif.). The following day, plates are incubated for one hour with 95 µl of a ten-fold dilution of each serum sample. Detection is performed by incubating primary anti-PSP94 polyclonal antibody at a 40-fold molar excess with anti-rabbit/HrP (Jackson Immunoresearch, West Grove, Pa.) in 500 µl total volume at 37° C. for one hour, followed by incubation of the ELISA wells with the primary/secondary bound conjugates at 100 ng/primary antibody per well.

Histological Analysis.

Fifty to sixty days following the original vaccination, mice are sacrificed, and male reproductive organs are harvested. Intact organs are fixed in 10% formalin, paraffin-embedded, and sectioned in 5 µM increments. Paraffin sections are stained with hematoxylin and eosin for gross histological analysis by light microscopy.

Results

Figure 16:
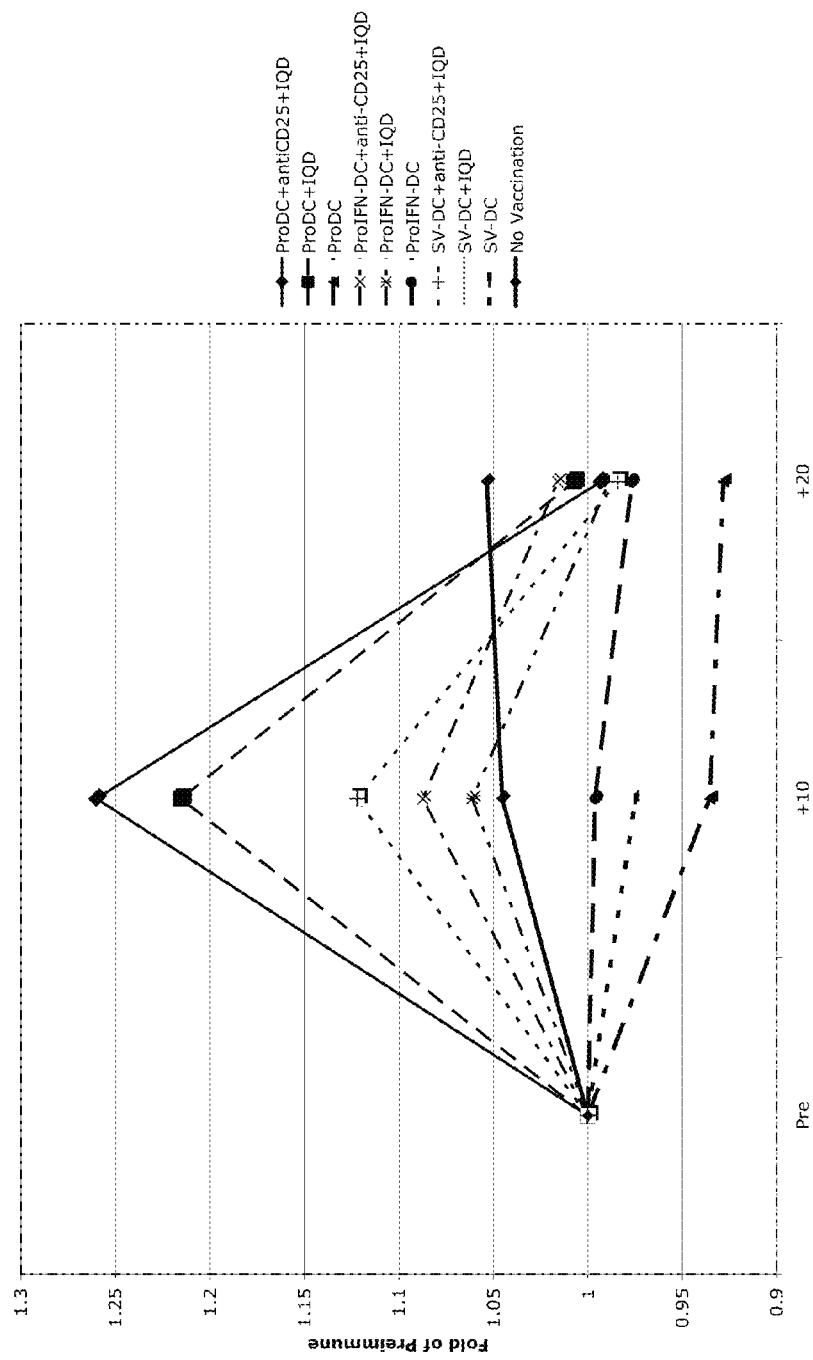
Figure 17:
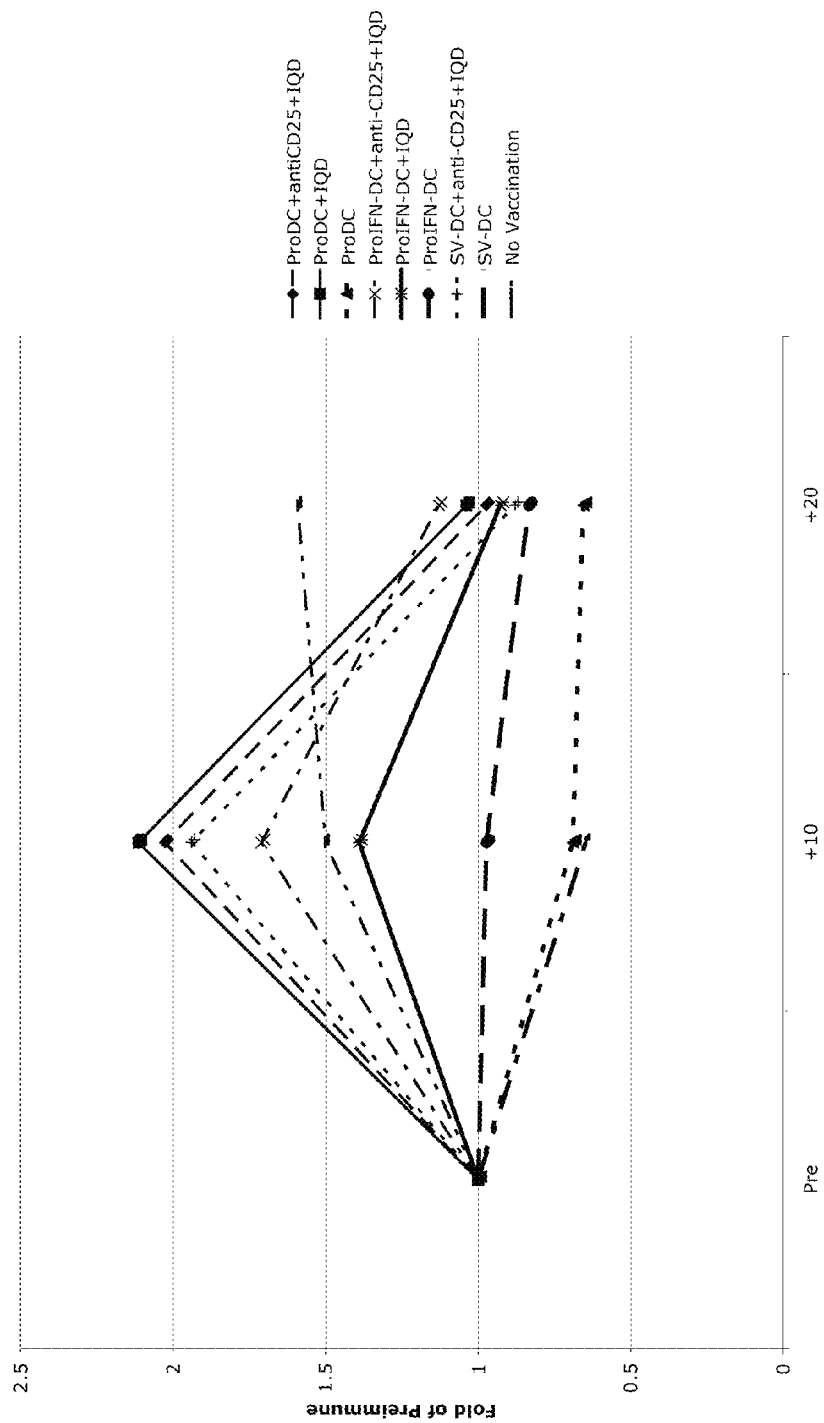

An interim analysis following the third vaccination examined serum samples taken on days 0, +10, and +20. Serum levels of PSP94 were elevation on day +10 (in comparison to pre-vaccine levels) followed by a decline on day +20 to levels below that observed in pre-vaccine samples. PSP94 levels in the unvaccinated animal demonstrated neither a marked elevation on day +10 nor a decrease in serum levels on day +20. The results are consistent with the interpretation of prostate damage on day +10 and a trend towards decreased production of PSP94 (hence decreased amounts of remaining prostate tissue) on day +20. The data are presented in FIGS. 16 and 17 as a normalization to pre-vaccination levels of PSP94 in each individual mouse, both with and without background correction.

Example 4

Human Studies

Clinical Protocol.

Before enrolling patients, the protocol will be reviewed and approved by the Food and Drug Administration and other appropriate federal, state, and University entities. Patients aged 18 or older will be eligible to participate. Eastern Cooperative Oncology Group performance status of 0 to 2, and adequate organ function (WBC, >3,000/mm$^3$; ANC, >1,500/mm$^3$; platelets, >100,000/mm$^3$; hematocrit, >25%; bilirubin, <2.0 mg/dL; and creatinine, <2.0 mg/dL) are required. Patients with a preexisting autoimmune disorder, an immunodeficiency condition, or a serious ongoing infection are not eligible.

Vaccines are produced, and administered by intradermal injection at four separate sites that drain to the bilateral axillary and inguinal lymph node basins. This is repeated on three separate occasions every 2 weeks. Two weeks after the third set of vaccines, the patients are re-staged. Those patients who do not exhibit progressive disease at this point undergo a second leukapheresis procedure, and received three additional sets of vaccines, this time every 4 weeks. Patients who develop progressive disease after the third or sixth vaccination are offered additional cytotoxic chemotherapy.

Vaccine Production.

Mononuclear cells for DC production are obtained after leukapheresis and stored in liquid nitrogen. After thawing, cells are placed in X-VIVO-15 medium (Biowhittaker, Walkersville, Md.) in tissue culture flasks at a concentration of 1.3 to 1.7×10$^6$ cells/cm$^2$ of available culturing surface. After 2 hours of culture, nonadherent cells are removed and the flasks are recharged with X-VIVO-15 medium supplemented with 5 ng/mL granulocyte macrophage colony-stimulating factor (Amgen, Thousand Oaks, Calif.) and 5 ng/mL interleukin-4 (R&D Systems, Minneapolis, Minn.). The flasks are incubated for 48 hours, at which time additional cytokine-supplemented medium is added to the flasks. The flasks are then incubated for an additional 72 hours. At the completion of incubation, the nonadherent and loosely adherent cells are collected and doubly loaded with a tumor antigen composition and/or a a nucleic acid composition as described herein. At the end of loading, X-VIVO medium is added to a final cell concentration of 10$^6$ cells/mL, and cells are incubated in flasks for an additional 46 hours, at which time the cells are harvested, washed, and analyzed. Vaccine release criteria includes, (a) negative Gram's staining, (b) negative *Mycoplasma* test by PCR analysis, (c) maximum endotoxin concentration of 5 EU/mL, and (d) a mature DC phenotype with evidence of maturation by flow cytometry analysis. Mature DC phenotype is defined as lineage (CD3, CD14, CD19, CD20, and CD56)-negative, HLA-DR-positive, and (CD83 and CD86)-positive cells.

Analysis of IFN-γ-Producing Cells in ELISPOT Assays.

Peripheral blood mononuclear cells are collected from patients prior vaccination, 2 to 3 weeks after completion of the third vaccination (postvaccine time point), and then 2 months later. Samples are kept in aliquots in liquid nitrogen. Samples from each patient are thawed and analyzed simultaneously. Th-1 dendritic cells are prepared as described herein and are seeded in quadruplicate in complete culture medium supplemented with interleukin-2 (1×10$^5$ cells/well) in 96-well plates precoated with an anti-IFN-γ antibody and incubated for 36 hours. The number of IFN-γ-producing cells is evaluated using an automated ELISPOT reader (CTL).

Phenotype and Function of T Cells and DCs.

After thawing, the mononuclear cells are cultured overnight in complete culture medium supplemented with 10% FCS. Cell phenotype is evaluated by multicolor flow cytometry using a FACSCalibur flow cytometer and monoclonal antibodies obtained from Becton Dickinson (Franklin Lakes, N.J.).

To evaluate T cell proliferation, mononuclear cells are cultured in triplicate in U-bottomed 96-well plates in the presence of 0.1 µg/mL tetanus toxoid or 5 µg/mL phytohemagglutinin (Sigma, St. Louis, Mo.). $^3$H-thymidine (1 µCi) is added on day 3 and cells are harvested 18 hours later. Thymidine incorporation is evaluated using a liquid scintillation counter. The stimulation index is calculated as the ratio between cell proliferation in the presence versus absence of stimuli. To evaluate DC function, responder T cells are isolated from control donors using T cell enrichment columns (R&D Systems). T cells are cultured with mononuclear cells obtained from cancer patients in U-bottomed 96-well plates. T cells with mononuclear cell ratios from 1:1 to 1:8 are used. All experiments are done in triplicate. $^3$H-thymidine (1 µCi) was added on day 3, and cells were harvested 18 hours later. Thymidine incorporation was evaluated using liquid scintillation counter. Each mononuclear cell sample is tested against T cells from at least two different donors and the maximum result is used.

REFERENCES

The following references, to the extent that they provide exemplary procedural or other details supplementary to those set forth herein, are specifically incorporated herein by reference.

Banchereau J, Palucka A K. Dendritic cells as therapeutic vaccines against cancer. Nat Rev Immunol 2005; 5(4):296-306.

Banchereau J, Paczesny S, Blanco P, Bennett L, Pascual V, Fay J, et al. Dendritic cells: controllers of the immune system and a new promise for immunotherapy. Ann N Y Acad Sci 2003; 987: 180-7.

Hartgers F C, Figdor C G, Adema G J. Towards a molecular understanding of dendritic cell immunobiology. Immunol Today 2000; 21(11):542-5.

Steinman R M, Hawiger D, Nussenzweig M C. Tolerogenic dendritic cells. Annu Rev Immunol 2003; 21:685-711.

Chang A E, Redman B G, Whitfield J R, Nickoloff B J, Braun T M, Lee P P, et al. A phase I trial of tumor lysate-pulsed dendritic cells in the treatment of advanced cancer. Clin Cancer Res 2002; 8(4):102132.

Geiger J D, Hutchinson R J, Hohenkirk L F, McKenna A, Yanik G A, Levine J E, et al. Vaccination of pediatric solid tumor patients with tumor lysate-pulsed dendritic cells can expand specific T cells and mediate tumor regression. Cancer Res 2001; 61(23):8513-9.

Nestle F O, Alijagic S, Gilliet M, Sun Y, Grabbe S, Dummer R, et al. Vaccination of melanoma patients with peptide- or tumor lysatepulsed dendritic cells. Nat Med 1998; 4(3): 328-32.

Heiser A, Coleman D, Dannull J, Yancey D, Maurice M A, Lallas C D, et al. Autologous dendritic cells transfected with prostate specific antigen RNA stimulate CTL responses against metastatic prostate tumors. J Clin Invest 2002; 109(3):409-17.

Nair S K, Morse M, Boczkowski D, Cumming R1, Vasovic L, Gilboa E, et al. Induction of tumor-specific cytotoxic T lymphocytes in cancer patients by autologous tumor RNA-transfected dendritic cells. Ann Surg 2002; 235(4):540-9.

Morse M A, Coleman R E, Akabani G, Niehaus N, Coleman D, Lyerly H K. Migration of human dendritic cells after injection in patients with metastatic malignancies. Cancer Res 1999, 59(I):56-8.

Gilboa E, Vieweg J. Cancer immunotherapy with mRNA-transfected dendritic cells. Immunol Rev 2004; 199:251-63.

Banchereau J, Palucka A K, Dhodapkar M, Burkeholder S, Taquet N, Rolland A, et al. Immune and clinical responses in patients with metastatic melanoma to CD34(+) progenitor-derived dendritic cell vaccine. Cancer Res 2001; 61(17):6451-8.

Toungouz M, Libin M, Bulte F, Faid L, Lehmann F, Duriau D, et al. Transient expansion of peptide-specific lymphocytes producing IFN-gamma after vaccination with dendritic cells pulsed with MAGE peptides in patients with mage-A1/A3-positive tumors. J Leukoc Biol 2001; 69(6):937-43.

Tjoa B A, Simmons S J, Bowes V A, Radge H, Rogers M, Elgamel A, et al. Evaluation of phase I/II clinical trials in prostate cancer with dendritic cells and PSMA peptides. Prostate 1998; 36(1):39-44.

Timmerman J M, Czerwinski D K, Davis T A, Hsu F J, Benike C, Hao Z M, et al. Idiotype-pulsed dendritic cell vaccination for B-cell lymphoma: clinical and immune responses in 35 patients. Blood 2002; 99(5): 1517-26.

Titzer S, Christensen O, Manzke O, Tesch H, Wolf J, Emmerich B, et al. Vaccination of multiple myeloma patients with idiotype-pulsed dendritic cells: immunological and clinical aspects. Br J Haematol 2000; 108(4):805-16.

Lim S H, Bailey-Wood R. Idiotypic protein-pulsed dendritic cell vaccination in multiple myeloma. Int J Cancer 1999; 83(2):215-22.

Tozer R G, McCulloch P B, Dent P, et al. Vaccination with autologous CD34+ derived dendritic cells transduced with an adenovirus expressing human gp100 in patients with metastatic melanoma. Proc Am Soc Clin Oncol 2002; 21:352a.

Haluska F G, Linette G P, Jonasch E, et al. Immunologic gene therapy of melanoma: phase I study of therapy with autologous dendritic cells transduced with recombinant adenoviruses encoding melanoma antigens. Proc Am Soc Clin Oncol 2000; 19:453a.

Tham E L, Shrikant P, Mescher M F. Activation-induced nonresponsiveness: a Th-dependent regulatory checkpoint in the CTL response. J Immunol 2002; 168(3):1190-7.

Behrens G, Li M, Smith C M, Belz G T, Mintem 0.1, Carbone F R, et al. Helper T cells, dendritic cells and CTL immunity. Immunol Cell Biol 2004; 82(1):84-90.

Rocha B, Tanchot C. Towards a cellular definition of CD8+ T-cell memory: the role of CD4+ T-cell help in CD8+ T-cell responses. Curr. Opin Immunol 2004; 16(3):259-63.

Wolkers M C, Brouwenstijn N, Bakker A H, Toebes M, Schumacher T N. Antigen bias in T cell cross-priming. Science 2004; 304(5675):1314-7.

Zinkemagel R M. On cross-priming of MHC class I-specific CTL: rule or exception? Eur J Immunol 2002; 32(9):2385-92.

Ochsenbein A F, Sierro S, Odermatt B, Pericin M, Karrer U, Her-mans J, et al. Roles of tumour localization, second signals and cross priming in cytotoxic T-cell induction. Nature 2001; 411(6841):105864.

Lowenberg B, Downing J R, Burnett A. Acute myeloid leukemia. N Engl J Med 1999; 341(14):1051-62.

Ries L A G, Eisner M P, Kosary C L, editors. SEER Cancer Statistics Review, 1975-2001. Bethesda, Md.: National Cancer Institute; 2004. http://seer.cancer.gov/csr/1975_2001/.

Smith M, Barnett M, Bassan R, Gatta G, Tondini C, Kern W. Adult acute myeloid leukaemia. Crit. Rev Oncol Hematol 2004; 50(3):197-222.

Drobyski W R. The role of allogeneic transplantation in high-risk acute myelogenous leukemia. Leukemia 2004; 18(10): 1565-8.

Hu X, Moscinski L C, Hill B J, Chen Q, Wu J, Fisher A B, et al. Characterization of a unique factor-independent variant derived from human factor-dependent TF-1 cells: a transformed event. Leuk Res 1998; 22(9):817-26.

Xing D, Decker W K, Yang H, et al. Acute Myeloid Leukemia Lysate Loaded Dendritic Cells Exhibit Significant Phagocytic Function and Elicit Antigen-Specific Immune Response. Blood 2004; 104: 693a.

Su Z, Dannull J, Yang B K, Dahm P, Coleman D, Yancey D, et al. Telomerase mRNA-transfected dendritic cells stimulate antigen-specific CD8+ and CD4+ T cell responses in patients with metastatic prostate cancer. J Immunol 2005; 174(6):3798-807.

Bedrosian I, Mick R, Xu S, Nisenbaum H, Faries M, Zhang P, et al. Intranodal administration of peptide-pulsed mature dendritic cell vaccines results in superior CD8+ T-cell function in melanoma patients. J Clin Oncol 2003; 21(20): 3826-35.

You Z, Huang X F, Hester J, Rollins L, Rooney C, Chen S Y. Induction of vigorous helper and cytotoxic T cell as well as B cell responses by dendritic cells expressing a modified antigen targeting receptor-mediated internalization pathway. J Immunol 2000; 165(8):4581-91.

Ridgway D. The first 1000 dendritic cell vaccinees. Cancer Invest 2003; 21(6):873-86.

Galea-Lauri J, Darling D, Mufti G, Harrison P, Farzaneh F. Eliciting cytotoxic T lymphocytes against acute myeloid leukemia-derived antigens: evaluation of dendritic cell-leukemia cell hybrids and other antigen-loading strategies for dendritic cell-based vaccination. Cancer Immunol Immunother 2002; 51(6):299-310.

Banat G A, Usluoglu N, Hoeck M, Ihlow K, Hoppmann S, Pralle H. Dendritic cells fused with core binding factor-beta positive acute myeloid leukaemia blast cells induce activation of cytotoxic lymphocytes. Br J Haematol 2004; 126(4):593-601.

Caux C, Massacrier C, Vanbervliet B, Dubois B, Van Kooten C, Durand I, et al. Activation of human dendritic cells through CD40 cross-linking. J Exp Med 1994; 180(4):1263-72.

Bennett S R, Carbone F R, Karamalis F, Flavell R A, Miller J F, Heath W R. Help for cytotoxic-T-cell responses is mediated by CD40 signalling. Nature 1998; 393(6684):478-80.

Schoenberger S P, Toes R E, van der Voort E I, Offringa R, Melief C J. T-cell help for cytotoxic T lymphocytes is mediated by CD40CD40L interactions. Nature 1998; 393 (6684):480-3.

Ribas A, Butterfield L H, Amarnani S N, Dissette V B, Kim D, Meng W S, et al. CD40 cross-linking bypasses the absolute requirement for CD4 T cells during immunization with melanoma antigen gene-modified dendritic cells. Cancer Res 2001; 61 (24):8787-93.

van Mierlo G J, Boonman Z F, Dumortier H M, den Boer A T, Fransen M F, Nouta I, et al. Activation of dendritic cells that cross-present tumor-derived antigen licenses CD8+ CTL to cause tumor eradication. J Immunol 2004; 173(11):6753-9.

Janeway C A, Travers P, Hunt S, Walport M. Immunobiology: the immune system in health and disease. 3rd ed. New York, N.Y.: Garland Publishing, Inc; 1997.

Bourgeois C, Rocha B, Tanchot C. A role for CD40 expression on CDS' T cells in the generation of CD8* T cell memory. Science 2002; 297(5589):2060-3.

Shinde S, Wu Y, Guo Y, Niu Q, Xu J, Grewal I S, et al. CD40L is important for induction of, but not response to, costimulatory activity. ICAM-1 as the second costimulatory molecule rapidly up-regulated by CD40L. J Immunol 1996; 157(7):2764-8.

Lindgren C G, Thompson J A, Robinson N, Keeler T, Gold P J, Fefer A. Interleukin-12 induced cytolytic activity in lymphocytes from recipients of autologous and allogeneic stem cell transplants. Bone Marrow Transplant 1997; 19(9):867-73.

Bennett S R, Carbone F R, Karamalis F, Miller J F, Heath W R. Induction of a CD8* cytotoxic T lymphocyte response by cross-priming requires cognate CD4* T cell help. J Exp Med 1997; 186(1):6570.

Sakaguchi S, Naturally arising CD4* regulatory t cells for immunologic self-tolerance and negative control of immune responses. Annu Rev Immunol 2004; 22:531-62.

Wahl S M, Swisher J, McCartney-Francis N, Chen W. TGF-beta: the perpetrator of immune suppression by regulatory T cells and suicidal T cells. J Leukoc Biol 2004; 76(1):15-24.

Weigle W O, Romball C G. CD4* T-cell subsets and cytokines involved in peripheral tolerance. Immunol Today 1997; 18(11): 533-8.

Spisek R, Chevallier P, Morineau N, Milpied N, Avet-Loiseau H, Harousseau J L, et al. Induction of leukemia-specific cytotoxic response by cross-presentation of late apoptotic leukemic blast by autologous dendritic cells of nonleukemic origin. Cancer Res 2002; 62(10):2861-8.

Dendritic Cells, 2nd Edition. Lotze M T, Thompson A W, eds. Academic Press: London: 2001.

Immunobiology: The Immune System in Health and Disease, 3rd Edition. Janeway C A, Travers P, Hunt S, Walport M, eds. Garland Publishing: New York: 1997.

Decker W K, Xing D, Li S, et al. Double Loading of Dendritic Cell MHC Class I and MHC Class II with an AML Antigen Repertoire Enhances Correlates of T-cell Immunity In Vitro via Amplification of T-cell Help. Vaccine. 2006; 24:3203-3216.

Lekkerkerker A N, van Kooyk Y, Geijtenbeek T B. Viral Piracy: HIV-1 Targets Dendritic Cells for Transmission. Curr HIV Res. 2006; 4:169-176.

Becker Y. Immunological and Regulatory Functions of Uninfected and Virus Infected Immature and Mature Subtypes of Dendritic Cells—a Review. Virus Genes. 2003; 26:119-130.

Decker W K, Li S, Xing D, et al. Deficient Th-1 Responses from TNF-a-Matured and a-CD40-Matured Dendritic Cells. J Immunother. 2008; 31:157-165.

Decker W K, Shpall E J. Progress in dendritic cell immunotherapy: Elucidating the enigma of Th-1 polarization. Hum Vaccin. 2008; 4:1-3.

Lopez C B, Fernandez-Sesma A, Schulman J L, Moran T M. Myeloid dendritic cells stimulate both Th1 and Th2 immune responses depending on the nature of the antigen. J Interferon Cytokine Res. 2001; 21:763-773.

Lopez C B, Moltedo B, Alexopoulou L, et al. TLR-Independent Induction of Dendritic Cell Maturation and Adaptive Immunity by Negative-Strand RNA Viruses. J. Immunol. 2004; 173:6882-6889.

Hornung V J, Schlender J, Guenthner-Biller M, et al. Replication-dependent potent IFN-alpha induction in human plasmacytoid dendritic cells by a single-stranded RNA virus. J. Immunol. 2004; 172:5935-5943.

Safdar A, Decker W K, Li S, Shpall E J, Bollard C M. De Novo T-Lymphocyte Responses against Baculovirus-derived Recombinant Influenzavirus Hemagglutinin Generated by a Naive Umbilical Cord Blood Model of Dendritic Cell Vaccination. Submitted.

Zhang B, Kirov S, Snoddy J. WEBGESTALT: An integrated system for exploring gene sets in various biological contexts. Nucleic Acids Res. 2005; 33:W741-W748.

Decker W K, Xing D, Shpall Dendritic Cell Immunotherapy for the Treatment of Neoplastic Disease. Biol Blood Marrow Transplant. 2006; 12:113-125.

Lechmann M, Bertold S, Hauber J, Steinkasser A. CD83 on dendritic cells: more than just a marker for maturation. Trends Immunol. 2002; 23:273-275.

Scholler N, Hayden-Ledbetter M, Hellstrom K E, Hellstrom I, Ledbetter J A. CD83 Is a Sialic Acid-Binding Ig-Like Lectin (Siglec) Adhesion Receptor that Binds Monocytes and a Subset of Activated CD8+ T Cells. J. Immunol. 2001; 166:3865-3872.

Garcia-Martinez L F, Appleby M W, Staehling-Hampton K, et al. A Novel Mutation in CD83 Results in the Development of a Unique Population of CD4+ T Cells. J. Immunol. 2004; 173:2995-3001.

Lechmann M, Krooshoop D J, Dudziak D, et al. The Extracellular Domain of CD83 Inhibits Dendritic Cell-mediated T Cell Stimulation and Binds to a Ligand on Dendritic Cells. Exp Med. 2001; 194:1813-1821.

Zinser E, Lechmann M, Golka A, Lutz M B, Steinkasserer A. Prevention and treatment of experimental autoimmune encephalomyelitis by soluble CD83. J Exp Med. 2004; 200:345-351.

Kobelt D, Lechmann M, Steinkasserer A. The interaction between dendritic cells and herpes simplex virus-1. Curr Top Microbiol Immunol. 2003; 276:145-161.

Scholler N, Hayden-Ledbetter M, Dahlin A, et al. Cutting Edge: CD83 Regulates the Development of Cellular Immunity. J. Immunol. 2002; 168:2599-2602.

Aerts-Toegaert C, Heirman C, Tuyaerts S, et al. CD83 expression on dendritic cells and T cells: Correlation with effective immune responses. Eur J. Immunol. 2007; 37:686-695.

Heath W R, Belz G T, Behrens G M, et al. Cross-presentation, dendritic cell subsets, and the generation of immunity to cellular antigens. Immunol Rev. 2004; 199:9-26.

Shedlock D J, Shen H. Requirement for CD4 T-cell help in generating functional CD8 T-cell memory. Science. 2003; 300:337-339.

Janssen E M, Lemmens E E, Wolfe T, et al. CD4+ T-cells are required for secondary expansion and memory in CD8+ T-lymphocytes. Nature. 2003; 421:852-856.

Bennett S R M, Carbone F R, Karamalis F, Miller J F, Heath W R. Induction of a CD8+ Cytotoxic T Lymphocyte Response by Cross-priming Requires Cognate CD4+ T Cell Help. J Exp Med. 1997; 186:65-70.

Bennett S R M, Carbone F R, Karamalis F, et al. Help for cytotoxic-T-cell responses is mediated by CD40 signalling. Nature. 1998; 393:478-480.

Schoenberger S P, Toes R E, van der Voort E I, Offringa R, Melief C J. T-cell help for cytotoxic T lymphocytes is mediated by CD40-CD40L interactions. Nature. 1998; 393:480-483.

Behrens G, Li M, Smith C M, et al. Helper T cells, dendritic cells and CTL Immunity. Immunol Cell Biol. 2004; 82:84-90.

Sansom D M, Walker L S K. The role of CD28 and cytotoxic T-lymphocyte antigen-4 (CTLA-4) in regulatory T-cell biology. Immunol Rev. 2006; 212:131-148.

Kuiper H M, Brouwer M, Linsley P S, van Lier R A W. Activated T Cells Can Induce High Levels of CTLA-4 Expression on B Cells. J. Immunol. 1995; 155:1776-1783.

Oaks M K, Hallett K M. Cutting Edge: A soluble form of CTLA-4 in patients with autoimmune thyroid disease. J. Immunol. 2000; 164:5015-5018.

Agris P F, Woolverton D K, Setzer D. Subcellular localization of S-adenosyl-L-methionine:tRNA methyltransferases with aminoacyl-tRNA synthetases in human and mouse: normal and leukemic leukocytes. Proc Natl Acad Sci USA. 1976; 73:3857-3861.

Mathews M B, Bernstein R M. Myositis autoantibody inhibits histidyl-tRNA synthetase: a model for autoimmunity. Nature. 1983; 304:177-179.

Bunn C C, Bernstein R M, Mathews M B. Autoantibodies against alanyl-tRNA synthetase and tRNAAla coexist and are associated with myositis. J Exp Med. 1986; 163:1281-1291.

Dang C V, Tan E, Traugh J A. Myositis autoantibody reactivity and catalytic function of threonyl-tRNA synthetase. FASEB J. 1988; 2:2376-2379.

Targoff, I N, Trieu E P, Miller F W. Reaction of anti-OJ autoantibodies with components of the multi-enzyme complex of aminoacyl-tRNA synthetases in addition to isoleucyl-tRNA synthetase. J Clin Invest. 1993; 91:2556-2562.

Vartanian O A. Detection of autoantibodies against phenylalanyl-, tyrosyl-, and tryptophanyl-tRNA synthetase and anti-idiotypic antibodies to it in serum from patients with autoimmune diseases. Mol Biol (Mosk). 1991; 25:1033-1039.

Arnett F C, Targoff I N, Mimori T, et al. Interrelationship of major histocompatibility complex class II alleles and autoantibodies in four ethnic groups with various forms of myositis. Arthritis Rheum. 1996; 39:1507-1518.

Beaulande M, Tarbouriech N, Hartlein M. Human cytosolic asparaginyl-tRNA synthetase; cDNA sequence, functional expression in *Escherichia coli* and characterization as human autoantigen. Nucleic Acids Res. 1998; 26:521-524.

Ohosone Y, Ishida M, Takahashi Y, et al. Spectrum and clinical significance of autoantibodies against transfer RNA. Arthritis Rheum. 1998; 41:1625-1631.

Ioannou, Y, Sultan S, Isenberg D A. Myositis overlap syndromes. Curr Opin Rheumatol. 1999; 11:468474.

Becker H F, Corda Y, Mathews M B, Fourrey J L, Grosjean H. Inosine and NI-methylinosine within a synthetic oligomer mimicking the anticodon loop of human tRNA(Ala) are major epitopes for anti-PL12 myositis antibodies. RNA 1999; 5:865-875.

Arnez J G, Dock-Bregon A-C, Moras D. Glycyl-tRNA Synthetase Uses a Negatively Charged Pit for Specific Recognition and Activation of Glycine. J Mol Biol. 1999; 286:1449-1459.

Yewdell J, Anton L C, Bacik I, et al. Generating MHC class I ligands from viral gene products. Immunol Rev. 1999; 172:97-108.

York I A, Goldberg A L, Mo X Y, Rock K L. Proteolysis and class I major histocompatibility complex antigen presentation. Immunol Rev. 1999; 172:49-66.

Pilarski L M. A requirement for antigen-specific helper T cells in the generation of cytotoxic T cells from thymocyte precursors. J Exp Med. 1977; 145:709-725.

Tucker M J, Bretscher P A. T-cells Cooperating in the Induction of Delayed-Type Hypersensitivity Act Via the Linked Recognition of Antigenic Determinants. J Exp Med. 1982; 155:1037-1049.

Shirai M, Pendleton C D, Ahlers J, et al. Helper-Cytotoxic T Lymphocyte (CTL) Determinant Linkage Required for Priming of Anti-HIV CD8+ CTL in Vivo with Peptide Vaccine Constructs. J. Immunol. 1994; 152:549-556.

Bretscher P A. A Cascade of T-T Interactions, Mediated by the Linked Recognition of Antigen, in the Induction of T Cells Able to Help Delayed-Type Hypersensitivity Responses. J. Immunol. 1986; 137:3726-3733.

The invention claimed is:

1. A method for inducing an immunologic response to a tumor in a patient comprising:
   (a) obtaining monocytic dendritic cell precursors from the patient, wherein the patient has breast cancer, a glioma, melanoma, pancreatic cancer or prostate cancer;
   (b) culturing the monocytic dendritic cell precursors to induce differentiation into immature dendritic cells;
   (c) differentiating the immature dendritic cells into mature dendritic cells by providing to said cells a tumor antigen composition comprising at least one Major Histocompatibility Complex (MHC) Class I epitope and at least one MHC Class II epitope, wherein the Class I and the Class II epitopes have a sequence overlap of at least 5 amino acids;
   (d) administering the mature dendritic cells to the patient.

2. The method of claim 1, wherein the mature dendritic cells are selected for CD83 expression, wherein the selected mature dendritic cells are enriched for cells expressing increased levels of CD83 as compared to reference dendritic cells contacted with a tumor antigen composition and not a nucleic acid composition.

3. The method of claim 2, wherein CD83 expression is at least 10-40% higher than the reference dendritic cells.

4. The method of claim 1, further comprising screening a patient or patient tumor for expression of one or more tumor antigens.

5. The method of claim 1, wherein the patient has breast cancer.

6. The method of claim 1, wherein the patient has a glioma.

7. The method of claim 1, wherein the patient has melanoma.

8. The method of claim 1, wherein the patient has pancreatic cancer.

9. The method of claim 1, wherein the patient has prostate cancer.

10. The method of claim 1, wherein differentiating the immature dendritic cells into mature dendritic cells in step (c) comprises:
    (i) transfecting into the immature dendritic cells a nucleic acid composition encoding one or more tumor antigens; and
    (ii) contacting the immature dendritic cells with a tumor antigen composition.

11. The method of claim 10, wherein the nucleic acid composition comprises total nucleic acid from a tumor source.

12. The method of claim 10, wherein the nucleic acid composition comprises mRNA isolated from a tumor source.

13. The method of claim 12, wherein the isolated mRNA is enriched for mRNA encoding tumor specific antigens.

14. The method of claim 13, wherein the isolated mRNA is subjected to mRNA subtraction using non-tumor cell RNA.

15. The method of claim 10, wherein the tumor antigen composition is an enriched tumor antigen composition.

16. The method of claim 15, wherein the enriched tumor antigen composition comprises a cellular fraction from cells of a tumor source.

17. The method of claim 15, wherein the cells from the tumor source are selected by removing cells expressing proteins that are typically not expressed or expressed at significantly reduced levels in a tumor cell.

18. The method of claim 15, wherein the cells from the tumor source are selected using cell surface markers preferentially expressed by tumor cells.

19. The method of claim 15, wherein the enriched tumor antigen composition comprises one or more protein fractions of a tumor cell lysate.

20. The method of claim 19, wherein the enriched tumor antigen composition is produced by contacting a tumor cell lysate with a protein array that preferentially binds non-tumor specific antigens.

21. The method of claim 10, wherein the nucleic acid composition comprises an expression construct.

22. The method of claim 21, wherein the expression construct encodes one or more tumor antigen.

23. The method of claim 10, wherein the immature dendritic cell is contacted with a tumor antigen composition comprising a recombinant identified tumor antigen.

24. The method of claim 10, wherein the nucleic acid composition encodes components of the tumor antigen composition.

25. The method of claim 10, wherein the immature dendritic cells are transfected with the nucleic acid composition prior to contact with the tumor antigen composition.

26. The method of claim 10, wherein the immature dendritic cells are contacted with the tumor antigen composition prior to transfection with the nucleic acid composition.

27. The method of claim 10, wherein the immature dendritic cells are simultaneously transfected with the nucleic acid composition and contacted with the tumor antigen composition.

28. The method of claim 1, wherein the MHC Class I or MHC Class II epitopes are comprised on separate peptides.

29. The method of claim 28, wherein the peptides are synthetic peptides.

* * * * *